(12) United States Patent
Wisniewski et al.

(10) Patent No.: US 9,644,000 B2
(45) Date of Patent: May 9, 2017

(54) V1A RECEPTOR AGONISTS

(71) Applicant: Ferring B.V., Hoofddorp (NL)

(72) Inventors: Kazimierz Wisniewski, San Diego, CA (US); Geoffrey S. Harris, Cardiff, CA (US); Robert Felix Galyean, Cottonwood, CA (US)

(73) Assignee: Ferring B.V., Hoofddorp (NL)

( * ) Notice: Subject to any disclaimer, the term of this patent is extended or adjusted under 35 U.S.C. 154(b) by 0 days.

(21) Appl. No.: 14/400,282

(22) PCT Filed: May 9, 2013

(86) PCT No.: PCT/US2013/040414
§ 371 (c)(1),
(2) Date: Nov. 10, 2014

(87) PCT Pub. No.: WO2013/170077
PCT Pub. Date: Nov. 14, 2013

(65) Prior Publication Data
US 2015/0126432 A1  May 7, 2015

Related U.S. Application Data

(60) Provisional application No. 61/645,558, filed on May 10, 2012.

(51) Int. Cl.
| | | |
|---|---|---|
| A01N 37/18 | (2006.01) |
| A61K 38/04 | (2006.01) |
| A61K 38/12 | (2006.01) |
| C07K 7/06 | (2006.01) |
| C07K 7/16 | (2006.01) |
| A61K 38/00 | (2006.01) |

(52) U.S. Cl.
CPC .............. C07K 7/06 (2013.01); C07K 7/16 (2013.01); *A61K 38/00* (2013.01)

(58) Field of Classification Search
CPC .............. C07K 7/06; C07K 7/16; A61K 38/00
See application file for complete search history.

(56) References Cited

U.S. PATENT DOCUMENTS 8,148,319 B2 * 4/2012 Wisniewski ............. C07K 7/16
514/1.1

FOREIGN PATENT DOCUMENTS

| EP | 1188443 | 3/2002 |
|---|---|---|
| WO | WO 2006/020491 | 2/2006 |
| WO | WO 2009/020934 | 2/2009 |

OTHER PUBLICATIONS

Response to Written Opinion, for PCT/US2013/040414, May 9, 2014, 10 pages.*

Zardi et al., Cirrhotic Cardiomyopathy, Journal of the American College of Cardiology vol. 56, No. 7, 2010, pp. 539-549.*
Bolognesi et al., "Splanchnic vasodilation and hyperdynamic circulatorysyndrome in cirrhosis", World J. Gastroenterol., 2014, 20(10), 2555-2563.*
Bisello et al., "Parathyroid hormone-receptor interactions identified directly by photocross-linking and molecular modeling studies," *J. Biol. Chem.*, 1998, 273, 22498-505.
Cardenas et al., "Tolvaptan, an oral vasopressin antagonist, in the treatment of hyponatremia in cirrhosis," *J. Hepatol.*, 2012, 56(3), 571-78.
Durroux et al., "Fluorescent Pseudo-Peptide Linear Vasopressin Antagonists: Design, Synthesis, and Applications,"*J. Med. Chem.*, 1999, 42, 1312-19.
Fimiani et al., "The use of terlipressin in cirrhotic patients with refractory ascites and normal renal function: a multicentric study," *Eur. J. Intern. Med.*, 2011, 22(6), 587-90.
Gulberg et al., "Long-term therapy and retreatment of hepatorenal syndrome type 1 with ornipressin and dopamine," *Hepatol.*, 1999, 30(4), 870-75.

(Continued)

*Primary Examiner* — Lianko Garyu
*Assistant Examiner* — Joseph Fischer
(74) *Attorney, Agent, or Firm* — Fish & Richardson P.C.

(57) ABSTRACT

Compounds of formula (I), salts thereof, and compositions and uses thereof are described. The compounds are useful as V1a vasopressin agonists, for the treatment of, e.g., complications of cirrhosis, including bacterial peritonitis, HRS2 and refractory ascites.

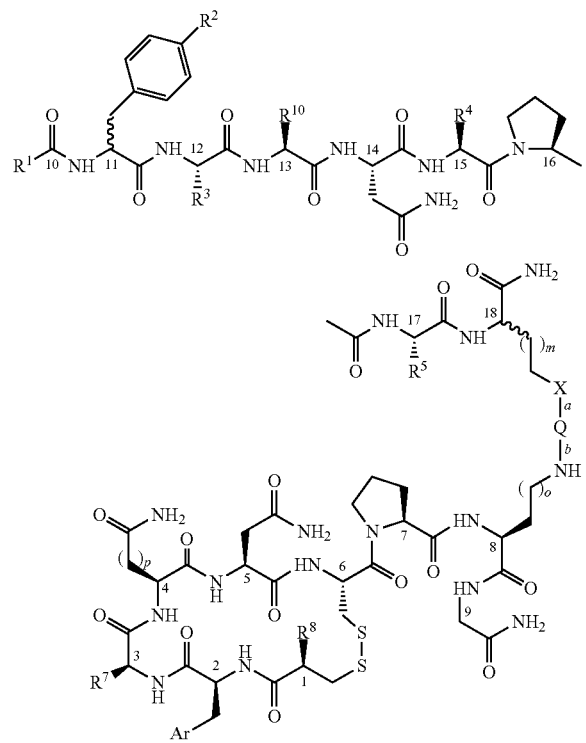

79 Claims, No Drawings

(56) References Cited

OTHER PUBLICATIONS

Howl et al., "Fluorescent and biotinylated linear peptides as selective bifunctional ligands for the V1a vasopressin receptor," *Eur. J Biochem.*, 1993, 213, 711-19.
Huguenin, "213. Synthesis of Phe2-Orn8-vasopressin and Phe2-Orn8-oxytocin, two vasopressin analogues endowed with selective pressor activity," *Helv. Chim. Acta*, 1964, 1934-41.
Lenz et al., "Beneficial effect of 8-ornithin vasopressin on renal dysfunction in decompensated cirrhosis," *Gut*, 1989, 30(1), 90-96.
Lenz et al., "Enhancement of renal function with ornipressin in a patient with decompensated cirrhosis," *Gut*, 1985, 26(12), 1385-86.
Russell et al., "Vasopressin versus norepinephrine infusion in patients with septic shock," *N. Engl. J Med.*, 2008, 358(9), 877-87.
Sanyal et al., "A randomized, prospective, double-blind, placebo-controlled trial of terlipressin for type 1 hepatorenal syndrome," *Gastroenterol*, 2008, 134(5), 1360-68.
Schmidt et al., "A radioiodinated linear vasopressin antagonist: A ligand with high affinity and specificity for V1a receptors," *FEBS Lett.*, 1991, 282(1), 77-81.
Terrillon et al., "Synthesis and Characterization of Fluorescent Antagonists and Agonists for Human Oxytocin and Vasopressin V1a Receptors," *J. Med. Chem.*, 2002, 45, 2579-88.
Wisniewski et al., "New, Potent, Selective, and Short-Acting Peptidic V1a Receptor Agonists," *J. Med. Chem*, 2011, 54, 4388-98.
Yefet et al., "Extensive Epidermal Necrosis due to Terlipressin," *IMAJ*, 2011, 13, 180-81.
Zhu, "Mechanistic explanation for the unique pharmacologic properties of receptor partial agonists," *Biomed. Pharmacother.*, 2005, 59, 76-89.
Zhu, "Rational Design of Receptor Partial Agonists and Possible Mechanisms of Receptor Partial Activation: A Theory," *J. Theor. Biol.*, 1996, 181, 273-91.
Bolognesi et al., Splanchnic vasodilation and hyperdynamic circulatory syndrome in cirrhosis, World J. Gastroenterol., 2014, 20(10), 2555-2563.
Enkhbaatar et al., Arginine vasopressin V1a agonist attenuates methicillin-resistant *Staphylococcus aureus*-induced vascular leakage by inhibiting bradykinin, Critical Care, 2013, 17(suppl. 4), Abstract No. P98 (Meeting Abstract of Sepsis 2013, Rio de Janeiro, Brazil, Nov. 5-6, 2013, p. 54).
Fernández-Varo et al., Vasopressin 1a receptor partial agonism increases sodium excretion and reduces portal hypertension and ascites in cirrhotic rats, Hepatology, 2016, 63(1), 207-16 (abstract).
Huang et al., Terlipressin Resolves Ascites of Cirrhotic Rats through Downregulation of Aquaporin 2, J. Int. Med. Res., 2012, 40, 1735-44.
Koshimizu et al., Vasopressin V1a and V1b Receptors: From Molecules to Physiological Systems, Physiol. Rev., 2012. 92, 1813-64.
Krag et al., Efficacy and safety of terlipressin in cirrhotic patients with variceal bleeding or hepatorenal syndrome, Adv. Ther., 2008, 25(11), 1105-40 (abstract).
Maybauer et al., The Selective V1a Receptor Agonist Selepressin (FE 202158) Blocks Vascular Leak in Ovine Severe Sepsis, Crit. Care. Med., 2014, 42(7), e525-33.
Triantos et al., Terlipressin Therapy for Renal Failure in Cirrhosis, Eur. J. Gastroenterol. Hepatol., 2010, 22(4), 481-86 (abstract).

\* cited by examiner

V1A RECEPTOR AGONISTS

CROSS-REFERENCE TO RELATED APPLICATIONS

This application is the national phase under 35 U.S.C. 371 of International Application No. PCT/US2013/040414, filed internationally on May 9, 2013, which claims the benefit of U.S. Provisional Application No. 61/645,558, filed May 10, 2012, the entire disclosure of which is hereby incorporated herein by reference.

TECHNICAL FIELD

This disclosure relates to peptide compounds, and more particularly to compounds which have partial V1a receptor agonist activity, compositions containing such compounds and uses of such compounds.

BACKGROUND

The vasopressin-vasopressin receptor system is involved in two key homeostatic functions. A principal function of vasopressin is to regulate osmolality of the blood through the V2 receptor (V2R) found in the kidney. A second function of vasopressin is as a pressor agent which is mediated by the V1a receptor (V1aR) found on blood vessels.

Experimentation has been performed with a number of vasopressin receptor agonists and antagonists for use in the treatment of a variety of diseases. Lenz, et al., *Gut*, 1985, 26(12), 1385-1386; Lenz, et al., *Gut*, 1989, 30(1), 90-96; Russell, et al., *N. Engl. J. Med.*, 2008, 358(9), 877-887; Fimiani, et al., *Eur. J. Intern. Med.*, 2011, 22(6), 587-590; Cardenas, et al., *J. Hepatol.*, 2012, 56(3), 571-578; Sanyal, et al., *Gastroenterol.*, 2008, 134(5), 1360-1368.

Of particular clinical interest is the use of vasopressin agonists for their pressor activity in patients with hypovolemia or hypotension in order to elevate arterial pressure. A significant drawback of existing full vasopressin agonists for this use is the potential to induce severe vasoconstriction and tissue hypoperfusion when used at pharmacological doses. Gulberg, et al., *Hepatol.*, 1999, 30(4), 870-875; Yefet, et al., *Isr. Med. Assoc. J.*, 2011, 13(3), 180-181; Sanyal, et al., *Gastroenterol.*, 2008, 134(5), 1360-1368. The narrow therapeutic index of these compounds has restricted their use to patients where the risk of tissue hypoperfusion is acceptable due to the severity of the underlying condition being treated.

The V2 receptor (V2R) is primarily found in the kidneys, in particular on the principal cells of the collecting ducts, where it is responsible for concentrating urine by reabsorbing water from the glomerular ultrafiltrate. This water retention can lead to hyponatremia if fluid intake is not restricted proportionately. The V2R is also found at extra-renal locations such as on endothelial cells where it appears to be responsible for a variety of effects, including release of von Willebrand factor and nitric oxide. The V1a receptor (V1aR) is primarily found on smooth muscle cells throughout the vasculature where it acts as a key regulator of vascular tone. The vasopressin analog, terlipressin, has been approved in some countries for the treatment of several cirrhotic complications (bleeding esophageal varices and type 1 hepatorenal syndrome) and has been used to demonstrate the utility of using vasoconstriction to treat other cirrhotic complications (spontaneous bacterial peritonitis, type-2 hepatorenal syndrome and post paracentesis circulatory dysfunction).

Cirrhosis of the liver is a common end stage of excessive alcohol consumption or of hepatitis. In about a third of cirrhosis patients, fluid builds up in the peritoneal cavity, and this is controlled by paracentesis. Complications of paracentesis include hypovolaemia and an undesirable fall in arterial blood pressure. These have traditionally been checked by infusion of human albumin, and more recently, terlipressin.

The development of portal hypertension as a consequence of cirrhosis is the key factor in the cardiovascular complications associated with end-stage liver disease. The liver has a normal hepatic venous pressure gradient (HVPG) of 1-5 mm Hg. An increase in HVPG is caused by active and passive increases in intrahepatic vascular resistance associated with the development of cirrhosis. This triggers a reflex splanchnic arteriolar vasodilation leading to increase in portal blood flow and further contributes to the increase in HVPG diagnosed as portal hypertension once it exceeds 12 mm Hg. This shift of the total blood volume towards the splanchnic circulation leads to a decrease in the effective blood volume (i.e., blood volume in the central portion of the cardiovascular system), which triggers reflex mechanisms aiming at increasing blood volume, essentially sodium and water retention mechanisms and vasoconstrictor mechanisms, further increasing the intensity of blood volume shift towards the splanchnic circulation which increases portal blood flow. Eventually, worsening vasoconstriction at the kidney starts reducing renal blood flow leading to either chronic (type II hepatorenal syndrome, HRS2) or acute renal failure (type I hepatorenal syndrome; HRS1) depending on the speed of deterioration. Both types of renal failure are very difficult to manage clinically (i.e., reversing excessive renal vasoconstriction) without worsening splanchnic vasodilation and portal hypertension.

Current medical management of the most severe cardiovascular complications of cirrhosis primarily relies on either vasoconstrictor therapy or albumin administration. Vasoconstrictor therapy targeted to specifically reduce splanchnic vasodilation without further deteriorating renal blood flow is the therapeutic intervention of choice. However, there is no current "gold standard" of care, as available vasoconstrictive agents tend to have significant liabilities, such as an ineffective degree of splanchnic vasoconstriction and/or excessive degree of extra-splanchnic vasoconstriction, too short a duration of action, or too narrow a therapeutic window. In European countries, the emerging standard of care for the treatment of HRS1 is administration of terlipressin. Other earlier, less severe complications of cirrhosis are often managed with albumin as a volume expander in the absence of a safe vasoconstrictor.

Terlipressin has been shown to be effective in treating HRS1 in a large-scale, randomized, placebo-controlled, blinded clinical trial (Orphan Therapeutics), providing proof of concept that vasoconstriction can be effective in treating renal failure in the context of cirrhosis (HRS1). Although the trial did not achieve its primary endpoint (survival with a reversal of HRS), terlipressin will likely become the therapeutic of choice for HRS1 in the regions of the world where it is approved. While terlipressin is considered better than fluid/albumin therapy alone, it is only able to reverse renal failure in 30-40% of patients, leaving room for improvement. Terlipressin has demonstrated clinical efficacy in bleeding esophageal varices (BEV) and HRS1, but it has drawbacks such as a relatively short duration of action when used at lower, and hence safer, doses, and too much extra-splanchnic vasoconstriction at higher doses. It is not practical to use terlipressin outside of a monitored, inpatient setting due to its need for frequent dosing (every 4-6 h or via IV infusion) and the potential for severe adverse events. While these severe adverse events are uncommon, they are potentially life threatening and must be managed accordingly.

SUMMARY

The present disclosure provides a compound according to formula (I):

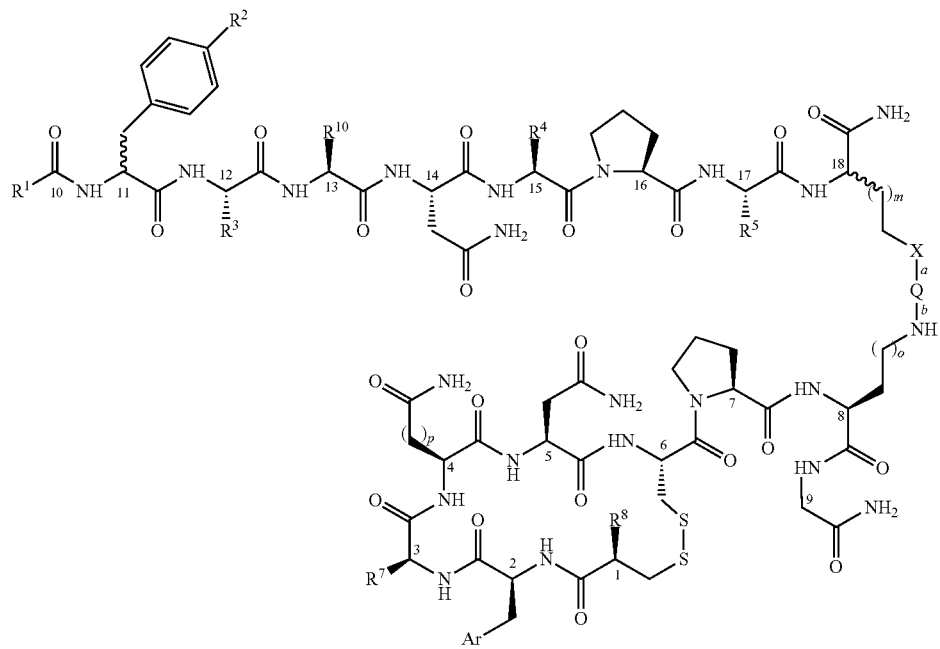

or a salt thereof, wherein:

$R^1$ is selected from $(C_1-C_{10})$alkyl, $(C_1-C_{10})$alkoxy, $(C_1-C_{10})$alkylNH, $Ar^1-L^1-$ and unsubstituted or substituted cycloalkyl;

$Ar^1-L^1-$ is selected from $Ar^1-$, $Ar^1-CH_2-$, $Ar^1-CH_2CH_2-$, $Ar^1-O-$, $Ar^1-CH_2O-$, $Ar^1-NH-$ and $Ar^1-CH_2NH-$;

$Ar^1$ is unsubstituted aryl or substituted aryl;

$R^2$ is selected from hydrogen, $(C_1-C_6)$alkyl, hydroxy, $(C_1-C_6)$alkoxy and halogen;

$R^3$ is selected from $(C_1-C_6)$alkyl, unsubstituted or substituted cycloalkyl and $Cy^3-CH_2-$;

$Cy^3-$ is unsubstituted or substituted aryl or unsubstituted or substituted cycloalkyl;

$R^4$ is selected from $(C_1-C_6)$alkyl, $(C_2-C_6)$alkenyl, $(C_2-C_6)$alkynyl, $(C_1-C_6)$haloalkyl, $-((C_1-C_6)$alkylene$)-OR^{4a}$, $-((C_1-C_6)$alkylene$)-NR^{4a}_2$, $-((C_1-C_6)$alkylene$)-S(C_1-C_6)$alkyl, $-((C_1-C_6)$alkylene$)-C(=O)OR^{4a}_2$, $-((C_1-C_6)$alkylene$)-C(=O)NR^{4a}_2$, $-((C_1-C_6)$alkylene$)-C(=NR^{4a})NR^{4a}_2$, $-((C_1-C_6)$alkylene$)-OC(=O)R^{4a}$, $-((C_1-C_6)$alkylene$)-OC(=O)OR^{4a}$, $-((C_1-C_6)$alkylene$)-OC(=O)NR^{4a}_2$, $-((C_1-C_6)$alkylene$)-NR^{4a}C(=O)R^{4a}$, $-((C_1-C_6)$alkylene$)-NR^{4a}C(=O)OR^{4a}$, $-((C_1-C_6)$alkylene$)-NR^{4a}C(=O)NR^{4a}_2$, $-((C_1-C_6)$alkylene$)-NR^{4a}C(=NR^{4a})NR^{4a}_2$, $Ar^4$ and $-((C_1-C_6)$alkylene$)-Ar^4$;

each $R^{4a}$ is independently selected from hydrogen and $(C_1-C_6)$alkyl;

$Ar^4$ is selected from unsubstituted or substituted aryl and unsubstituted or substituted heteroaryl;

$R^5$ is selected from $-((C_1-C_6)$alkylene$)-NR^{5a}_2$ and $-((C_1-C_6)$alkylene$)-NR^{5a}C(=NR^{5a})NR^{5a}_2$;

each $R^{5a}$ is independently selected from hydrogen and $(C_1-C_6)$alkyl;

Q is selected from the groups $Q^1$, $Q^2$, $Q^3$ and $Q^4$:

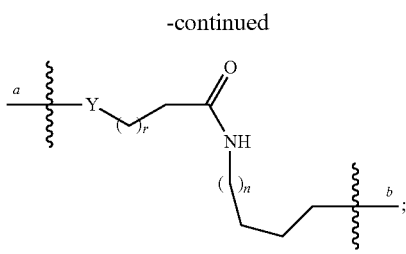

a and b denote the bonds attaching Q to the remainder of the molecule;

R$^6$ is selected from hydrogen, (C$_1$-C$_6$)alkyl and —C(=NR$^{6a}$)NR$^{6a}$$_2$;

each R$^{6a}$ is independently hydrogen or (C$_1$-C$_6$)alkyl;

R$^7$ is selected from (C$_1$-C$_6$)alkyl, unsubstituted aryl, substituted aryl, unsubstituted cycloalkyl and substituted cycloalkyl;

R$^8$ is selected from NH$_2$ and hydroxyl;

R$^9$ is selected from hydrogen, (C$_1$-C$_6$)alkyl, (C$_2$-C$_6$)alkenyl, (C$_2$-C$_6$)alkynyl, (C$_1$-C$_6$)haloalkyl, —((C$_1$-C$_6$)alkylene)-OR$^{9a}$, —((C$_1$-C$_6$)alkylene)-NR$^{9a}$$_2$; —((C$_1$-C$_6$)alkylene)-SR$^{9a}$, —((C$_1$-C$_6$)alkylene)-C(=O)OR$^{9a}$$_2$, —((C$_1$-C$_6$) alkylene)-C(=O)NR$^{9a}$$_2$, —((C$_1$-C$_6$)alkylene)-C(=NR$^{9a}$) NR$^{9a}$$_2$, —((C$_1$-C$_6$)alkylene)-OC(=O)R$^{9a}$, —((C$_1$-C$_6$) alkylene)-OC(=O)OR$^{9a}$, —((C$_1$-C$_6$)alkylene)-OC(=O) NR$^{9a}$$_2$, —((C$_1$-C$_6$)alkylene)-NR$^{9a}$C(=O)R$^{9b}$, —((C$_1$-C$_6$) alkylene)-NR$^{9a}$C(=O)OR$^{9a}$, —((C$_1$-C$_6$)alkylene)-NR$^{9a}$C (=O)NR$^{9a}$$_2$, —((C$_1$-C$_6$)alkylene)-NR$^{9a}$C(=NR$^{9a}$)NR$^{9a}$$_2$, Ar$^9$ and —((C$_1$-C$_6$)alkylene)-Ar$^9$;

each R$^{9a}$ is independently selected from hydrogen and (C$_1$-C$_6$)alkyl;

each R$^{9b}$ is independently selected from hydrogen and (C$_1$-C$_{10}$)alkyl;

Ar$^9$ is selected from unsubstituted aryl, substituted aryl, unsubstituted heteroaryl substituted heteroaryl;

R$^{10}$ is selected from —((C$_1$-C$_6$)alkylene)-OR$^{10a}$, —((C$_1$-C$_6$)alkylene)-C(=O)NR$^{10a}$$_2$ and Ar$^{10}$—CH$_2$—;

Ar$^{10}$ is unsubstituted heteroaryl or substituted heteroaryl;

each R$^{10a}$ is selected from hydrogen and (C$_1$-C$_6$)alkyl;

Ar is selected from aryl or substituted aryl;

each X is NH and each Y is C=O; or each X is C=O and each Y is NH;

m is 0, 1, 2, 3, 4 or 5;

n is 0, 1, 2, 3 or 4;

o is 1 or 2;

p is 1, 2 or 3; and r is 0, 1, 2, 3, 4, 5 or 6; provided that R$^9$ is hydrogen if r is greater than one.

Various embodiments of the disclosed compounds, including exemplary compounds are described.

Also described is a pharmaceutical composition that includes a compound of formula (I), or any of the embodiments thereof, or a pharmaceutically acceptable salt thereof, and a pharmaceutically acceptable carrier.

Methods of treatment using the compounds of formula (I) are also described. The methods include administering an effective amount of the compound of formula (I) or any of the embodiments thereof, or a pharmaceutically acceptable salt thereof, to an individual in need of the treatment.

The compounds are also useful for treating complications arising from cirrhosis, e.g., when increasing blood pressure is therapeutically desirable. Complications of cirrhosis that can be treated with the claimed compounds include bacterial peritonitis, type II heptoarenal syndrome or refractory ascites. The compounds are also useful, e.g., for increasing blood pressure. The compounds are also useful for treating hypovolemic shock; vasodilatory shock; bleeding esophageal varices; hepatorenal syndrome; type I hepatorenal syndrome; type II hepatorenal syndrome; anesthesia-induced hypotension; paracentesis-induced circulatory dysfunction; intra-operative blood loss; acute hemorrhage; blood loss associated with burn debridement; blood loss associated with epistaxis; spontaneous bacterial peritonitis; refractory ascites; hypertensive gastropathy bleeding; sepsis; severe sepsis; septic shock; hypotension, including orthostatic hypotension and intradialytic hypotension; cardiac arrest; trauma-related blood loss; vasodilatory shock induced by cardio-pulmonary bypass; milrinone-induced vasodilatory shock in congestive heart failure; anaphylactic shock; cardiovascular instability induced by brain death; acute respiratory distress syndrome; acute lung injury; shock induced by metformin intoxication; shock induced by mitochondrial disease; shock induced by cyanide poisoning; shock induced by vascular leak syndrome induced by interleukin-2, another cytokine, denileukin diftitox or another immunotoxin, or by ovarian hyperstimulation syndrome; hypotension induced by end-stage renal disease; inflammatory bowel disease; reperfusion injury; infant respiratory distress syndrome; severe acute respiratory syndrome; ascites; vasodepressor syncope; vasovagal syncope; toxic shock syndrome; and idiopathic systemic capillary leak syndrome.

Unless otherwise defined, all technical and scientific terms used herein have the same meaning as commonly understood by one of ordinary skill in the art to which this disclosure relates. Although methods and materials similar or equivalent to those described herein can be used in the practice or testing of the present invention, suitable methods and materials are described below. All publications, patent applications, patents and other references mentioned herein are incorporated by reference in their entirety. In case of conflict, the present specification, including definitions, will control. In addition, the materials, methods and examples are illustrative only and not intended to be limiting.

The details of one or more embodiments are set forth in the accompanying drawings and the description below. Other features, objects and advantages will be apparent from the description and drawings, and from the claims.

DETAILED DESCRIPTION

While not being limited by any theory, it is believed that a V1a vasopressin agonist with a ceiling on its vasoconstrictive potential can be used for treatment using a bolus dosing paradigm that can provide long duration of action with a consistent level of vasoconstriction, thereby dramatically improving safety, convenience and clinical efficacy in the reversal of renal failure associated with cirrhotic complications. It is believed that such compounds can provide improved safety allowing the use of such a vasoconstrictor in low intensity clinical settings or even as an outpatient product, thereby enabling the treatment of conditions such as spontaneous bacterial peritonitis, HRS2 and refractory ascites.

The disclosure describes selective, partial V1a agonists that can substantially deliver the clinical benefits of terlipressin, while providing improved safety and convenience through longer duration of action than terlipressin. Undesired fluctuations in vasoconstrictive effect are also thereby reduced. Such compounds could become the therapeutic agents of choice in the treatment of cardiovascular complications where reduction of portal hypertension is clinically efficacious. These advantages can enable the practical treatment of cirrhotic complications generally, where a full agonist compound would not be suitable.

Existing full agonist compounds such as terlipressin have a narrow therapeutic index. As the concentration of a full agonist drug increases, it is possible to exceed the therapeutic level of vasoconstriction and cause excessive vasoconstriction. This can result in severe tissue hypoxia and ischemia. Reduced maximal efficacy or "partial efficacy" compounds will be able to be used at much higher concentrations than would be possible with existing full agonist compounds while not causing undesired additional vasoconstriction. The maximal vasoconstrictive effect that is attainable with such compounds is reduced due to submaximal agonist activation of the V1a receptor.

In the present disclosure, it is appreciated that certain features described herein, which are, for clarity, described in the context of separate embodiments, can also be provided in combination in a single embodiment. Conversely, various features described herein which are, for brevity, described in the context of a single embodiment, can also be provided separately or in any suitable subcombination.

I. DEFINITIONS

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

As used herein, a "partial V1a agonist" is a compound which provides agonism (as determined by the FLIPR assay described herein) at the human V1a receptor of between about 15% and about 70% of that provided by arginine vasopressin (AVP), which is considered a full V1a agonist.

As used herein, "alkyl" refers to a saturated hydrocarbon chain that may be a straight chain or a branched chain. An alkyl group formally corresponds to an alkane with one C—H bond replaced by the point of attachment of the alkyl group to the remainder of the compound. The term "$(C_x$-$C_y)$alkyl" (wherein x and y are integers) by itself or as part of another substituent means, unless otherwise stated, an alkyl group containing from x to y carbon atoms. For example, a $(C_1$-$C_6)$alkyl group may have from one to six (inclusive) carbon atoms in it. Examples of $(C_1$-$C_6)$alkyl groups include, but are not limited to, methyl, ethyl, n-propyl, n-butyl, n-pentyl, n-hexyl, isopropyl, isobutyl, sec-butyl, tert-butyl, isopentyl, neopentyl and isohexyl. The $(C_x$-$C_y)$alkyl groups include $(C_1$-$C_{10})$alkyl, $(C_1$-$C_6)$alkyl, $(C_1$-$C_4)$alkyl and $(C_1$-$C_3)$alkyl.

The term "$(C_x$-$C_y)$alkylene" (wherein x and y are integers) refers to an alkylene group containing from x to y carbon atoms. An alkylene group formally corresponds to an alkane with two C—H bonds replaced by points of attachment of the alkylene group to the remainder of the compound. Examples are divalent straight hydrocarbon groups consisting of methylene groups, such as, —$CH_2$—, —$CH_2CH_2$— and —$CH_2CH_2CH_2$—. The $(C_x$-$C_y)$alkylene groups include $(C_1$-$C_6)$alkylene and $(C_1$-$C_3)$alkylene.

As used herein, "alkoxy" refers to the group R—O— where R is an alkyl group, as defined above. The term "$(C_x$-$C_y)$alkoxy" (wherein x and y are integers) by itself or as part of another substituent means, unless otherwise stated, an alkyl group containing from x to y carbon atoms. $(C_1$-$C_6)$alkoxy groups include, but are not limited to, methoxy, ethoxy, n-propoxy, isopropoxy, n-butoxy and t-butoxy. The $(C_x$-$C_y)$alkoxy groups include $(C_1$-$C_6)$alkoxy and $(C_1$-$C_3)$alkoxy.

As used herein, "alkenyl" refers to an unsaturated hydrocarbon chain that includes a C=C double bond. An alkenyl group formally corresponds to an alkene with one C—H bond replaced by the point of attachment of the alkenyl group to the remainder of the compound. The term "$(C_x$-$C_y)$alkenyl" (wherein x and y are integers) denotes a radical containing x to y carbons, wherein at least one carbon-carbon double bond is present (therefore x must be at least 2). Some embodiments are 2 to 4 carbons, some embodiments are 2 to 3 carbons and some embodiments have 2 carbons. Alkenyl groups may include both E and Z stereoisomers. An alkenyl group can include more than one double bond. Examples of alkenyl groups include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl, and the like.

As used herein, "alkynyl" refers to an unsaturated hydrocarbon chain that includes a C≡C triple bond. An alkynyl group formally corresponds to an alkyne with one C—H bond replaced by the point of attachment of the alkyl group to the remainder of the compound. The term "$(C_x$-$C_y)$alkynyl" (wherein x and y are integers) denotes a radical containing x to y carbons, wherein at least one carbon-carbon triple bond is present (therefore x must be at least 2). Some embodiments are 2 to 4 carbons, some embodiments are 2 to 3 carbons and some embodiments have 2 carbons. Examples of an alkynyl include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

As used herein, "halo" or "halogen" refers to —F, —Cl, —Br and —I.

The term "haloalkyl" as used herein refers to an alkyl group in which one or more of the hydrogen atoms has been replaced by a halogen atom. The term "$(C_x$-$C_y)$haloalkyl" (wherein x and y are integers) by itself or as part of another substituent means, unless otherwise stated, an alkyl group containing from x to y carbon atoms. The alkyl may be substituted with one halogen up to fully substituted, e.g., as represented by the formula $C_nF_{2n+1}$; when more than one halogen is present they may be the same or different and selected from F, Cl, Br or I. Some embodiments are 1 to 3 carbons. Haloalkyl groups may be straight-chained or branched. Examples include fluoromethyl, difluoromethyl, trifluoromethyl, chlorodifluoromethyl, 2,2,2-trifluoroethyl, pentafluoroethyl and the like. The term "perfluoroalkyl" denotes the group of the formula —$C_nF_{2n+1}$; stated differently, a perfluoroalkyl is an alkyl as defined herein wherein the alkyl is fully substituted with fluorine atoms and is therefore considered a subset of haloalkyl. Examples of perfluoroalkyls include $CF_3$, $CF_2CF_3$, $CF_2CF_2CF_3$, $CF(CF_3)_2$, $CF_2CF_2CF_2CF_3$, $CF_2CF(CF_3)_2$, $CF(CF_3)CF_2CF_3$ and the like.

As used herein, "cycloalkyl" refers to a non-aromatic, saturated, monocyclic, bicyclic or polycyclic hydrocarbon ring system. The term "$(C_x$-$C_y)$ cycloalkyl" (wherein x and y are integers) denotes a cycloalkyl group containing from x to y carbon atoms in the ring. Cycloalkyl groups include $(C_3-C_{12})$cycloalkyl, $(C_5-C_7)$cycloalkyl and $(C_6)$cycloalkyl. Representative examples of a $(C_3-C_{12})$cycloalkyl include, but are not limited to, cyclopropyl, cyclopentyl, cycloheptyl, cyclooctyl, decahydronaphthalen-1-yl, octahydro-1H-inden-2-yl, decahydro-1H-benzo[7]annulen-2-yl and dodecahydros-indacen-4-yl. Representative examples of a $(C_3-C_{10})$ cycloalkyl include, but are not limited to, cyclopropyl, cyclobutyl, cyclopentyl, cyclohexyl, cycloheptyl, cyclooctyl, decahydronaphthalen-1-yl and octahydro-1H-inden-2-yl. Representative examples of a $(C_3-C_8)$cycloalkyl include, but are not limited to, cyclopropyl, cyclobutyl, cyclopentyl, cyclohexyl, cycloheptyl, cyclooctyl and octahydropentalen-2-yl.

A cycloalkyl can be unsubstituted or substituted. A substituted cycloalkyl can be substituted with one or more groups, e.g., 1, 2 or 3 groups, including: $(C_1-C_6)$alkyl, $(C_2-C_6)$alkenyl, $(C_2-C_6)$alkynyl, halogen, $(C_1-C_6)$haloalkyl, —CN, —NO$_2$, —C(=O)R, —C(=O)OR, —C(=O)NR$_2$, —C(=NR)NR$_2$, —NR$_2$, —NRC(=O)R, —NRC(=O)O$(C_1-C_6)$alkyl, —NRC(=O)NR$_2$, —NRC(=NR)NR$_2$, —NRSO$_2$R, —OR, —O$(C_1-C_6)$haloalkyl, —OC(=O)R, —OC(=O)O$(C_1-C_6)$alkyl, —OC(=O)NR$_2$, —SR, —S(O)R, —SO$_2$R, —OSO$_2(C_1-C_6)$alkyl, —SO$_2$NR$_2$, —$(C_1-C_6)$alkylene-CN, —$(C_1-C_6)$alkylene-C(=O)OR, —$(C_1-C_6)$alkylene-C(=O)NR$_2$, —$(C_1-C_6)$alkylene-OR, —$(C_1-C_6)$alkylene-OC(=O)R, —$(C_1-C_6)$alkylene-NR$_2$, —$(C_1-C_6)$alkylene-NRC(=O)R, —NR$(C_1-C_6)$alkylene-C(=O)OR, —NR$(C_1-C_6)$alkylene-C(=O)NR$_2$, —NR$(C_2-C_6)$alkylene-OR, —NR$(C_2-C_6)$alkylene-OC(=O)R, —NR$(C_2-C_6)$alkylene-NR$_2$, —NR$(C_2-C_6)$alkylene-NRC(=O)R, —O$(C_1-C_6)$alkylene-C(=O)OR, —O$(C_1-C_6)$alkylene-C(=O)NR$_2$, —O$(C_2-C_6)$alkylene-OR, —O$(C_2-C_6)$alkylene-OC(=O)R, —O$(C_2-C_6)$alkylene-NR$_2$ and —O$(C_2-C_6)$alkylene-NRC(=O)R. Each R can be, independently, hydrogen or $(C_1-C_6)$alkyl. Additionally, each of any two hydrogen atoms on the same carbon atom of the carbocyclic ring can be replaced by an oxygen atom to form an oxo (=O) substituent.

The term "aromatic" refers to a carbocycle or heterocycle having one or more polyunsaturated rings having aromatic character (i.e., having (4n+2) delocalized π (pi) electrons where n is an integer).

As used herein, "aryl," employed alone or in combination with other terms, refers to an aromatic hydrocarbon group. The aryl group may be composed of, e.g., monocyclic or bicyclic rings and may contain, e.g., from 6 to 12 carbons in the ring, such as phenyl, biphenyl and naphthyl. The term "$(C_x-C_y)$aryl" (wherein x and y are integers) denotes an aryl group containing from x to y ring carbon atoms. Examples of a $(C_6-C_{14})$aryl group include, but are not limited to, phenyl, α-naphthyl, β-naphthyl, biphenyl, anthryl, tetrahydronaphthyl, fluorenyl, indanyl, biphenylenyl and acenanaphthyl. Examples of a $C_6-C_{10}$ aryl group include, but are not limited to, phenyl, α-naphthyl, β-naphthyl, biphenyl and tetrahydronaphthyl.

An aryl group can be unsubstituted or substituted. A substituted aryl group can be substituted with one or more groups, e.g., 1, 2 or 3 groups, including: $(C_1-C_6)$alkyl, $(C_2-C_6)$alkenyl, $(C_2-C_6)$alkynyl, halogen, $(C_1-C_6)$haloalkyl, —CN, —NO$_2$, —C(=O)R, —C(=O)OR, —C(=O)NR$_2$, —C(=NR)NR$_2$, —NR$_2$, —NRC(=O)R, —NRC(=O)O$(C_1-C_6)$alkyl, —NRC(=O)NR$_2$, —NRC(=NR)NR$_2$, —NRSO$_2$R, —OR, —O$(C_1-C_6)$haloalkyl, —OC(=O)R, —OC(=O)O$(C_1-C_6)$alkyl, —OC(=O)NR$_2$, —SR, —S(O)R, —SO$_2$R, —OSO$_2(C_1-C_6)$alkyl, —SO$_2$NR$_2$, —$(C_1-C_6)$alkylene-CN, —$(C_1-C_6)$alkylene-C(=O)OR, —$(C_1-C_6)$alkylene-C(=O)NR$_2$, —$(C_1-C_6)$alkylene-OR, —$(C_1-C_6)$alkylene-OC(=O)R, —$(C_1-C_6)$alkylene-NR$_2$, —$(C_1-C_6)$alkylene-NRC(=O)R, —NR$(C_1-C_6)$alkylene-C(=O)OR, —NR$(C_1-C_6)$alkylene-C(=O)NR$_2$, —NR$(C_2-C_6)$alkylene-OR, —NR$(C_2-C_6)$alkylene-OC(=O)R, —NR$(C_2-C_6)$alkylene-NR$_2$, —NR$(C_2-C_6)$alkylene-NRC(=O)R, —O$(C_1-C_6)$alkylene-C(=O)OR, —O$(C_1-C_6)$alkylene-C(=O)NR$_2$, —O$(C_2-C_6)$alkylene-OR, —O$(C_2-C_6)$alkylene-OC(=O)R, —O$(C_2-C_6)$alkylene-NR$_2$ and —O$(C_2-C_6)$alkylene-NRC(=O)R. Each R can be, independently, hydrogen or $(C_1-C_6)$alkyl.

The term "heteroaryl" or "heteroaromatic" as used herein refers to an aromatic ring system having at least one heteroatom in at least one ring, and from 2 to 9 carbon atoms in the ring system. The heteroaryl group has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaryls include furyl, thienyl, pyridyl, oxazolyl, pyrrolyl, indolyl, quinolinyl or isoquinolinyl, and the like. The heteroatoms of the heteroaryl ring system can include heteroatoms selected from one or more of nitrogen, oxygen and sulfur.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 1- and 5-quinoxalinyl, quinazolinyl, phthalazinyl, 1,5-naphthyridinyl, 1,8-naphthyridinyl, 1,4-benzodioxanyl, coumarin, dihydrocoumarin, benzofuryl, particularly 3-, 4-, 5-, 6- and 7-benzofuryl, 2,3-dihydrobenzofuryl, 1,2-benzisoxazolyl, benzothienyl, particularly 3-, 4-, 5-, 6- and 7-benzothienyl, benzoxazolyl, benzthiazolyl, particularly 2-benzothiazolyl and 5-benzothiazolyl, purinyl, benzimidazolyl, particularly 2-benzimidazolyl and benztriazolyl.

A heteroaryl group can be unsubstituted or substituted. A substituted heteroaryl group can be substituted with one or more groups, e.g., 1, 2 or 3 groups, including: $(C_1-C_6)$alkyl, $(C_2-C_6)$alkenyl, $(C_2-C_6)$alkynyl, halogen, $(C_1-C_6)$haloalkyl, —CN, —NO$_2$, —C(=O)R, —C(=O)OR, —C(=O)NR$_2$, —C(=NR)NR$_2$, —NR$_2$, —NRC(=O)R, —NRC(=O)O$(C_1-C_6)$alkyl, —NRC(=O)NR$_2$, —NRC(=NR)NR$_2$, —NRSO$_2$R, —OR, —O$(C_1-C_6)$haloalkyl, —OC(=O)R, —OC(=O)O$(C_1-C_6)$alkyl, —OC(=O)NR$_2$, —SR, —S(O)R, —SO$_2$R, —OSO$_2(C_1-C_6)$alkyl, —SO$_2$NR$_2$, —$(C_1-C_6)$alkylene-CN, —$(C_1-C_6)$alkylene-C(=O)OR, —$(C_1-C_6)$alkylene-C(=O)NR$_2$, —$(C_1-C_6)$alkylene-OR, —$(C_1-C_6)$alkylene-OC(=O)R, —$(C_1-C_6)$alkylene-NR$_2$, —$(C_1-C_6)$alkylene-NRC(=O)R, —NR$(C_1-C_6)$alkylene-C(=O)OR, —NR$(C_1-C_6)$alkylene-C(=O)NR$_2$, —NR$(C_2-C_6)$alkylene- OR, —NR($C_2$-$C_6$)alkylene-OC(=O)R, —NR($C_2$-$C_6$)alkylene-NR$_2$, —NR($C_2$-$C_6$)alkylene-NRC(=O)R, —O($C_1$-$C_6$)alkylene-C(=O)OR, —O($C_1$-$C_6$)alkylene-C(=O)NR$_2$, —O($C_2$-$C_6$)alkylene-OR, —O($C_2$-$C_6$)alkylene-OC(=O)R, —O($C_2$-$C_6$)alkylene-NR$_2$ and —O($C_2$-$C_6$)alkylene-NRC(=O)R. Each R can be, independently, hydrogen or ($C_1$-$C_6$)alkyl.

The aforementioned listing of heterocyclyl and heteroaryl moieties is intended to be representative and not limiting.

The term "substituted" means that an atom or group of atoms formally replaces hydrogen as a "substituent" attached to another group. The term "substituted", unless otherwise indicated, refers to any level of substitution, namely mono-, di-, tri-, tetra- or penta-substitution, where such substitution is permitted. The substituents are independently selected, and substitution may be at any chemically accessible position.

In the description herein and in the claims, the nomenclature common in the art of peptide, and more specifically, vasopressin chemistry is used. The amino acids in the substances can be either L- or D-amino acids. When no configuration is noted, the amino acid is in the L, or naturally occurring form. The thio members of the β-mercaptopropionic acid (1) and cysteine (6) units are added for clarity in certain structural formulas. Substances described herein also include peptides with sequences having reversed peptide bonds. These sequences are preferably inverted sequences, more preferably comprising D-amino acids.

The term "salt" includes any ionic form of a compound and one or more counter-ionic species (cations and/or anions). Salts also include zwitterionic compounds (i.e., a molecule containing one more cationic and anionic species, e.g., zwitterionic amino acids). Counter ions present in a salt can include any cationic, anionic, or zwitterionic species. Exemplary anions include, but are not limited to, chloride, bromide, iodide, nitrate, sulfate, bisulfate, sulfite, bisulfate, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluormethansulfonate, ethanesulfonate, benzenesulfonate, p-toluenesulfonate, p-trifluoromethylbenzenesulfonate, hydroxide, aluminates and borates. Exemplary cations include, but are not limited, to monovalent alkali metal cations, such as lithium, sodium, potassium and cesium, and divalent alkaline earth metals, such as beryllium, magnesium, calcium, strontium and barium. Also included are transition metal cations, such as gold, silver, copper and zinc, as well as non-metal cations, such as ammonium salts.

References to the compounds described and disclosed herein are considered to include both the free base and all addition salts. The addition salts may be either salts with pharmaceutically acceptable cations such as Na$^+$, Ca$^{2+}$, K$^+$ or Na$^+$ at a terminal acid group, such as when the C-terminal amino acid is Gly or OH is present, or with a pharmaceutically acceptable acid addition salt at a basic center of the peptide, such as in an Arg unit. The acetate salt forms are useful, and hydrochloride, hydrobromide and salts with other strong acids are also useful. In the isolation procedures outlined in the Examples, the peptide product is often isolated and purified as an acetate salt. The compounds may also form inner salts or zwitterions when a free terminal carboxy group is present. The term "pharmaceutically-acceptable salt" refers to salts which possess toxicity profiles within a range that affords utility in pharmaceutical applications. Pharmaceutically unacceptable salts may nonetheless possess properties such as high crystallinity, which may render them useful, e.g., in processes of synthesis, purification or formulation of compounds described herein. In general the useful properties of the compounds described herein do not depend on whether the compound is or is not in a salt form, so unless clearly indicated otherwise (such as specifying that the compound should be in "free base" or "free acid" form), reference in the specification to a compound should be understood as including salt forms of the compound, whether or not this is explicitly stated. Preparation and selection of suitable salt forms is described in Stahl, et al., *Handbook of Pharmaceutical Salts: Properties, Selection, and Use*, Wiley-VCH 2002.

When in the solid state, the compounds described herein and salts thereof may occur in various forms and may, e.g., take the form of solvates, including hydrates. In general, the useful properties of the compounds described herein do not depend on whether the compound or salt thereof is or is in a particular solid state form, such as a polymorph or solvate, so unless clearly indicated otherwise reference in the specification to compounds and salts should be understood as including any solid state form of the compound, whether or not this is explicitly stated.

Compounds provided herein can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expression "therapeutically effective amount," when used to describe an amount of compound administered in a method, refers to the amount of a compound that achieves the desired pharmacological effect or other effect, e.g., an amount that inhibits the abnormal growth or proliferation, or induces apoptosis of cancer cells, resulting in a useful effect.

The terms "treating" and "treatment" mean causing a therapeutically beneficial effect, such as ameliorating existing symptoms, preventing or reducing additional symptoms, ameliorating or preventing the underlying metabolic causes of symptoms, postponing or preventing the further development of a disorder, and/or reducing the severity of symptoms that will or are expected to develop.

The following abbreviations may also be found herein: AcOH (acetic acid); Boc (t-butoxycarbonyl); DCM (dichloromethane); DIAD (N,N'-diisopropyl azidodicarboxylate); DIC (N,N'-diisopropylcarbodiimide); DIPEA (N,N-diisopropylethylamine; DME (1,2-dimethoxyethane); DMF (N,N-dimethylformamide); Et (ethyl); Fmoc (9-fluorenylmethylmethoxycarbonyl); h (hour(s)); ivDde (1-(4,4-dimethyl-2,6-dioxocyclohex-1-ylidene)3-methylbutyl; HIPF (1,1,1,3,3,3-hexafluoro-2-propanol; HOBt (N-hydroxybenzotriazole); HPLC (high-performance liquid chromatography); LC (liquid chromatography); MeOH (methanol); MS (mass spectrometry); Mtt (4-methyltrityl); NMM (4-methylmorpholine); Pbf (2,2,4,6,7-pentamethyldihydrobenzofuran-5-sulfonyl); t-Bu (tert-butyl); TEAP (triethylammonium phosphate); TFA (trifluroracetic acid); TFE (2,2,2-trifluoroethanol); TIS (triisopropylsilane); TPP (triphenylphosphine); and Trt (trityl[triphenylmethyl, ($C_6H_5$)$_3$C—]).

Other abbreviations used herein are as follows: 3-Pal (3-pyridylalanine); 5-Ava (5-amino valeric acid); chexcarbonyl or cHxCO (cyclohexylcarbonyl); Orn (ornithine); Tyr(Me) (methoxy analog of tyrosine); Cit (citruline); Dab (2,4-diaminobutyric acid); Hmp (2-hydroxy-3-mercaptopropionic acid); Hgn (homoglutamine); iBuCO (isovaleroyl), beta-Ala (beta alanine; 3-amino propionic acid); and iso-hArg (isohomoarginine).

II. COMPOUNDS

Provided herein are peptidic partial V1a receptor agonists having a particular generic structural formula represented by formula (I) below:

alkylene)-NR$^{4a}$C(=O)OR$^{4a}$, —((C$_1$-C$_6$)alkylene)-NR$^{4a}$C(=O)NR$^{4a}$$_2$, —((C$_1$-C$_6$)alkylene)-NR$^{4a}$C(=NR$^{4a}$)NR$^{4a}$$_2$, Ar$^4$ and —((C$_1$-C$_6$)alkylene)-Ar$^4$;

each R$^{4a}$ is independently selected from hydrogen and (C$_1$-C$_6$)alkyl;

Ar$^4$ is selected from unsubstituted or substituted aryl and unsubstituted or substituted heteroaryl;

R$^5$ is selected from —((C$_1$-C$_6$)alkylene)-NR$^{5a}$$_2$ and —((C$_1$-C$_6$)alkylene)-NR$^{5a}$C(=NR$^{5a}$)NR$^{5a}$$_2$;

each R$^{5a}$ is independently selected from hydrogen and (C$_1$-C$_6$)alkyl;

Q is selected from the groups Q$^1$, Q$^2$, Q$^3$ and Q$^4$:

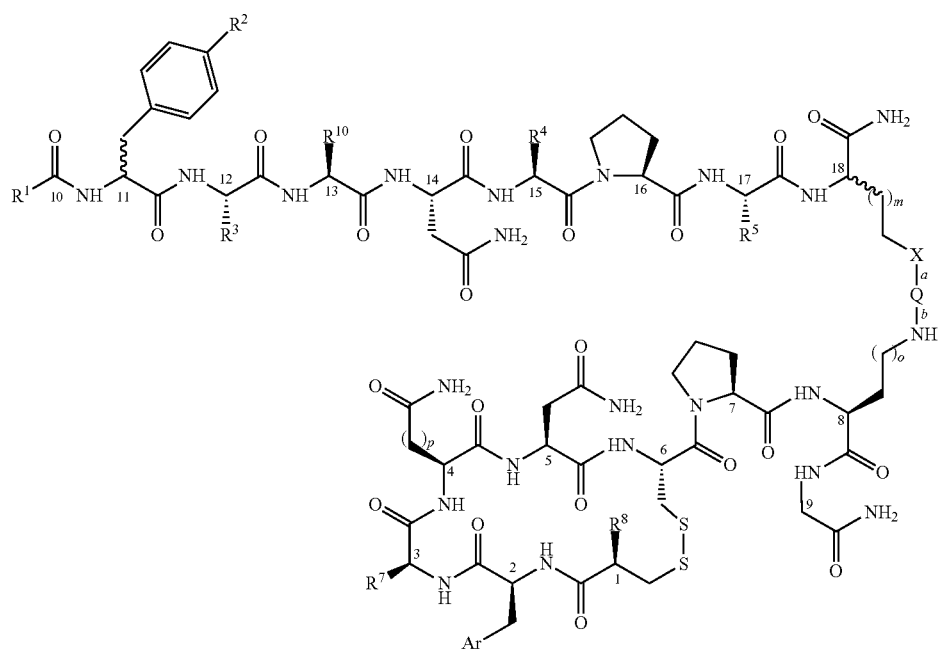

(I)

wherein:

R$^1$ is selected from (C$_1$-C$_{10}$)alkyl, (C$_1$-C$_{10}$)alkoxy, (C$_1$-C$_{10}$)alkylNH, Ar$^1$-L$^1$- and unsubstituted or substituted cycloalkyl;

Ar$^1$-L$^1$- is selected from Ar$^1$—, Ar$^1$—CH$_2$—, Ar$^1$—CH$_2$CH$_2$—, Ar$^1$—O—, Ar$^1$—CH$_2$O—, Ar$^1$—NH— and Ar$^1$—CH$_2$NH—;

Ar$^1$ is unsubstituted aryl or substituted aryl;

R$^2$ is selected from hydrogen, (C$_1$-C$_6$)alkyl, hydroxy, (C$_1$-C$_6$)alkoxy and halogen;

R$^3$ is selected from (C$_1$-C$_6$)alkyl, unsubstituted or substituted cycloalkyl and Cy$^3$-CH$_2$—;

Cy$^3$- is unsubstituted or substituted aryl or unsubstituted or substituted cycloalkyl;

R$^4$ is selected from (C$_1$-C$_6$)alkyl, (C$_2$-C$_6$)alkenyl, (C$_2$-C$_6$)alkynyl, (C$_1$-C$_6$)haloalkyl, —((C$_1$-C$_6$)alkylene)-OR$^{4a}$, —((C$_1$-C$_6$)alkylene)-NR$^{4a}$$_2$, —((C$_1$-C$_6$)alkylene)-S(C$_1$-C$_6$)alkyl, —((C$_1$-C$_6$)alkylene)-C(=O)OR$^{4a}$, —((C$_1$-C$_6$)alkylene)-C(=O)NR$^{4a}$$_2$, —((C$_1$-C$_6$)alkylene)-C(=NR$^{4a}$)NR$^{4a}$$_2$, —((C$_1$-C$_6$)alkylene)-OC(=O)R$^{4a}$, —((C$_1$-C$_6$)alkylene)-OC(=O)OR$^{4a}$, —((C$_1$-C$_6$)alkylene)-OC(=O)NR$^{4a}$$_2$, —((C$_1$-C$_6$)alkylene)-NR$^{4a}$C(=O)R$^{4a}$, —((C$_1$-C$_6$)

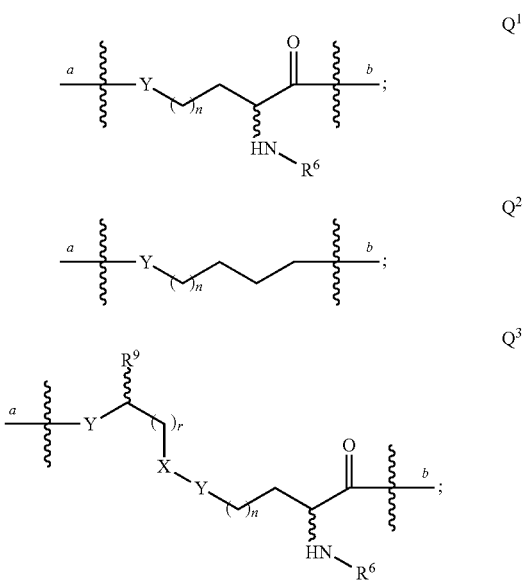

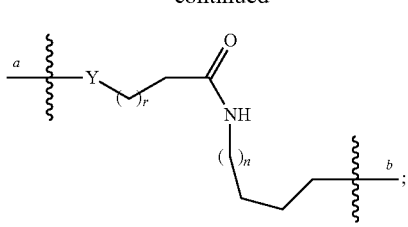

a and b denote the bonds attaching Q to the remainder of the molecule;

$R^6$ is selected from hydrogen, $(C_1\text{-}C_6)$alkyl and $-C(=NR^{6a})NR^{6a}_2$;

each $R^{6a}$ is hydrogen or $(C_1\text{-}C_6)$alkyl;

$R^7$ is selected from $(C_1\text{-}C_6)$alkyl, unsubstituted aryl, substituted aryl, unsubstituted cycloalkyl and substituted cycloalkyl;

$R^8$ is selected from $NH_2$ and hydroxyl;

$R^9$ is selected from hydrogen, $(C_1\text{-}C_6)$alkyl, $(C_2\text{-}C_6)$alkenyl, $(C_2\text{-}C_6)$alkynyl, $(C_1\text{-}C_6)$haloalkyl, $-((C_1\text{-}C_6)$alkylene)-$OR^{9a}$, $-((C_1\text{-}C_6)$alkylene)-$NR^{9a}_2$, $-((C_1\text{-}C_6)$alkylene)-$SR^{9a}$, $-((C_1\text{-}C_6)$alkylene)-$C(=O)OR^{9a}_2$, $-((C_1\text{-}C_6)$alkylene)-$C(=O)NR^{9a}_2$, $-((C_1\text{-}C_6)$alkylene)-$C(=NR^{9a})NR^{9a}_2$, $-((C_1\text{-}C_6)$alkylene)-$OC(=O)R^{9a}$, $-((C_1\text{-}C_6)$alkylene)-$OC(=O)OR^{9a}$, $-((C_1\text{-}C_6)$alkylene)-$OC(=O)NR^{9a}_2$, $-((C_1\text{-}C_6)$alkylene)-$NR^{9a}C(=O)R^{9b}$, $-((C_1\text{-}C_6)$alkylene)-$NR^{9a}C(=O)OR^{9a}$, $-((C_1\text{-}C_6)$alkylene)-$NR^{9a}C(=O)NR^{9a}_2$, $-((C_1\text{-}C_6)$alkylene)-$NR^{9a}C(=NR^{9a})NR^{9a}_2$, $Ar^9$ and $-((C_1\text{-}C_6)$alkylene)-$Ar^9$;

each $R^{9a}$ is independently selected from hydrogen and $(C_1\text{-}C_6)$alkyl;

each $R^{9b}$ is independently selected from hydrogen and $(C_1\text{-}C_{10})$alkyl;

$Ar^9$ is selected from unsubstituted aryl, substituted aryl, unsubstituted heteroaryl substituted heteroaryl;

$R^{10}$ is selected from $-((C_1\text{-}C_6)$alkylene)-$OR^{10a}$, $-((C_1\text{-}C_6)$alkylene)-$C(=O)NR^{10a}_2$ and $Ar^{10}$—$CH_2$—;

$Ar^{10}$ is unsubstituted heteroaryl or substituted heteroaryl;

each $R^{10a}$ is selected from hydrogen and $(C_1\text{-}C_6)$alkyl;

Ar is selected from aryl or substituted aryl;

each X is NH and each Y is C=O; or
each X is C=O and each Y is NH;

m is 0, 1, 2, 3, 4 or 5;

n is 0, 1, 2, 3 or 4;

o is 1 or 2;

p is 1, 2 or 3; and r is 0, 1, 2, 3, 4, 5 or 6; provided that $R^9$ is hydrogen if r is greater than one.

In some embodiments, $R^1$ can be $(C_1\text{-}C_{10})$alkyl, e.g., $(C_1\text{-}C_7)$alkyl, $(C_1\text{-}C_6)$alkyl or $(C_1\text{-}C_4)$alkyl. $R^1$ can be, e.g., methyl, ethyl, n-propyl, isopropyl, isobutyl, sec-butyl, tert-butyl, neopentyl, n-hexyl or n-heptyl. In some embodiments, $R^1$ can be $(C_1\text{-}C_{10})$alkoxy, e.g., $(C_1\text{-}C_7)$alkoxy or $(C_1\text{-}C_6)$alkoxy. $R^1$ can be, e.g., methoxy, ethoxy, n-propoxy, isopropoxy, isobutoxy, sec-butoxy, tert-butoxy, neopentoxy, n-hexyloxy or n-heptoxy. In some embodiments, $R^1$ can be $(C_1\text{-}C_{10})$alkylamino, e.g., $(C_1\text{-}C_7)$alkylamino or $(C_1\text{-}C_6)$alkylamino $R^1$ can be, e.g., methylamino, ethylamino, n-propylamino, isopropylamino, isobutylamino, sec-butylamino, tert-butylamino, neopentylamino, n-hexylamino or n-heptylamino.

In some embodiments, $R^1$ can be unsubstituted or substituted cycloalkyl, e.g., $(C_3\text{-}C_{12})$cycloalkyl, e.g., $(C_5\text{-}C_7)$cycloalkyl or $(C_6)$cycloalkyl. $R^1$ can be, e.g., cyclopropyl, cyclobutyl, cyclopentyl, cyclohexyl or cycloheptyl. In some embodiments, the cycloalkyl can be unsubstituted. In some embodiments, the cycloalkyl can be substituted. When $R^1$ is substituted cycloalkyl, the cycloalkyl can be substituted, e.g., by 1, 2 or 3 substituents independently selected from $(C_1\text{-}C_6)$alkyl, $(C_2\text{-}C_6)$alkenyl, $(C_2\text{-}C_6)$alkynyl, halogen, $(C_1\text{-}C_6)$haloalkyl, $-OR^{1a}$ and oxo, wherein each $R^{1a}$ is independently selected from hydrogen and $(C_1\text{-}C_6)$alkyl, e.g., methyl, ethyl, n-propyl, isopropyl, isobutyl, sec-butyl, tert-butyl, neopentyl or n-hexyl.

In some embodiments, $R^1$ can be represented by the formula $Ar^1\text{-}L^1\text{-}$, wherein $Ar^1\text{-}L^1\text{-}$ can be $Ar^1$—, $Ar^1$—$CH_2$—, $Ar^1$—$CH_2CH_2$—, $Ar^1$—O—, $Ar^1$—$CH_2$O—, $Ar^1$—NH— or $Ar^1$—$CH_2$NH—. In some embodiments, $Ar^1\text{-}L^1\text{-}$ can be $Ar^1$—$CH_2$—. In some embodiments, $Ar^1\text{-}L^1\text{-}$ can be $Ar^1$— or $Ar^1$—$CH_2CH_2$—. $Ar^1$ is unsubstituted aryl or substituted aryl, e.g., unsubstituted or substituted phenyl. When $Ar^1$ is substituted, the aryl, e.g., phenyl, can be substituted, e.g., by 1, 2 or 3 substituents independently selected from $(C_1\text{-}C_6)$alkyl, $(C_2\text{-}C_6)$alkenyl, $(C_2\text{-}C_6)$alkynyl, halogen, $(C_1\text{-}C_6)$haloalkyl, —CN, —$NO_2$, —$OR^{1a}$, —$NR^{1a}_2$ and —$NR^{1a}C(=O)R^{1a}$, wherein each $R^{1a}$ is independently selected from hydrogen and $(C_1\text{-}C_6)$alkyl, e.g., methyl, ethyl, n-propyl, isopropyl, isobutyl, sec-butyl, tert-butyl, neopentyl or n-hexyl.

In some embodiments, $R^1$ is $(C_1\text{-}C_{10})$alkyl, $(C_5\text{-}C_7)$cycloalkyl or $Ar^1$—$CH_2$—. In some embodiments, $R^1$ is isobutyl, n-hexyl or cyclohexyl. In some embodiments, $R^1$ is benzyl.

In some embodiments, $R^2$ can be $(C_1\text{-}C_6)$alkyl, e.g., $(C_1\text{-}C_4)$alkyl. $R^2$ can be, e.g., methyl, ethyl, n-propyl, isopropyl, isobutyl, sec-butyl, tert-butyl, neopentyl or n-hexyl. In some embodiments, $R^2$ can be hydroxy. In some embodiments, $R^2$ can be $(C_1\text{-}C_6)$alkoxy, e.g., $(C_1\text{-}C_4)$alkoxy. $R^2$ can be, e.g., methoxy, ethoxy, n-propoxy, isopropoxy, isobutoxy, sec-butoxy, tert-butoxy, neopentoxy or n-hexoxy. In some embodiments, $R^2$ can be methoxy. In some embodiments, $R^2$ can be halogen, e.g., fluoro, chloro or bromo.

In some embodiments, the amino acid having the carbon atom numbered 11 as its α-carbon atom has D configuration, or, in other embodiments, L configuration. The amino acid can be, e.g., D-O-methyl-tyrosine, D-p-chlorophenylalanine, L-O-methyl-tyrosine or L-p-chlorophenylalanine, In some embodiments, $R^3$ can be $(C_1\text{-}C_6)$alkyl, e.g., $(C_1\text{-}C_4)$alkyl. $R^3$ can be, e.g., methyl, ethyl, n-propyl, isopropyl, isobutyl, sec-butyl, tert-butyl, neopentyl or n-hexyl.

In some embodiments, $R^3$ can be unsubstituted or substituted cycloalkyl or $Cy^3$-$CH_2$—, wherein $Cy^3$ is unsubstituted or substituted cycloalkyl. The cycloalkyl can be, e.g., $(C_3\text{-}C_{12})$cycloalkyl, e.g., $(C_5\text{-}C_7)$cycloalkyl or $(C_6)$cycloalkyl, e.g., cyclopropyl, cyclobutyl, cyclopentyl, cyclohexyl or cycloheptyl. In some embodiments, the cycloalkyl, alone or as part of $Cy^3$-$CH_2$—, can be unsubstituted. In some embodiments, the cycloalkyl, alone or as part of $Cy^3$-$CH_2$—, can be substituted. When substituted, the cycloalkyl, can be substituted, e.g., by 1, 2 or 3 substituents independently selected from $(C_1\text{-}C_6)$alkyl, $(C_2\text{-}C_6)$alkenyl, $(C_2\text{-}C_6)$alkynyl, halogen, $(C_1\text{-}C_6)$haloalkyl, —$OR^{3a}$ and oxo, wherein each $R^{3a}$ is independently selected from hydrogen and $(C_1\text{-}C_6)$alkyl, e.g., methyl, ethyl, n-propyl, isopropyl, isobutyl, sec-butyl, tert-butyl, neopentyl or n-hexyl.

In some embodiments, $R^3$ can be $Cy^3$-$CH_2$—, wherein $Cy^3$ is unsubstituted or substituted aryl ($Ar^3$). $Ar^3$ is unsubstituted aryl or substituted aryl, e.g., unsubstituted or substituted phenyl. In some embodiments, when $Ar^3$ is substituted, the aryl, e.g., phenyl, can be substituted, e.g., by 1, 2 or 3 substituents independently selected from $(C_1\text{-}C_6)$alkyl, $(C_2\text{-}C_6)$alkenyl, $(C_2\text{-}C_6)$alkynyl, halogen, $(C_1\text{-}C_6)$haloalkyl, —CN, —NO$_2$, —OR$^{3a}$, —NR$^{3a}_2$ and —NR$^{3a}$C(=O)R$^{3a}$, wherein each R$^{3a}$ is independently selected from hydrogen and (C$_1$-C$_6$)alkyl, e.g., methyl, ethyl, n-propyl, isopropyl, isobutyl, sec-butyl, tert-butyl, neopentyl or n-hexyl. In some embodiments, the substituted aryl, e.g., phenyl, is halo-substituted, e.g., mono-halo-substituted.

In some embodiments, R$^3$ is selected from (C$_1$-C$_6$)alkyl and Ar$^3$—CH$_2$—, wherein Ar$^3$— is unsubstituted or substituted aryl. In some embodiments, Ar$^3$ is unsubstituted aryl or halo-substituted aryl. In some embodiments, Ar$^3$ is phenyl. In some embodiments, Ar$^3$ can be phenyl or phenyl substituted with hydroxy, alkoxy or halogen, e.g., 4-chlorophenyl. In some embodiments, R$^3$ is selected from (C$_1$-C$_6$)alkyl and Ar$^3$—CH$_2$—, wherein Ar$^3$ is phenyl or halo-substituted phenyl. In some embodiments, R$^3$ is s-butyl, neopentyl, benzyl or 4-chlorobenzyl.

In some embodiments, the amino acid having the carbon atom numbered 12 as its α-carbon atom (i.e., with R$^3$ as its side-chain) can be, e.g., alanine, leucine, isoleucine, valine, phenylalanine, 4-chlorophenylalanine or tyrosine.

In some embodiments, R$^4$ can be (C$_1$-C$_{10}$)alkyl, e.g., (C$_1$-C$_7$)alkyl or (C$_1$-C$_6$)alkyl. R$^4$ can be, e.g., methyl, ethyl, n-propyl, isopropyl, isobutyl, sec-butyl, tert-butyl, neopentyl, n-hexyl or n-heptyl.

In some embodiments, R$^4$ can be —((C$_1$-C$_6$)alkylene)-OR$^{4a}$, —((C$_1$-C$_6$)alkylene)-OR$^{4a}$, —((C$_1$-C$_6$)alkylene)-NR$^{4a}_2$, —((C$_1$-C$_6$)alkylene)-S(C$_1$-C$_6$)alkyl, —((C$_1$-C$_6$)alkylene)-C(=O)OR$^{4a}_2$, —((C$_1$-C$_6$)alkylene)-C(=O)NR$^{4a}_2$, —((C$_1$-C$_6$)alkylene)-C(=NR$^{4a}$)NR$^{4a}_2$, —((C$_1$-C$_6$)alkylene)-OC(=O)R$^{4a}$, —((C$_1$-C$_6$)alkylene)-OC(=O)OR$^{4a}$, —((C$_1$-C$_6$)alkylene)-OC(=O)NR$^{4a}_2$, —((C$_1$-C$_6$)alkylene)-NR$^{4a}$C(=O)R$^{4a}$, —((C$_1$-C$_6$)alkylene)-NR$^{4a}$C(=O)OR$^{4a}$, —((C$_1$-C$_6$)alkylene)-NR$^{4a}$C(=O)NR$^{4a}_2$, —((C$_1$-C$_6$)alkylene)-NR$^{4a}$C(=NR$^{4a}$)NR$^{4a}_2$ or —((C$_1$-C$_6$)alkylene)-Ar$^4$, wherein R$^{4a}$ is hydrogen or (C$_1$-C$_6$)alkyl, e.g., methyl. The (C$_1$-C$_6$)alkylene chain can have 1, 2, 3, 4, 5 or 6 carbon atoms and can be composed of methylene groups. For example, R$^4$ can be of the formula —(CH$_2$)$_{1-6}$—OR$^{4a}$, —(CH$_2$)$_{1-6}$—NR$^{4a}_2$, —(CH$_2$)$_{1-6}$—C(=O)NR$^{4a}_2$, —(CH$_2$)$_{1-6}$—NR$^{4a}$C(=O)NR$^{4a}_2$, —(CH$_2$)$_{1-6}$—NR$^{4a}$C(=NR$^{4a}$)NR$^{4a}_2$ and —(CH$_2$)$_{1-6}$—Ar$^4$, e.g., —(CH$_2$)—OR$^{4a}$, —(CH$_2$)$_{2-4}$—NR$^{4a}_2$, —(CH$_2$)$_{1-3}$—C(=O)NR$^{4a}_2$, —(CH$_2$)$_{2-4}$—NR$^{4a}$C(=O)NR$^{4a}_2$, —(CH$_2$)$_{2-4}$—NR$^{4a}$C(=NR$^{4a}$)NR$^{4a}_2$ and —(CH$_2$)—Ar$^4$.

In some embodiments, R$^4$ is (C$_1$-C$_6$)alkyl, —((C$_1$-C$_6$)alkylene)-OR$^{4a}$, —((C$_1$-C$_6$)alkylene)-NR$^{4a}_2$, —((C$_1$-C$_6$)alkylene)-C(=O)NR$^{4a}_2$, —((C$_1$-C$_6$)alkylene)-NR$^{4a}$C(=O)NR$^{4a}_2$, —((C$_1$-C$_6$)alkylene)-NR$^{4a}$C(=NR$^{4a}$)NR$^{4a}_2$ or —((C$_1$-C$_6$)alkylene)-Ar$^4$. In some embodiments, R$^4$ is selected from (C$_1$-C$_6$)alkyl, —(CH$_2$)$_{1-6}$—OR$^{4a}$, —(CH$_2$)$_{1-6}$—NR$^{4a}_2$, —(CH$_2$)$_{1-6}$—C(=O)NR$^{4a}_2$, —(CH$_2$)$_{1-6}$—NR$^{4a}$C(=O)NR$^{4a}_2$, —(CH$_2$)$_{1-6}$—NR$^{4a}$C(=NR$^{4a}$)NR$^{4a}_2$ and —(CH$_2$)$_{1-6}$—Ar$^4$. In some embodiments, R$^4$ is selected from (C$_1$-C$_6$)alkyl, —(CH$_2$)—OR$^{4a}$, —(CH$_2$)$_{2-4}$—NR$^{4a}_2$, —(CH$_2$)$_{1-3}$—C(=O)NR$^{4a}_2$, —(CH$_2$)$_{2-4}$—NR$^{4a}$C(=O)NR$^{4a}_2$, —(CH$_2$)$_{2-4}$—NR$^{4a}$C(=NR$^{4a}$)NR$^{4a}_2$ and —(CH$_2$)—Ar$^4$.

In R$^4$, each R$^{4a}$ can be, independently, hydrogen or (C$_1$-C$_6$)alkyl, e.g., methyl. In some embodiments, each R$^{4a}$ is independently hydrogen or methyl. In some embodiments, each R$^{4a}$ is hydrogen. In some embodiments, when R$^4$ has more than one R$^{4a}$ group all of the R$^{4a}$ groups are hydrogen, or only one of the R$^{4a}$ groups is (C$_1$-C$_6$)alkyl, e.g., methyl.

In R$^4$, and embodiments thereof, Ar$^4$ can be unsubstituted aryl or substituted aryl, e.g., unsubstituted or substituted phenyl or unsubstituted or substituted heteroaryl. When Ar$^4$ is substituted, the aryl, e.g., phenyl, or heteroaryl can be substituted, e.g., by 1, 2 or 3 substituents independently selected from (C$_1$-C$_6$)alkyl, (C$_2$-C$_6$)alkenyl, (C$_2$-C$_6$)alkynyl, halogen, (C$_1$-C$_6$)haloalkyl, —CN, —NO$_2$, —OR$^{4b}$, —NR$^{4b}_2$ and —NR$^{4b}$C(=O)R$^{4b}$, wherein each R$^{4b}$ is independently selected from hydrogen and (C$_1$-C$_6$)alkyl, e.g., methyl, ethyl, n-propyl, isopropyl, isobutyl, sec-butyl, tert-butyl, neopentyl or n-hexyl. In some embodiments, Ar$^4$ is heteroaryl, e.g., unsubstituted heteroaryl, e.g., pyridyl, pyrazinyl, pyrimidinyl, pyridazinyl, thienyl, furyl, pyrrolyl, imidazolyl, thiazolyl, oxazolyl, pyrazolyl, pyrazolyl, isothiazolyl, triazolyl, tetrazolyl, thiadiazolyl, oxadiazolyl, indolyl, indolinyl, quinolyl, isoquinolyl, benzofuryl, benzothienyl, benzoxazolyl, benzthiazolyl and benzimidazolyl. In some embodiments, Ar$^4$ is imidazolyl, e.g., 1H-imidazol-4-yl or indolyl, e.g., indol-3-yl.

In some embodiments, R$^4$ is methyl, isobutyl, —CH$_2$OH, —(CH$_2$)$_2$—NH$_2$, —(CH$_2$)$_3$—NH$_2$, —(CH$_2$)$_4$—NH$_2$, —(CH$_2$)$_2$—C(=O)NH$_2$, —(CH$_2$)$_3$—NHC(=NH)NH$_2$, —(CH$_2$)$_3$—NHC(=O)NH$_2$ or —CH$_2$(1H-imidazol-4-yl).

In some embodiments, the amino acid having the carbon atom numbered 15 as its α-carbon atom (i.e., with R$^4$ as its side-chain) can be, e.g., alanine, arginine, asparagine, citrulline, 2,4-diaminobutyric acid, glutamine, histidine, isoleucine, leucine, lysine, ornithine, phenylalanine, serine, tryptophan or valine.

R$^5$ is —((C$_1$-C$_6$)alkylene)-NR$^{5a}_2$ or —((C$_1$-C$_6$)alkylene)-NR$^{5a}$C(=NR$^{5a}$)NR$^{5a}_2$; wherein each R$^{5a}$ is independently hydrogen or (C$_1$-C$_6$)alkyl, e.g., methyl. The (C$_1$-C$_6$)alkylene chain can have 1, 2, 3, 4, 5 or 6 carbon atoms and can be composed of methylene groups. For example, R$^5$ can be of the formula —(CH$_2$)$_{1-6}$—NR$^{5a}_2$, or of the formula —(CH$_2$)$_{1-6}$—NR$^{5a}$C(=NR$^{5a}$)NR$^{5a}_2$. In some embodiments, R$^5$ is —(CH$_2$)$_{2-4}$—NR$^{5a}_2$ or —(CH$_2$)$_{2-4}$—NR$^{5a}$C(=NR$^{5a}$)NR$^{5a}_2$. In some embodiments, each R$^{5a}$ is independently hydrogen or methyl. In some embodiments, each R$^{5a}$ is hydrogen. In some embodiments, when R$^5$ is —((C$_1$-C$_6$)alkylene)-NR$^{5a}$C(=NR$^{5a}$)NR$^{5a}_2$, all of the R$^{5a}$ groups are hydrogen, or only one of the R$^{5a}$ groups is (C$_1$-C$_6$)alkyl, e.g., methyl.

In some embodiments, R$^5$ is —(CH$_2$)$_2$—NH$_2$, —(CH$_2$)$_3$—NH$_2$, —(CH$_2$)$_4$—NH$_2$ or —(CH$_2$)$_3$—NHC(=NH)NH$_2$. In some embodiments, R$^5$ is —(CH$_2$)$_3$—NHC(=NH)NH$_2$.

In some embodiments, therefore, the amino acid having the carbon atom numbered 17 as its α-carbon atom (i.e., with R$^5$ as its side-chain) can be, e.g., alanine, arginine, 2,4-diaminobutyric acid, lysine or ornithine.

In some embodiments, R$^7$ can be (C$_1$-C$_6$)alkyl, e.g., (C$_1$-C$_4$)alkyl. R$^7$ can be, e.g., methyl, ethyl, n-propyl, isopropyl, isobutyl, sec-butyl, tert-butyl, neopentyl or n-hexyl.

In some embodiments, R$^7$ can be unsubstituted or substituted cycloalkyl, e.g., (C$_3$-C$_{12}$)cycloalkyl, e.g., (C$_5$-C$_7$)cycloalkyl or (C$_6$)cycloalkyl. R$^7$ can be, e.g., cyclopropyl, cyclobutyl, cyclopentyl, cyclohexyl or cycloheptyl. In some embodiments, the cycloalkyl can be unsubstituted. In some embodiments, the cycloalkyl can be substituted. When R$^7$ is substituted cycloalkyl, the cycloalkyl can be substituted, e.g., by 1, 2 or 3 substituents independently selected from (C$_1$-C$_6$)alkyl, (C$_2$-C$_6$)alkenyl, (C$_2$-C$_6$)alkynyl, halogen, (C$_1$-C$_6$)haloalkyl, —OR$^{7a}$ and oxo, wherein each R$^{7a}$ is independently selected from hydrogen and (C$_1$-C$_6$)alkyl, e.g., methyl, ethyl, n-propyl, isopropyl, isobutyl, sec-butyl, tert-butyl, neopentyl or n-hexyl.

In some embodiments, R$^7$ can be unsubstituted or substituted aryl (Ar$^7$), e.g., unsubstituted or substituted phenyl. When the aryl is substituted, the aryl, e.g., phenyl, can be substituted, e.g., by 1, 2 or 3 substituents independently selected from (C$_1$-C$_6$)alkyl, (C$_2$-C$_6$)alkenyl, (C$_2$-C$_6$)alkynyl, halogen, (C$_1$-C$_6$)haloalkyl, —CN, —NO$_2$, —OR$^{7a}$, —$NR^{7a}_2$ and —$NR^{7a}C(=O)R^{7a}$, wherein each $R^{7a}$ is independently selected from hydrogen and $(C_1-C_6)$alkyl, e.g., methyl, ethyl, n-propyl, isopropyl, isobutyl, sec-butyl, tert-butyl, neopentyl or n-hexyl.

In some embodiments, $R^7$ is $(C_1-C_6)$alkyl or $(C_4-C_7)$cycloalkyl. In some embodiments, $R^7$ is $(C_1-C_6)$alkyl. In some embodiments, $R^7$ is s-butyl.

In some embodiments, therefore, the amino acid having the carbon atom numbered 3 as its α-carbon atom (i.e., with $R^7$ as its side-chain) can be, e.g., alanine, leucine, isoleucine or valine.

$R^8$ can be $NH_2$ or OH. In some embodiments, $R^8$ is —$NH_2$. In some embodiments, $R^8$ is —OH. In some embodiments, therefore, the acid having the carbon atom numbered 1 as its α-carbon atom can be, e.g., cysteine or (R)-2-hydroxy-3-mercaptopropanoic acid.

In some embodiments, $R^{10}$ is selected from —$((C_1-C_6)$alkylene)-$OR^{10a}$ and —$((C_1-C_6)$alkylene)-$C(=O)NR^{10a}_2$. The $(C_1-C_6)$alkylene chains can have 1, 2, 3, 4, 5 or 6 carbon atoms and can be composed of methylene groups. For example, $R^{10}$ can be of the formula —$(CH_2)_{1-6}$—$C(=O)NR^{10a}_2$, e.g., —$(CH_2)_{1-6}$—$C(=O)NR^{10a}_2$. Each $R^{10a}$ is independently selected from hydrogen and $(C_1-C_6)$alkyl, e.g., methyl. In some embodiments, each $R^{10a}$ is hydrogen.

In some embodiments, $R^{10}$ is $Ar^{10}$—$CH_2$—. In some embodiments, $Ar^{10}$ is unsubstituted heteroaryl. In some embodiments, $Ar^{10}$ is substituted heteroaryl. In some embodiments, when $Ar^{10}$ is substituted, the heteroaryl is substituted, e.g., by 1, 2 or 3 substituents selected from $(C_1-C_6)$alkyl, $(C_2-C_6)$alkenyl, $(C_2-C_6)$alkynyl, halogen, $(C_1-C_6)$haloalkyl, —CN, —$NO_2$, —$OR^{10b}$, —$NR^{10b}_2$ and —$NR^{10b}C(=O)R^{10b}$. Each $R^{10b}$ is independently selected from hydrogen and $(C_1-C_6)$alkyl, e.g., methyl. In some embodiments, $Ar^{10}$ is heteroaryl, e.g., unsubstituted heteroaryl, and can be, e.g., pyridyl, pyrazinyl, pyrimidinyl, pyridazinyl, thienyl, furyl, pyrrolyl, imidazolyl, thiazolyl, oxazolyl, pyrazolyl, pyrazolyl, isothiazolyl, triazolyl, tetrazolyl, thiadiazolyl, oxadiazolyl, indolyl, indolinyl, quinolyl, isoquinolyl, benzofuryl, benzothienyl, benzoxazolyl, benzthiazolyl or benzimidazolyl. In some embodiments, $Ar^{10}$ is pyridyl, e.g., 3-pyridyl.

In some embodiments, $R^{10}$ is 1-hydroxyethyl, —$(CH_2)_2$—$C(=O)NH_2$ or 3-pyridyl-$CH_2$—. In some embodiments, $R^{10}$ is —$(CH_2)_2$—$C(=O)NH_2$.

In some embodiments, therefore, the amino acid having the carbon atom numbered 13 as its α-carbon atom (i.e., with $R^{10}$ as its side-chain) can be, e.g., asparagine, glutamine, threonine or 3-pyridylalanine.

Ar can be unsubstituted or substituted aryl, e.g., unsubstituted or substituted phenyl. When Ar is substituted, the aryl, e.g., phenyl, can be substituted, e.g., by 1, 2 or 3 substituents independently selected from $(C_1-C_6)$alkyl, $(C_2-C_6)$alkenyl, $(C_2-C_6)$alkynyl, halogen, $(C_1-C_6)$haloalkyl, —CN, —$NO_2$, —$OR^{Ar}$, —$NR^{Ar}_2$ and —$NR^{Ar}C(=O)R^{Ar}$, wherein each $R^{Ar}$ is independently selected from hydrogen and $(C_1-C_6)$alkyl, e.g., methyl, ethyl, n-propyl, isopropyl, isobutyl, sec-butyl, tert-butyl, neopentyl or n-hexyl. In some embodiments, Ar is phenyl or substituted phenyl. In some embodiments, Ar is phenyl.

In some embodiments, therefore, the amino acid having the carbon atom numbered 2 as its α-carbon atom (i.e., with —$CH_2Ar$ as its side-chain) can be, e.g., phenylalanine.

In some embodiments, each X is NH and each Y is C=O. In other embodiments, each X is C=O and each Y is NH.

m can be 0, 1, 2, 3, 4 or 5. In some embodiments, m is 0, 1, 2, 3 or 4. In some embodiments, m is 1. In some embodiments, m is 3.

o can be 1 or 2. In some embodiments, o is 1. In some embodiments, o is 2.

p is 1, 2 or 3. In some embodiments, p is 1. In some embodiments, p is 2. In some embodiments, p is 3.

In some embodiments, therefore, the amino acid having the carbon atom numbered 4 as its α-carbon atom (i.e., with $(CH_2)_p(C=O)NH_2$ as its side-chain) can be, e.g., asparagine, glutamine or homoglutamine.

In some embodiments, Q is $Q^1$. n can be any of 0, 1, 2, 3 or 4. r can be any of 0, 1, 2, 3, 4, 5 or 6. In some embodiments, when Q is $Q^1$, n is 1. In some embodiments, when Q is $Q^1$, n is 2. In some embodiments, when Q is $Q^1$, n is 3. In some embodiments, when Q is $Q^1$, $R^6$ is hydrogen or —$C(=NR^{6a})NR^{6a}_2$. Each $R^{6a}$ is independently hydrogen or $(C_1-C_6)$alkyl, e.g., methyl. In some embodiments, each $R^{6a}$ is hydrogen or methyl. In some embodiments, at least two of $R^{6a}$ are hydrogen. In some embodiments, each $R^{6a}$ is hydrogen. In some embodiments, when Q is $Q^1$, $R^6$ is hydrogen or —$C(=NH)NH_2$.

In some embodiments, when Q is $Q^1$, $Q^1$ is $^a$—$NH(CH_2)_4CH(NH_2)$—$C(=O)$—$^b$, $^a$—$NH(CH_2)_4CH(NHC(=NH)NH_2)$—$C(=O)$—$^b$ or $^a$—$C(=O)(CH_2)_2CH(NH_2)$—$C(=O)$—$^b$. In some embodiments, when Q is $Q^1$, $Q^1$ is $^a$—$NH(CH_2)_4C^{(S)}H(NH_2)$—$C(=O)$—$^b$, $^a$—$NH(CH_2)_4C^{(S)}H(NHC(=NH)NH_2)$—$C(=O)$—$^b$ or $^a$—$C(=O)(CH_2)_2C^{(S)}H(NH_2)$—$C(=O)$—$^b$ or $^a$—$C(=O)(CH_2)_2C^{(R)}H(NH_2)$—$C(=O)$—$^b$.

In some embodiments, Q is $Q^2$. n can be any of 0, 1, 2, 3 or 4. In some embodiments, when Q is $Q^2$, n is 0. In some embodiments, when Q is $Q^2$, n is 1. In some embodiments, when Q is $Q^2$, n is 2. In some embodiments, when Q is $Q^2$, n is 3.

In some embodiments, when Q is $Q^2$, $Q^2$ is $^a$—$NH(CH_2)_4$—$^b$, $^a$—$NH(CH_2)_5$—$^b$, $^a$—$NH(CH_2)_6$—$^b$, $^a$—$C(=O)$—$(CH_2)_3$—$^b$ or $^a$—$C(=O)$—$(CH_2)_5$—$^b$.

In some embodiments, Q is $Q^3$. n can be any of 0, 1, 2, 3 or 4. r can be any of 0, 1, 2, 3, 4, 5 or 6. In some embodiments, when Q is $Q^3$, n is 3. In some embodiments, when Q is $Q^3$, r is 0. In some embodiments, when Q is $Q^3$, r is 3. In some embodiments, when Q is $Q^3$, $R^6$ is hydrogen or —$C(=NR^{6a})NR^{6a}_2$. Each $R^{6a}$ is independently hydrogen or $(C_1-C_6)$alkyl, e.g., methyl. In some embodiments, each $R^{6a}$ is hydrogen or methyl. In some embodiments, at least two of $R^{6a}$ are hydrogen. In some embodiments, each $R^{6a}$ is hydrogen. In some embodiments, when Q is $Q^3$, $R^6$ is hydrogen or —$C(=NH)NH_2$.

In $Q^3$, in some embodiments, $R^9$ can be $(C_1-C_6)$alkyl. e.g., $(C_1-C_7)$alkyl or $(C_1-C_6)$alkyl. $R^9$ can be, e.g., methyl, ethyl, n-propyl, isobutyl, sec-butyl, tert-butyl, neopentyl, n-hexyl or n-heptyl.

In some embodiments, $R^9$ can be $(C_1-C_6)$haloalkyl, —$((C_1-C_6)$alkylene)-$OR^{9a}$, —$((C_1-C_6)$alkylene)-$NR^{9a}_2$, —$((C_1-C_6)$alkylene)-$SR^{9a}$, —$((C_1-C_6)$alkylene)-$C(=O)OR^{9a}_2$, —$((C_1-C_6)$alkylene)-$C(=O)NR^{9a}_2$, —$((C_1-C_6)$alkylene)-$C(=NR^{9a})NR^{9a}_2$, —$((C_1-C_6)$alkylene)-$OC(=O)R^{9a}$, —$((C_1-C_6)$alkylene)-$OC(=O)OR^{9a}$, —$((C_1-C_6)$alkylene)-$OC(=O)NR^{9a}_2$, —$((C_1-C_6)$alkylene)-$NR^{9a}C(=O)R^{9b}$, —$((C_1-C_6)$alkylene)-$NR^{9a}C(=O)OR^{9a}$, —$((C_1-C_6)$alkylene)-$NR^{9a}C(=O)NR^{9a}_2$ or —$((C_1-C_6)$alkylene)-$NR^{9a}C(=NR^{9a})NR^{9a}_2$. The $(C_1-C_6)$alkylene chains can have 1, 2, 3, 4, 5 or 6 carbon atoms and can be composed of methylene groups. For example, $R^9$ can be of the formula —$(CH_2)_{1-6}$—$OR^{9a}$, —$(CH_2)_{16}$—$NR^{9a}_2$, —$(CH_2)_{16}$—$SR^{9a}$, —$(CH_2)_{1-6}$—$C(=O)OR^{9a}_2$, —$(CH_2)_{1-6}$—$C(=O)NR^{9a}_2$, —$(CH_2)_{1-6}$—$C(=NR^{9a})NR^{9a}_2$, —$(CH_2)_{1-6}$—$OC(=O)R^{9b}$, —$(CH_2)_{1-6}$—$OC(=O)OR^{9a}$, —$(CH_2)_{1-6}$—$OC(=O)NR^{9a}_2$, —$(CH_2)_{1-6}$—$NR^{9a}C(=O)R^{9b}$, —$(CH_2)_{1-6}$—$NR^{9a}C(=O)$ $OR^{9a}$, $-(CH_2)_{1-6}-NR^{9a}C(=O)NR^{9a}_2$ or $-(CH_2)_{1-6}-NR^{9a}C(=NR^{9a})NR^{9a}_2$. In some embodiments, $R^9$ can be $-((C_1-C_6)alkylene)-C(=O)NR^{9a}_2$ or $-((C_1-C_6)alkylene)-NR^{9a}C(=O)R^{9b}$, e.g., $-(CH_2)_{1-6}-NR^{9a}_2$ or $-(CH_2)_{1-6}-NR^{9a}C(=O)R^{9b}$. Each $R^{9a}$ is independently selected from hydrogen and $(C_1-C_6)$alkyl, e.g., methyl. In some embodiments, each $R^{9a}$ is hydrogen. Each $R^{9b}$ is independently selected from hydrogen and $(C_1-C_{10})$alkyl, e.g., $(C_1-C_6)$alkyl, e.g., methyl or n-hexyl. In some embodiments, $R^9$ can be, e.g., $-CH_2-NH_2$, $-(CH_2)_2-NH_2$, $-(CH_2)_3-NH_2$ or $-(CH_2)_4-NH_2$, $-CH_2-NHC(=O)R^{9b}$, $-(CH_2)_2-NHC(=O)R^{9b}$, $-(CH_2)_3-NHC(=O)R^{9b}$ or $-(CH_2)_4-NHC(=O)R^{9b}$; or each formula $R^{9b}$ can be, for example, methyl, ethyl, n-propyl, n-butyl, n-pentyl or n-hexyl. In some embodiments, $R^9$ can be, e.g., $-(CH_2)_4-NH_2$, $-(CH_2)_4-NHAc$ or $-(CH_2)_4-NHheptanoyl$.

In some embodiments, $R^9$ can be $Ar^9$ or $-((C_1-C_6)alkylene)-Ar^9$. The $(C_1-C_6)$alkylene chains can have 1, 2, 3, 4, 5 or 6 carbon atoms and can be composed of methylene groups. For example, $R^9$ can be of the formula $-(CH_2)_{1-6}-Ar^9$, e.g., $-CH_2-Ar^9$. $Ar^9$ can be unsubstituted or substituted aryl, e.g. phenyl, or unsubstituted or substituted heteroaryl. In some embodiments, when $Ar^9$ is substituted, the aryl, e.g., phenyl, or heteroaryl can be substituted, e.g., by 1, 2 or 3 substituents independently selected from $(C_1-C_6)$alkyl, $(C_2-C_6)$alkenyl, $(C_2-C_6)$alkynyl, halogen, $(C_1-C_6)$haloalkyl, $-CN$, $-NO_2$, $-OR^{9c}$, $-NR^{9c}_2$ and $-NR^{9c}C(=O)R^{9c}$, wherein each $R^{9c}$ is independently selected from hydrogen and $(C_1-C_6)$alkyl, e.g., methyl, ethyl, n-propyl, isopropyl, isobutyl, sec-butyl, tert-butyl, neopentyl or n-hexyl. In some embodiments, when $Ar^9$ is heteroaryl, e.g., unsubstituted heteroaryl, $Ar^9$ can be, e.g., pyridyl, pyrazinyl, pyrimidinyl, pyridazinyl, thienyl, furyl, pyrrolyl, imidazolyl, thiazolyl, oxazolyl, pyrazolyl, pyrazolyl, isothiazolyl, triazolyl, tetrazolyl, thiadiazolyl, oxadiazolyl, indolyl, indolinyl, quinolyl, isoquinolyl, benzofuryl, benzothienyl, benzoxazolyl, benzthiazolyl or benzimidazolyl.

In some embodiments, $Q^3$ is $^a-NH(CH_2)_4-C(=O)-NH-(CH_2)_4CH(NH_2)-C(=O)-^b$, $^a-NHCH((CH_2)_4NH_2)-C(=O)-NH-(CH_2)_4CH(NH_2)-C(=O)-^b$, $^a-NHCH((CH_2)_4NHAc)-C(=O)-NH-(CH_2)_4CH(NH_2)-C(=O)-^b$ or $^a-NHCH((CH_2)_4NHHeptanoyl)-C(=O)-NH-(CH_2)_4CH(NH_2)-C(=O)-^b$. In some embodiments, $Q^3$ is $^a-NH(CH_2)_4-C(=O)-NH-(CH_2)_4C^{(S)}H(NH_2)-C(=O)-^b$, $^a-NHC^{(S)}H((CH_2)_4NH_2)-C(=O)-NH-(CH_2)_4C^{(S)}H(NH_2)-C(=O)-^b$, $^a-NHC^{(S)}H((CH_2)_4NHAc)-C(=O)-NH-(CH_2)_4C^{(S)}H(NH_2)-C(=O)-^b$, $^a-NHC^{(S)}H((CH_2)_4NHAc)-C(=O)-NH-(CH_2)_4C^{(R)}H(NH_2)-C(=O)-^b$ or $^a-NHC^{(S)}H((CH_2)_4NHHeptanoyl)-C(=O)-NH-(CH_2)_4C^{(S)}H(NH_2)-C(=O)-^b$.

In some embodiments, Q is $Q^4$. n can be any of 0, 1, 2, 3 or 4. r can be any of 0, 1, 2, 3, 4, 5 or 6. In some embodiments, when Q is $Q^4$, n is 1. In some embodiments, when Q is $Q^4$, n is 2. In some embodiments, when Q is $Q^4$, n is 3. In some embodiments, when Q is $Q^4$, r is 1. In some embodiments, when Q is $Q^4$, r is 2. In some embodiments, when Q is $Q^4$, r is 3.

In some embodiments, when Q is $Q^4$, $Q^4$ can be $^a-NH-(CH_2)_2-C(=O)-NH-(CH_2)_5-^b$, $^a-NH-(CH_2)_4-C(=O)-NH-(CH_2)_6-^b$, $^a-C(=O)-(CH_2)_2-C(=O)-NH-(CH_2)_6-^b$ or $^a-C(=O)-(CH_2)_3-C(=O)-NH-(CH_2)_4-^b$.

The following peptidic partial V1a agonist compounds can illustrate the generic structure provided in formula (I). In the following sequences, with reference to structural formula (1), the bottom line lists amino acids of the peptide fragment containing the carbon atoms that are labeled 10-18 in formula (I) and the bottom line lists amino acids of the peptide fragment containing carbon atoms that are labeled 1-9 in formula (I), together with the group Q. The link between Q and the peptide fragment containing carbons atoms 1-9 (i.e., bond "b" in formula (I)) is indicated by a vertical line.

Compound No. 1

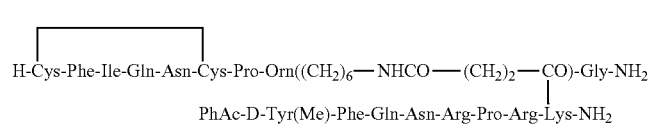

Compound No. 2

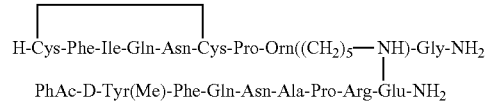

Compound No. 3

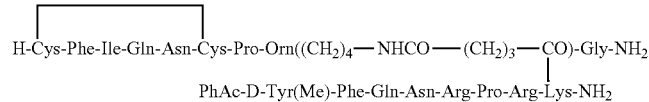

Compound No. 4

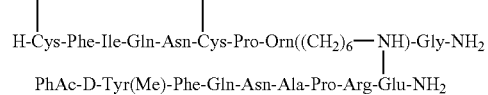

Compound No. 5

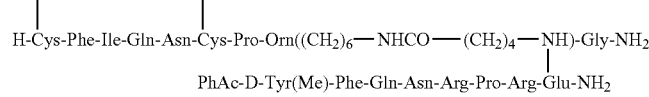

-continued
Compound No. 6
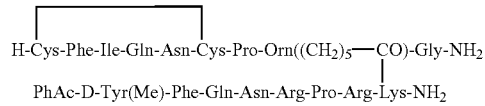
Compound No. 7
Compound No. 8
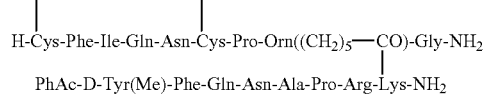
Compound No. 9
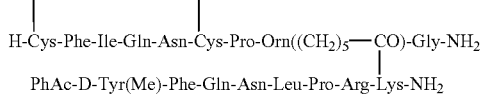
Compound No. 10
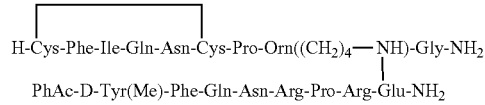
Compound No. 11
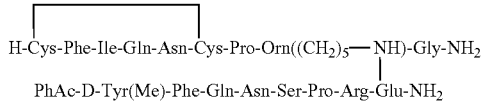
Compound No. 12
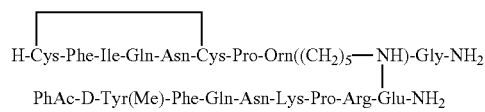
Compound No. 13
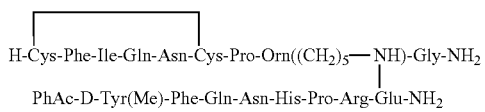
Compound No. 14
Compound No. 15
Compound No. 16
Compound No. 17
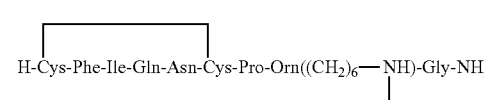
Compound No. 18
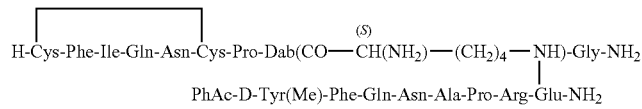
Compound No. 19
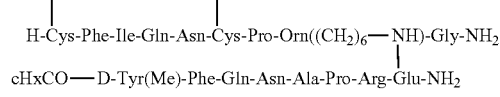
Compound No. 20
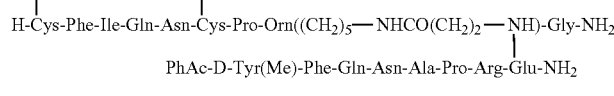
Compound No. 21
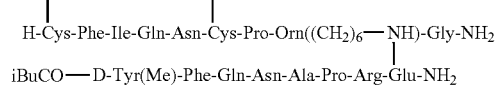
Compound No. 22
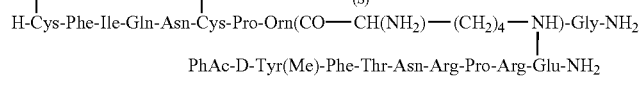
Compound No. 23
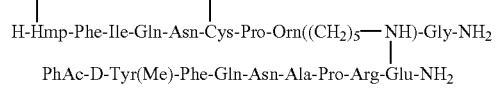

Compound No. 24

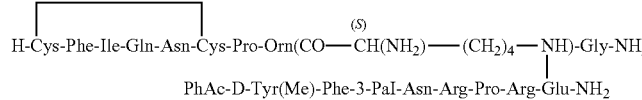
PhAc-D-Tyr(Me)-Phe-3-PaI-Asn-Arg-Pro-Arg-Glu-NH₂

Compound No. 25

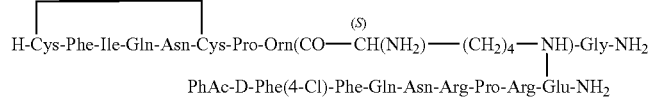
PhAc-D-Phe(4-Cl)-Phe-Gln-Asn-Arg-Pro-Arg-Glu-NH₂

Compound No. 26

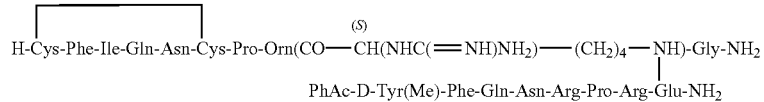
PhAc-D-Tyr(Me)-Phe-Gln-Asn-Arg-Pro-Arg-Glu-NH₂

Compound No. 27

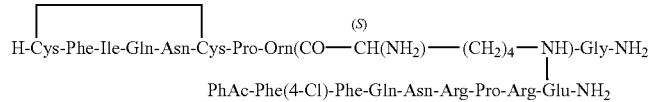
PhAc-Phe(4-Cl)-Phe-Gln-Asn-Arg-Pro-Arg-Glu-NH₂

Compound No. 28

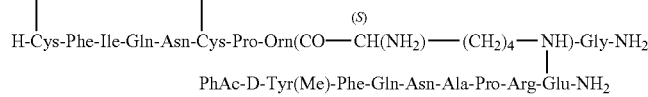
PhAc-D-Tyr(Me)-Phe-Gln-Asn-Ala-Pro-Arg-Glu-NH₂

Compound No. 29

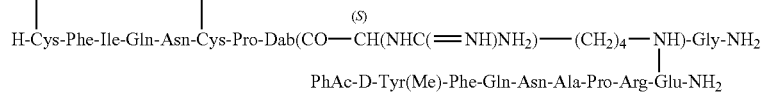
PhAc-D-Tyr(Me)-Phe-Gln-Asn-Ala-Pro-Arg-Glu-NH₂

Compound No. 30

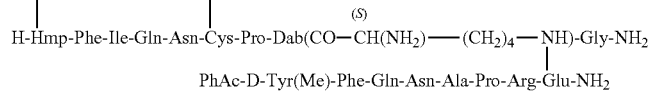
PhAc-D-Tyr(Me)-Phe-Gln-Asn-Ala-Pro-Arg-Glu-NH₂

Compound No. 31

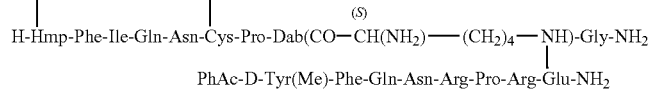
PhAc-D-Tyr(Me)-Phe-Gln-Asn-Arg-Pro-Arg-Glu-NH₂

Compound No. 32

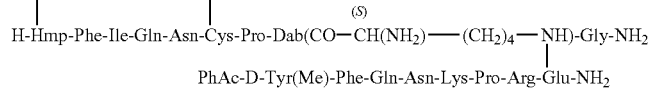
PhAc-D-Tyr(Me)-Phe-Gln-Asn-Lys-Pro-Arg-Glu-NH₂

Compound No. 33

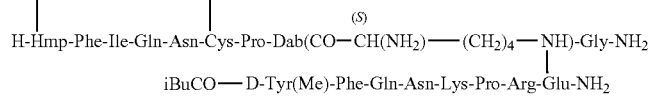
iBuCO—D-Tyr(Me)-Phe-Gln-Asn-Lys-Pro-Arg-Glu-NH₂

Compound No. 35

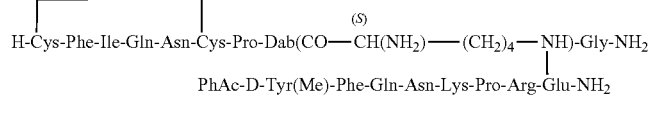
PhAc-D-Tyr(Me)-Phe-Gln-Asn-Lys-Pro-Arg-Glu-NH₂

Compound No. 36

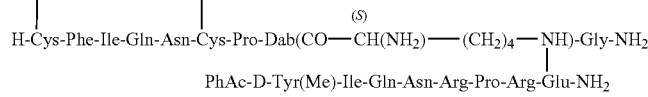
PhAc-D-Tyr(Me)-Ile-Gln-Asn-Arg-Pro-Arg-Glu-NH₂

Compound No. 37

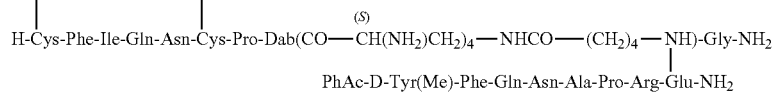
PhAc-D-Tyr(Me)-Phe-Gln-Asn-Ala-Pro-Arg-Glu-NH₂

Compound No. 38
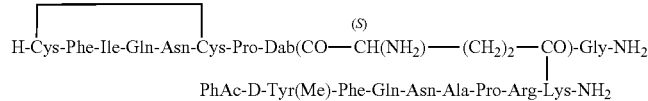
Compound No. 39
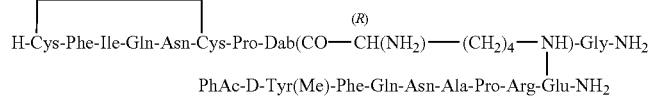
Compound No. 41
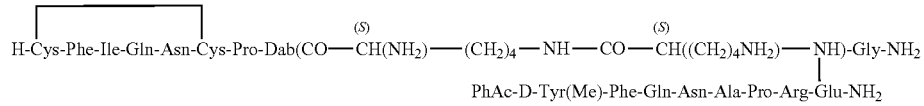
Compound No. 42
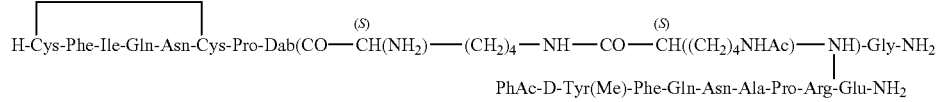
Compound No. 43
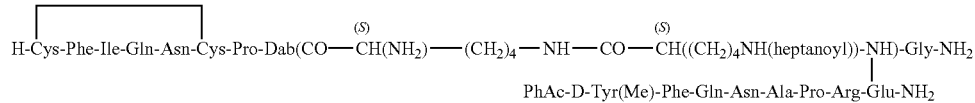
Compound No. 44
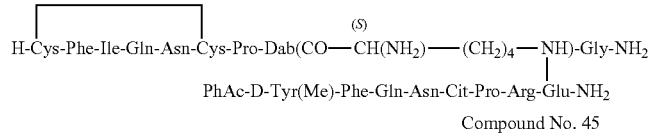
Compound No. 45          Compound No. 46
Compound No. 47
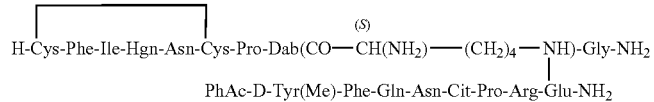
Compound No. 48
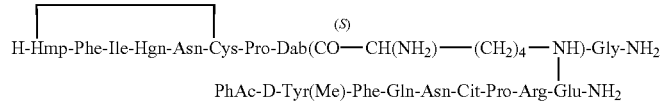
Compound No. 49
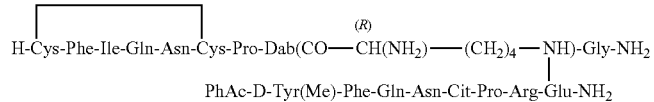
Compound No. 50
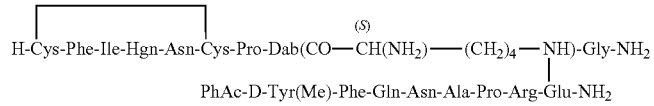
Compound No. 51
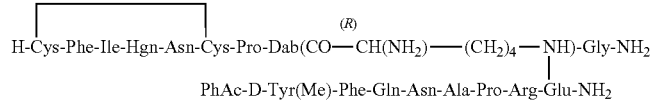
Compound No. 52
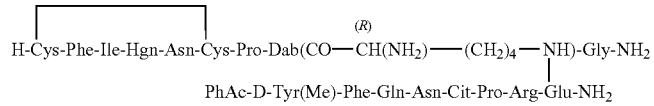

Compound No. 53
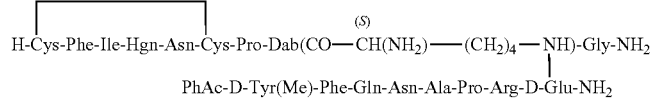
Compound No. 54
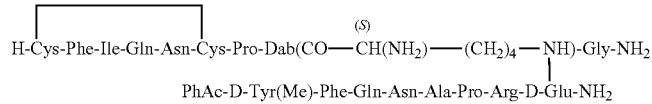
Compound No. 55
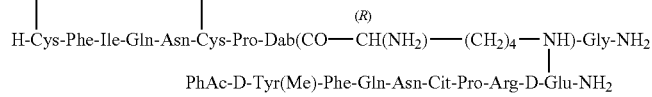
Compound No. 56
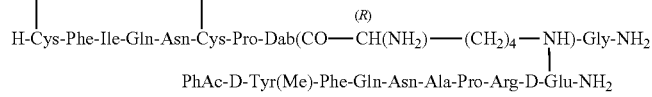
Compound No. 57
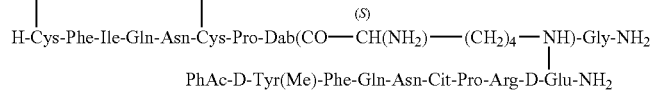
Compound No. 58
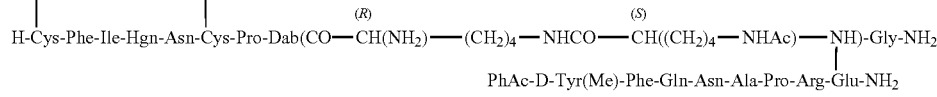
Compound No. 59
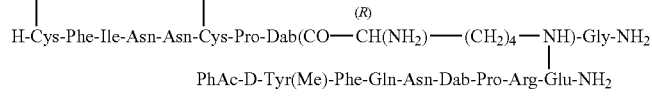
Compound No. 60
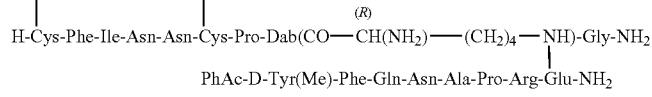
Compound No. 61
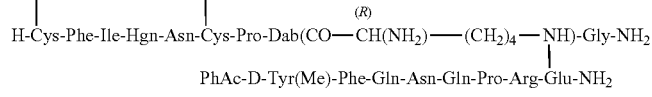
Compound No. 62
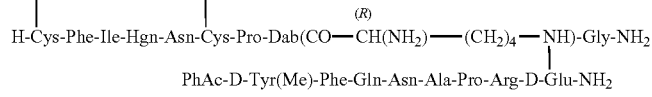
Compound No. 63
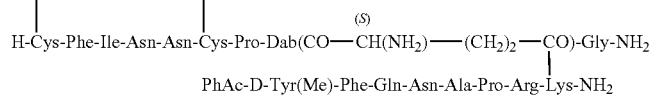
Compound No. 64
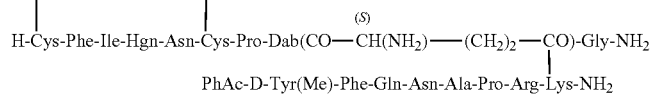
Compound No. 65
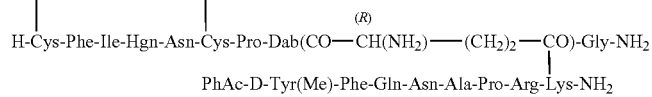

-continued
Compound No. 66
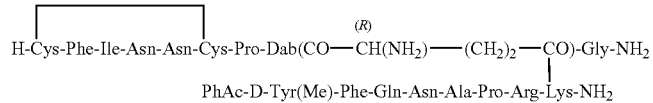
The following are molecular structures of particular exemplified compounds.
Compound No. 18 (below)
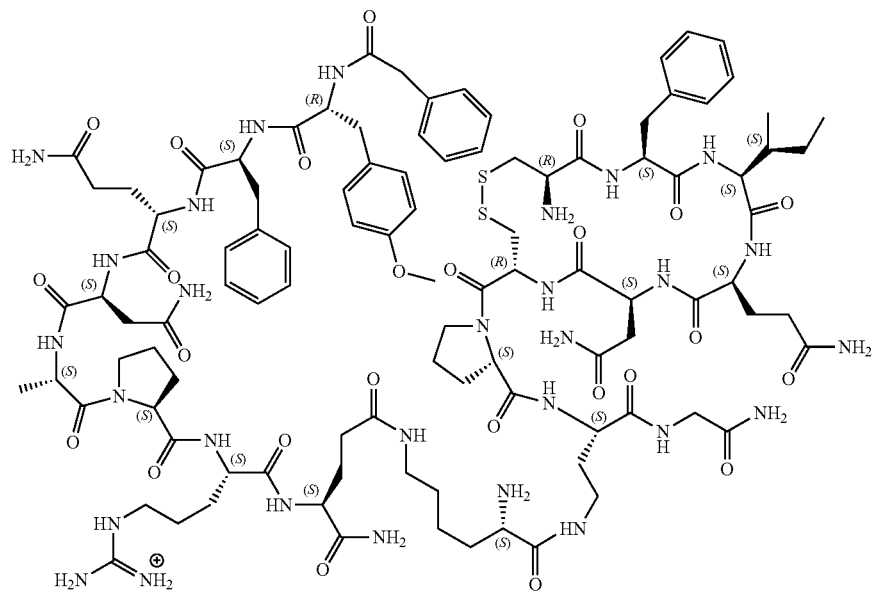
Compound No. 39 (below)
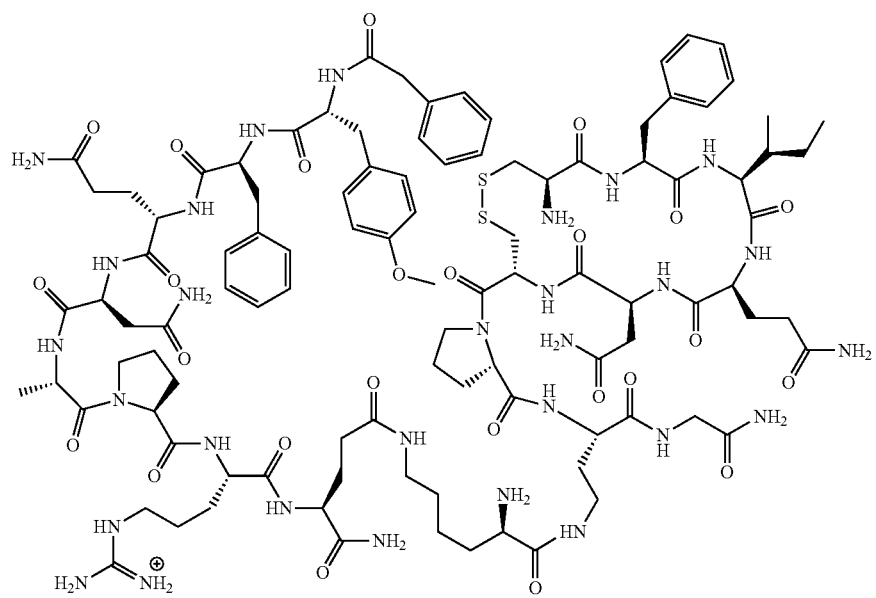

Compound No. 41 (below)
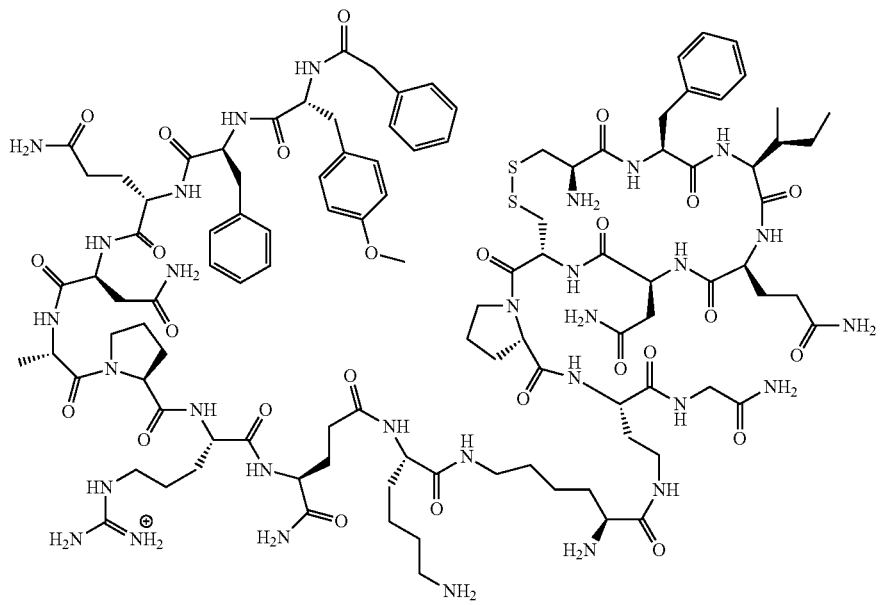
Compound No. 42 (below)
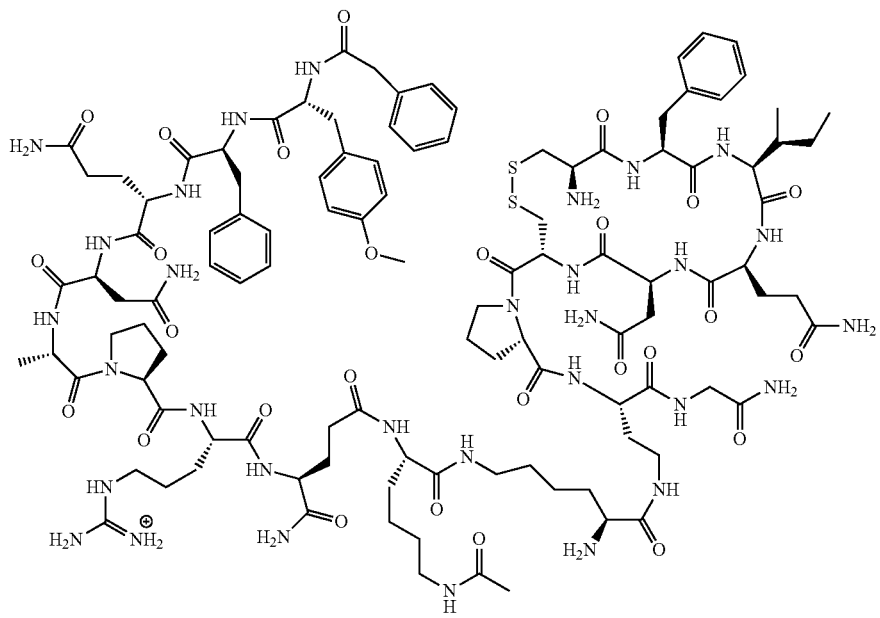

-continued
Compound No. 47 (below)
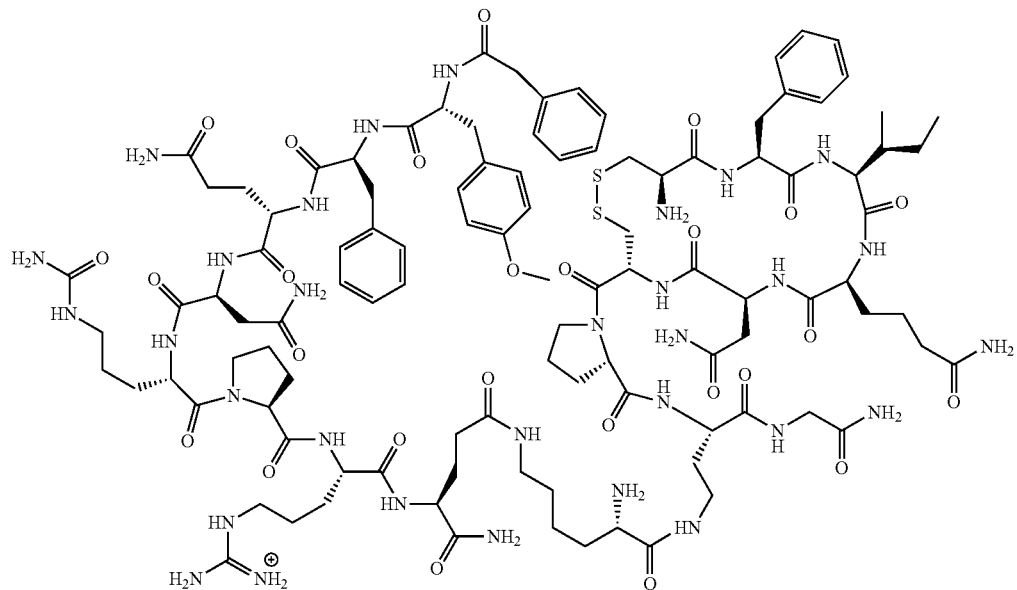
Compound No. 48 (below)
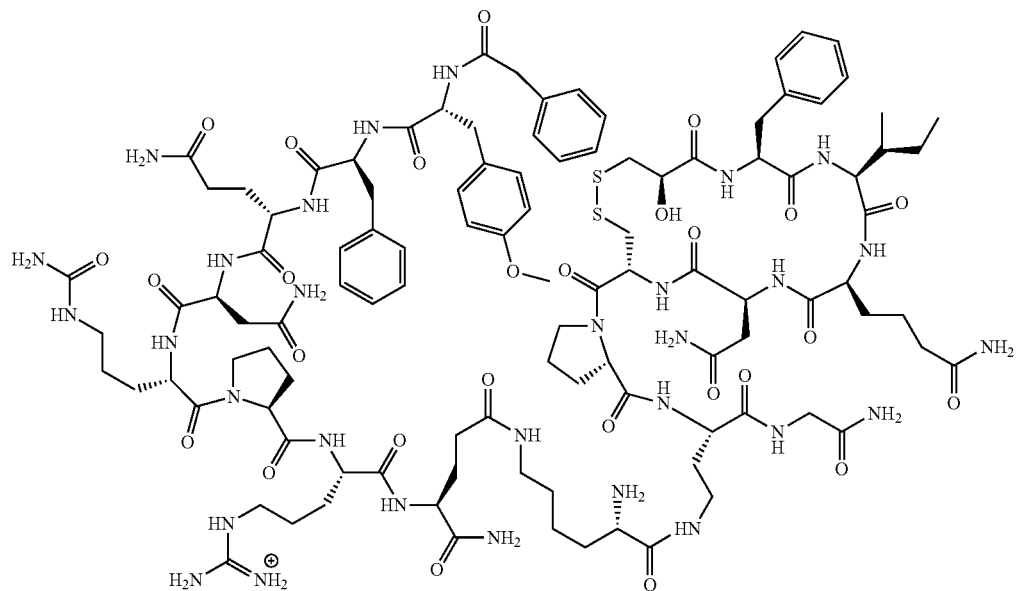

Compound No. 49 (below)
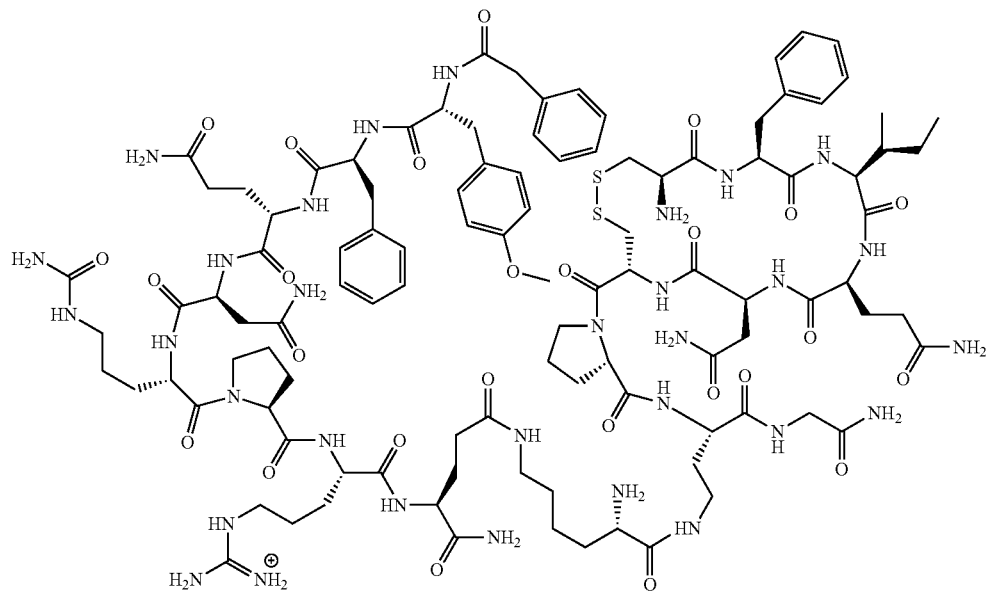
Compound No. 50 (below)
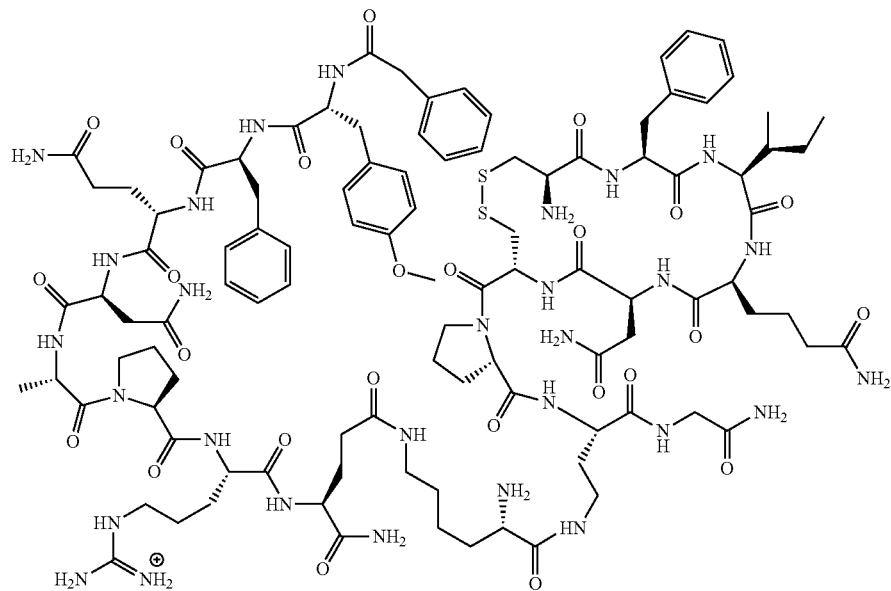

Compound No. 54 (below)

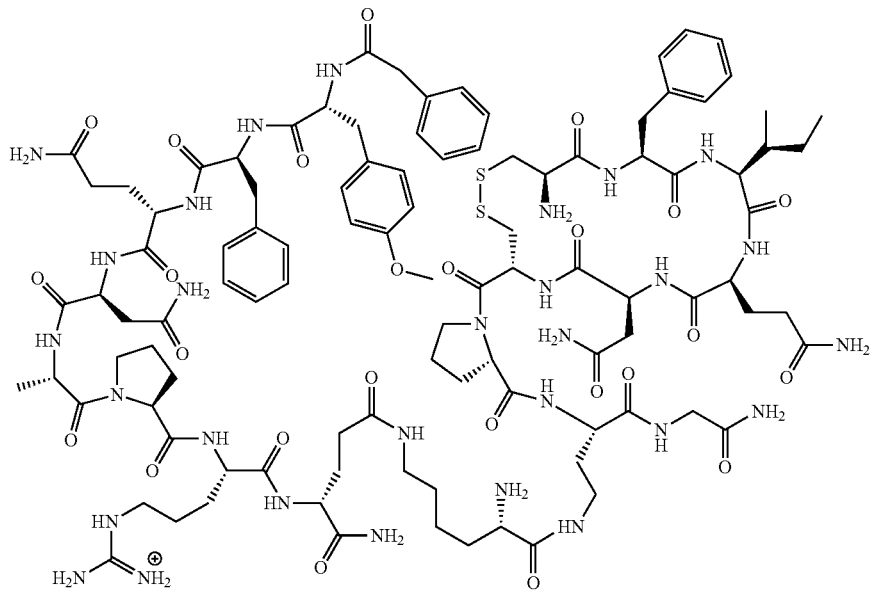

Compound No. 55 (below)

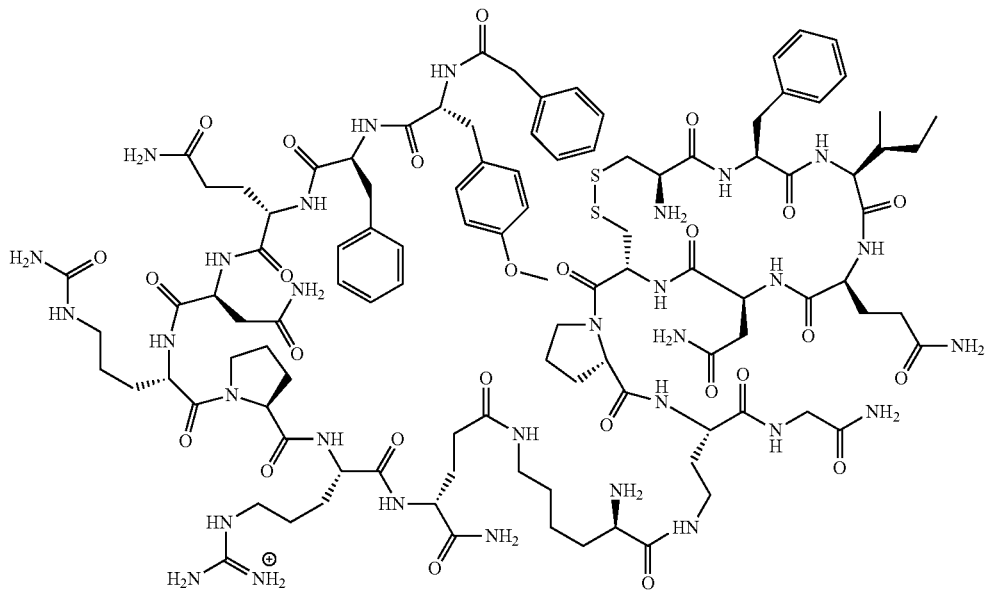

III. SYNTHESIS

In general, the methods of peptide synthesis are applicable to the synthesis of the compounds of formula (I). Methods of peptide synthesis are well-developed in the art and typically use protected amino acids, typically protected with a carbamate group (e.g., t-butyloxycarbonyl ("BOC") or fluorenylmethoxycarbonyl (Fmoc). In a typical process, the protected amino acid is coupled to a free amino group of a growing peptide chain to give a peptide extended by an additional amino acid unit. The amino group of the new terminal amino acid of the growing peptide chain is then deprotected, and is available for further coupling reactions. Due to the well-developed methods available for peptide synthesis, methods that are suitable for synthesis of the compounds of formula (I) will be apparent to one skilled in the art from the structure of such compounds. Syntheses of particular compounds are described in the Examples, and the methods described can be adapted to additional compounds within the scope of formula (I), e.g., by substituting appropriate amino acid derivatives as necessary.

Due to the biological importance of peptides and peptide analogues, a wide variety of amino acids is commercially available or known in the art. In addition, numerous methods of making such compounds are known in the art. Therefore, the amino acids (as well as other intermediates) required to make compounds of formula (I) are commercially available, known in the art, or may be made by methods known in the art.

Methods of synthesizing amino acids and peptides are described, e.g., by: Benoiton, *Chemistry of Peptide Synthesis*, CRC Press, 2006; Hughes, et al., *Amino Acids, Peptides* and *Proteins in Organic Chemistry, Vol. 1, Origins and Synthesis of Amino Acids*, Wiley-VCH 2009; Hughes, et al., *Amino Acids, Peptides and Proteins in Organic Chemistry, Vol. 2. Modified Amino Acids, Organocatalysis and Enzymes*; Wiley-VCH 2010; Hughes, et al., *Amino Acids, Peptides and Proteins in Organic Chemistry Vol. 3: Building Blocks, Catalysis and Coupling Chemistry*, Wiley-VCH 2011; Hughes, et al., *Amino Acids, Peptides and Proteins in Organic Chemistry, Vol. 4: Amino Acids, Peptides and Proteins in Organic Chemistry, Protection Reactions, Medicinal Chemistry, Combinatorial Synthesis*, Wiley-VCH 2011; *Amino Acids, Peptides and Proteins in Organic Chemistry, Vol. 5: Amino Acids, Peptides and Proteins in Organic Chemistry, Analysis and Function of Amino Acids and Peptides*, Wiley-VCH 2011; Howl, et al., *Peptide Synthesis and Applications (Methods in Molecular Biology Vol. 298)*, Humana Press, 2010; Jones, *Amino Acid and Peptide Synthesis*, 2nd edn., Oxford University Press, 2002; Jones, *The Chemical Synthesis of Peptides (International Series of Monographs on Chemistry)*, Oxford University Press, 1994; Pennington, et al., *Peptide Synthesis Protocols (Methods in Molecular Biology Vol. 35)*, Humana Press, 1994; Sewald, et al., *Peptides: Chemistry and Biology*, Wiley-VCH, 2009; Williams, et al., *Chemical Approaches to the synthesis of Peptides and Proteins (New Directions in Organic & Biological Chemistry)*, CRC Press 1997.

IV. FORMULATION AND ADMINISTRATION

Compositions provided herein may comprise the partial V1a receptor agonists of formula (I) described herein, their salts, or any of the embodiments thereof. The compounds provided herein are particularly soluble at physiological pHs (e.g., about 6.8 to about 7.4) and can be prepared as relatively concentrated solutions for administration, particularly for subcutaneous injection. These compounds are well-tolerated in the body and do not tend to gel when administered subcutaneously at effective concentrations.

Generally, pharmaceutical compositions including such compounds and a suitable pharmaceutically acceptable excipient can be administered parenterally, e.g., intravenously, intraperitoneally, intramuscularly, subcutaneously, or the like. The pharmaceutical compositions will usually contain an effective amount of the compound in conjunction with a conventional, pharmaceutically-acceptable carrier or diluent. Usually, the dosage will be from about 1 micrograms to about 2.5 milligrams of the peptide per kilogram of the body weight of the host when given intravenously. The nature of these compounds may permit effective oral administration; however, oral dosages might be higher.

For parenteral administration, the compound may be formulated, e.g., as a sterile solution or suspension. The compounds may be formulated, e.g., as a sterile aqueous preparation that may be isotonic with the blood of the recipient. An aqueous preparation may be formulated, e.g., according to known methods using suitable dispersing agents, wetting agents, and/or suspending agents. Water, Ringer's solution, and isotonic sodium chloride solution are examples of suitable diluents. Sterile, fixed oils may be employed as a solvent or suspending system. Bland fixed oils, including synthetic mono- or di-glycerides, and fatty acids, such as oleic acid, may be used.

The amount of compound or composition to be administered will be determined by the responsible physician, taking into consideration all the relevant factors. In a preferred embodiment, the amount of compound or composition administered in each injection will be between about 0.001 mg to about 2.5 mg per Kg of body weight per day, with about 0.2 mg/Kg/day usually being sufficient.

The compounds, and compositions containing the compounds, could be given intravenously or subcutaneously, e.g., once, or chronically, to increase systemic vascular resistance and/or reduce splanchnic blood flow to treat any of the indications. In some embodiments, the compounds are administered by intravenous injection. A course of treatment may involve a single injection or repeated injections.

In general, dosing frequency can range from as infrequently as several times a week, up to several times per day. In general, duration of therapy can range from as short as about a few days or a week, up to continuously. When treatment of the patient includes paracentesis, the course of treatment can comprise an injection immediately before the start of paracentesis and one or more (such as two or three) injections following the paracentesis and at least one, such as two, injections afterwards. The injections may be separated by a period of a few hours, such as a period of between 4 and 12 h, more preferably between 6 and 10 h. A course of treatment can comprise an injection before the start of paracentesis and follow-up injections 8 and 16 h later.

The compounds provided herein are often administered in the form of pharmaceutically acceptable, nontoxic salts, such as acid addition salts, or of metal complexes, e.g., with zinc, barium, calcium, magnesium, aluminum, or the like (which are considered as addition salts for purposes of this application), or of combinations of the two. Illustrative of such acid addition salts are hydrochloride, hydrobromide, sulfate, phosphate, nitrate, oxalate, fumarate, gluconate, tannate, pamoate, maleate, acetate, citrate, benzoate, succinate, alginate, malate, ascorbate, tartrate, and the like.

V. METHODS OF USE

Also provided herein are methods of treatment and methods of using the compounds and compositions described and provided herein, e.g., for the manufacture of medicinal products for therapeutic effect. The compounds, and compositions containing the compounds, are useful for treatment of, e.g., complications of cirrhosis, including bacterial peritonitis, HRS2 and refractory ascites.

Provided herein are compounds that have a reduced maximal efficacy at the V1a receptor such that the risk of excessive vasoconstriction is significantly reduced. The compounds are also useful, e.g., for treatment to increase blood pressure. These compounds are especially useful in the treatment of conditions where a modest increase in blood pressure is desirable, such as shock of hypovolemic (e.g., hemorrhagic) or vasodilatory (e.g., septic) origin, bleeding esophageal varices (BEV), hepatorenal syndrome (HRS), including type I and type II heptoarenal syndrome, cardiopulmonary resuscitation and anesthesia-induced hypotension. These compounds are also especially useful in the treatment of complications arising from cirrhosis, including spontaneous bacterial peritonitis, type II heptoarenal syndrome (HRS2) and refractory ascites. Refractory ascites refers to an inability to mobilize ascitic fluid and can be diagnosed by the following criteria: lack of response to maximal doses of diuretic for at least one week; diuretic-induced complications in the absence of other precipitating factors; early recurrence of ascites within 4 weeks of fluid mobilization; persistent ascites despite sodium restriction; mean weight loss less than 0.8 kg over 4 days despite maximal doses of diuretics; and urinary sodium excretion less than sodium intake (Siqueira, et al., *Gastroenterol. Hepatol.*, (N.Y.), 2009, 5(9), 647-656.)

The compounds described herein will also have clinical use in the treatment of orthostatic hypotension, paracentesis-induced circulatory dysfunction, acute hemorrhage, intraoperative blood loss and blood loss associated with burn debridement and blood loss associated with epistaxis.

Other conditions that can be treated with the compounds described herein include: hypertensive gastropathy bleeding; sepsis; severe sepsis; septic shock; hypotension, including prolonged and severe hypotension, and orthostatic hypotension and intradialytic hypotension; cardiac arrest; trauma-related blood loss; vasodilatory shock induced by cardio-pulmonary bypass; milrinone-induced vasodilatory shock in congestive heart failure; type I hepatorenal syndrome; type II hepatorenal syndrome; anaphylactic shock; cardiovascular instability induced by brain death; acute respiratory distress syndrome; acute lung injury; shock induced by metformin intoxication; shock induced by mitochondrial disease; shock induced by cyanide poisoning; shock induced by vascular leak syndrome induced by interleukin-2, another cytokine, denileukin diftitox or another immunotoxin, or by ovarian hyperstimulation syndrome; hypotension induced by end-stage renal disease; inflammatory bowel disease; reperfusion injury; infant respiratory distress syndrome; severe acute respiratory syndrome; ascites; vasodepressor syncope; vasovagal syncope, e.g., postural hypotension with syncope, or neurocardiogenic syncope; toxic shock syndrome; and idiopathic systemic capillary leak syndrome (Clarkson's disease).

These compounds also display an improved therapeutic index over therapy involving, e.g., terlipressin.

EXAMPLES

1. General Methods

Amino acid derivatives were purchased from commercial providers (Bachem, EMD Biosciences and Peptides International). Resins were purchased from commercial suppliers (PCAS BioMatrix Inc. and EMD Biosciences). All additional reagents, chemicals and solvents were purchased from Sigma-Aldrich and VWR.

Most of the compounds herein were synthesized by standard methods in solid phase peptide chemistry utilizing Fmoc methodology. The peptides were assembled either manually, automatically using a Protein Technologies Tribute Peptide Synthesizer or by combination of manual and automatic syntheses. If more convenient the compounds were assembled manually using combination of Boc and Fmoc strategies (e.g., compounds 26, 29).

Preparative HPLC was performed on a Waters Prep LC System using a PrepPack cartridge Delta-Pack C18, 300 Å, 15 μm, 47×300 mm at a flow rate of 100 mL/min and/or on a Phenomenex Luna C18 column, 100 Å, 5 μm, 30×100 mm at a flow rate of 40 mL/min. Analytical reverse phase HPLC was performed on an Agilent Technologies 1200rr series liquid chromatograph using an Agilent Zorbax C18 column, 1.8 μm, 4.6×110 mm at a flow rate of 1.5 mL/min. Final compound analyses were performed on an Agilent Technologies 1200 Series chromatograph by reverse phase HPLC on a Phenomenex Gemini 110 Å C18 column, 3 μm, 2×150 mm at a flow rate of 0.3 mL/min. Mass spectra were recorded on a MAT Finnigan LCQ electrospray mass spectrometer. Unless stated otherwise, all reactions were performed at room temperature. The following standard reference literature provides further guidance on general experimental set up, as well as on the availability of required starting material and reagents: Kates, et al., *Solid Phase Synthesis: A Practical Guide*, Marcel Dekker, New York, Basel, 2000; Greene, et al., *Protective Groups in Organic Synthesis*, John Wiley Sons Inc., $2^{nd}$ Edition, 1991; Stewart, et al., *Solid Phase Synthesis*, Pierce Chemical Company, 1984; Bisello, et al., *J. Biol. Chem.*, 1998, 273, 22498-22505; Merrifield, *J. Am. Chem. Soc.*, 1963, 85, 2149-2154; and Chang, et al., *Fmoc Solid Phase Peptide Synthesis: a Practical Approach*, Oxford University Press, Oxford, 2000. H-Rink-ChemMatrix resin (PCAS BioMatrix Inc., St-Jean-sur-Richelieu, Canada) was used as starting material for automatic synthesis and Fmoc-Rink-AM resin (EMD Biosciences, San Diego, Calif.) was used for manual synthesis.

The following protecting groups were utilized to protect the given amino acid side chain functional groups: Pbf (2,2,4,6,7-pentamethyldihydrobenzofuran-5-sulfonyl) for Arg; tBu (t-butyl) for Glu, Asp, Ser, Thr and Tyr; Trt (trityl) for Cys, His, Gln and Asn; Boc (t-butoxycarbonyl) group for Dab, Orn and Lys. The Mtt (4-methyltrityl) or ivDde (1-(4,4-dimethyl-2,6-dioxocyclohex-1-ylidene)3-methylbutyl) protecting groups were used in the side chain of the diamino acid residue of alpha amino acid 8 to provide an additional level of orthogonality for branching.

Peptides were prepared on solid support starting with residues 1-9 of the peptide shown in Formula (I), followed by the removal of the position 8 side chain orthogonal protecting group and the addition of the alpha amino acid 10-18 containing peptide fragment. The solid phase peptide synthesis was performed manually, automatically on the Tribute peptide synthesizer (Protein Technologies Inc., Tucson, Ariz.) or by a combination of the manual and automatic methods.

Couplings of Fmoc-protected amino acids on the Tribute synthesizer were mediated with HBTU/NMM in DMF except for cysteine derivatives that were coupled with DIC/HOBt in DMF. Single cycles of 30-60 min. with a 5-fold excess of activated Fmoc-protected amino acids were used during the synthesis. Removal of the Fmoc protecting group was monitored by UV. Multiple (up to 10 times, as needed) two-minute washes of the peptide resin with 20% piperidine in DMF were performed.

DIC/HOBt mediated couplings in DMF were employed for all amino acids in manual mode. Single cycles of at least 2 h with a 3-fold excess of activated Fmoc-protected amino acids were used during the synthesis. The completeness of couplings was assessed with the ninhydrin (Kaiser) test. Removal of the Fmoc protecting group was achieved with a single 30 min. wash of the peptide resin with 20% piperidine in DMF.

After the peptide fragment containing alpha carbons 1-9 was assembled the position 8 side chain protecting group was removed. Peptide resins protected with the Mtt group were treated with the HIPF/TFE/TIS/DCM 4/2/1/13 (v/v/v/v) cocktail (3 times for 1 h). To remove the ivDde protecting group the peptide resins were treated with 2% hydrazine/DMF (3 times for 10 min.). After the orthogonal protecting group was removed the remaining part (residues 10-18) of the peptide was assembled by adding each amino acid sequentially.

Upon completion of the peptide synthesis, the peptide resins were washed with DCM and dried in vacuo. The resins were treated with TFA/$H_2O$/TIS 96:2:2 (v/v/v) for 2 h to remove the side-chain protecting groups with concomitant cleavage of the peptide from the resin. The peptides were filtered, precipitated with diethyl ether and decanted. The precipitate was dissolved in 10 mL of neat TFA and the solution was subsequently poured into 200 mL of 10% acetonitrile in water. The linear peptide was oxidized with 0.1 M I$_2$/MeOH. The oxidizer solution was added dropwise until yellow color persisted. The excess of iodine was reduced with solid ascorbic acid. The pH was then adjusted to about 4 with concentrated ammonia. The solution obtained was loaded directly onto an HPLC prep column and eluted with a gradient of component B (see table below).

Each crude peptide was purified with buffer system P. The fractions with a purity exceeding 93%, determined by reverse-phase analytical HPLC, were pooled and reloaded onto the column and eluted with buffer T to provide trifluoroacetate salts. To obtain acetate salts the fractions from runs with buffer P were reloaded onto the column and the column was washed with 5 volumes of 0.1 M ammonium acetate. The final product was eluted with buffer A. The fractions were pooled and lyophilized.

TABLE 1

Buffer Compositions

| Buffer | Component A | Component B |
|---|---|---|
| P | 0.25M Triethylammonium Phosphate (TEAP) (pH 5.2) | 60% acetonitrile, 40% Component A |
| T | 0.1% Trifluoroacetic acid (TFA) | 60% acetonitrile, 0.1% TFA |
| A | 2% Acetic acid (AcOH) | 60% acetonitrile, 2% AcOH |

To prepare the alkyl-linked (alkyl as substituent "Q" in Formula (I) hybrids, residues 1-9 were assembled with an orthogonal protecting group (Mtt or ivDde) in position 8 as described above. The orthogonal protecting group was then removed and the 2-nitrobenzenesulfonyl group was introduced with 2-nitrobenzenesulfonyl chloride/2,4,6-collidine in DCM. The resulting resin-bound sulfonamide was alkylated with an appropriate primary alcohol (e.g. 5-Fmoc-amino-1-pentanol) under the Mitsunobu reaction conditions (10 equivalents of alcohol/TPP/DIAD in dry DME, overnight). The remaining residues 10-18 were subsequently added one-by-one and the 2-nitrobenzenesulfonyl was removed with 5% potassium thiophenolate in DMF (3 times for 30 min.). The cleavage, cyclization and purifications were performed as described above.

The compounds prepared were typically found to be at least about 90% pure, e.g., at least about 95% pure, or at least about 97% pure, or at least about 98.5% pure.

Illustrative syntheses of some of the compounds described herein are provided below.

2. Synthesis of Compound No. 2

The 1-9 fragment was assembled manually starting from 15 g (10 mmol) of Rink Amide AM resin (EMD Biosciences, catalog number 855004, 0.68 mmol/g). DIC/HOBt mediated couplings in DCM/DMF (1:1 v/v, for Gly, Orn, Pro, Cys, Ile, Phe and Cys) or in DMF (Asn, Gln) were employed. Single cycles of at least 2 h with a 1.5-3-fold excess of activated Fmoc-protected amino acids were used during the synthesis. The completeness of couplings was assessed with the ninhydrin test. Removal of the Fmoc protecting group was achieved with a single 30 min. wash of the peptide resin with 20% piperidine in DMF. The following amino acid derivatives were used to assemble residues 1-9 of the resin-bound peptide: Fmoc-Gly-OH, Fmoc-Orn(Mtt)-OH, Fmoc-Pro-OH, Fmoc-Cys(Trt)-OH, Fmoc-Asn(Trt)-OH, Fmoc-Gln(Trt)-OH, Fmoc-Ile-OH, Fmoc-Phe-OH and Boc-Cys(Trt)-OH. After the residue 1-9 peptide fragment has been assembled the resin was washed thoroughly with DCM and treated with the DCM/HFIP/TFE/TIS 13:4:2:1 (v/v/v/v) cocktail (2×2 h, 200 mL each). The resin was then washed with DCM, MeOH, DMF and DCM. The resin was wet-split at this point and the synthesis was continued at a 1 mmol scale. (The remainder of the split portion was used to synthesize other compounds, according to the description herein.)

The 2-nitrobenzenesulfonyl group was introduced with 2-nitrobenzenesulfonyl chloride (1.11 g, 5 mmol) and 2,4,6-collidine (1 mL, 7.5 mmol) in DCM. After 2 h the ninhydrin test was negative. The resulting resin-bound sulfonamide was washed with dry DME and suspended in 5 mL of dry DME. 2.63 g (10 mmol) 5-Fmoc-amino-1-pentanol and 2.63 g (10 mmol) were subsequently added to the suspension followed by a solution of 1.97 mL (10 mmol) of DIAD and the resin was shaken overnight. An aliquot of the resin was cleaved to test the completeness of the alkylation. No substrate peak was detected by HPLC analysis of the cleaved peptide. The resin was split again and the synthesis was carried on at a 0.2 mmol scale. The resin was then placed in two automatic synthesis vessels each containing about 0.1 mmol resin-bound intermediate peptide. The synthesis was continued in parallel fashion on the Tribute peptide synthesizer. Single couplings (with each amino acid 10-18 added, one-at-a-time) were mediated with HBTU/NMM in DMF with a 5-fold excess of Fmoc-protected amino acids were used. The Fmoc protecting group was removed with two consecutive 10 min. washes with 20% piperidine in DMF. The following derivatives were used in the automatic synthesis: Fmoc-Glu-NH$_2$, Fmoc-Arg(Pbf)-OH, Fmoc-Pro-OH, Fmoc-Ala-OH, Fmoc-Asn(Trt)-OH, Fmoc-Gln(Trt)-OH, Fmoc-Phe-OH, Fmoc-D-Tyr(Me)-OH and PhAc—OH.

After the entire peptide has been assembled, the two resins were pooled and the 2-nitrobenzenesulfonyl group was removed with 5% potassium thiophenolate in DMF (2 washes of 30 min. each). Upon completion of the peptide synthesis, the peptide resin was washed with DCM and dried in vacuo. The peptide was cleaved from the resin with 20 mL of TFA/H$_2$O/TIS 96:2:2 (v/v/v) for 2 h. The resin was filtered off and TFA was evaporated. The crude product was precipitated with diethyl ether and decanted. The precipitate was dissolved in 10 mL of neat TFA and the solution was subsequently poured into 200 mL of 10% acetonitrile in water. The linear peptide was oxidized with 0.1 M I$_2$/MeOH. The oxidizer solution was added dropwise until yellow color persisted. The excess of iodine was reduced with solid ascorbic acid. The pH was then adjusted to about 4 with concentrated ammonia. The obtained solution was loaded directly onto an HPLC prep column and purified with buffer system P eluted with a gradient of component B (see table below). The fractions with a purity exceeding 93%, determined by reverse-phase analytical HPLC, were pooled and reloaded onto the column and eluted with buffer T to provide trifluoroacetate salt. The fractions were pooled and lyophilized. 46.2 mg (0.018 mmol, 9% assuming 85% peptide content) of white peptide powder was obtained.

The product purity was determined by analytical HPLC as 99.0% and the observed M+H as 2213.8 (calc. M+H was 2214.1).

3. Synthesis of Compound No. 42

The fragment comprising residues 5-9 (referring to Formula (I)) was assembled manually starting from 0.68 g (1 mmol) of Rink Amide AM resin (EMD Biosciences, catalog number 855004, 0.68 mmol/g). DIC/HOBt mediated couplings in DMF were employed. Single cycles of at least 2 h with a 3-4-fold excess of activated Fmoc-protected amino acids were used during the synthesis. The completeness of couplings was assessed with the ninhydrin test. Removal of the Fmoc protecting group was achieved with a single 30 min. wash of the peptide resin with 20% piperidine in DMF. The following amino acid derivatives were used to assemble the residue numbers 5-9 resin-bound peptide: Fmoc-Gly-OH, Fmoc-Dab(ivDde)-OH, Fmoc-Pro-OH, Fmoc-Cys(Trt)-OH and Fmoc-Asn(Trt)-OH. After the fragment comprising residues numbered 5-9 was assembled, the resin was wet-split and the synthesis was continued at a 0.3 mmol scale on the Tribute peptide synthesizer with UV monitoring. (The remainder of this product was used in the synthesis of other compounds as described herein.)

Single couplings mediated with HBTU/NMM in DMF with a 5-fold excess of Fmoc-protected amino acids were used. The Fmoc protecting group was removed with several consecutive 2 min. washes with 20% piperidine in DMF. The following amino acid derivatives were used to assemble the fragment comprising residues numbered 1-4 (see Formula (I)) as a resin-bound peptide: Fmoc-Gln(Trt)-OH, Fmoc-Ile-OH, Fmoc-Phe-OH and Boc-Cys(Trt)-OH. After the residue number 1-4 fragment was assembled the ivDde group was removed with 2% hydrazine/DMF (20 mL, 3×10 min.) and the synthesis was continued on Tribute to introduce the linker (Q) and the residues 10-18 of the peptide sequence. The synthesizer settings were identical as those used in the assembly of the 1-4 fragment. The following derivatives were used in this part of automatic synthesis: Boc-Lys(Fmoc)-OH, Fmoc-Lys(Mtt)-OH, Fmoc-Glu-$NH_2$, Fmoc-Arg(Pbf)-OH, Fmoc-Pro-OH, Fmoc-Ala-OH, Fmoc-Asn(Trt)-OH, Fmoc-Gln(Trt)-OH, Fmoc-Phe-OH, Fmoc-D-Tyr(Me)-OH and PhAc—OH. After the entire peptide sequence has been assembled the resin was washed thoroughly with DCM and treated with the DCM/HFIP/TFE/TIS 13:4:2:1 (v/v/v/v) cocktail (3×1 h, 20 mL each). The resin was then washed with DCM and DMF and acetylated with acetic anhydride (0.28 mL, 3 mmol) in DMF. Finally, the resin was washed with DMF, MeOH and DCM and dried in vacuo. The peptide was cleaved from the resin with 20 mL of TFA/$H_2$O/TIS 96:2:2 (v/v/v) for 2 h. The subsequent steps were the same as in the synthesis of compound 2. The fractions were pooled and lyophilized. 249.6 mg (0.088 mmol, 29% assuming 85% peptide content) of white peptide powder was obtained.

The product purity was determined by analytical HPLC as 95.3% and the observed M+H was 2413.0 (calc. M+H=2413.2).

4. Synthesis of Compound No. 47

The fragment comprising residues numbered 5-9 (see Formula (I)) was assembled manually starting from 0.6 g (1 mmol) of Rink Amide ChemMatrix resin (PCAS BioMatrix Inc, catalog number 7-600-1310, 0.6 mmol/g). DIC/HOBt mediated couplings in DMF were employed. Single cycles of at least 2 h with a 3-4-fold excess of activated Fmoc-protected amino acids were used during the synthesis. The completeness of couplings was assessed with the ninhydrin test. Removal of the Fmoc protecting group was achieved with a single 30 min. wash of the peptide resin with 20% piperidine in DMF. The following amino acid derivatives were used to assemble the 1-9 resin-bound peptide: Fmoc-Gly-OH, Fmoc-Dab(ivDde)-OH, Fmoc-Pro-OH, Fmoc-Cys(Trt)-OH, Fmoc-Asn(Trt)-OH, Fmoc-Hgn(Trt)-OH, Fmoc-Ile-OH, Fmoc-Phe-OH and Boc-Cys(Trt)-OH. After the 1-9 peptide fragment was assembled, the resin was washed 3 times with 20 mL of 2% hydrazine/DMF and wet-split at this point and the synthesis was continued at the 0.3 mmol scale on the Tribute peptide synthesizer with UV monitoring to introduce the linker (Q) and the residue 10-18 peptide sequence. (The remainder of the 1-9 residue resin product was used to synthesis other compounds described herein)

Single couplings mediated with HBTU/NMM in DMF with a 5-fold excess of Fmoc-protected amino acids were used in the automatic synthesis. The Fmoc protecting group was removed with several consecutive 2 min. washes with 20% piperidine in DMF. The following derivatives were used in the automatic synthesis: Boc-Lys(Fmoc)-OH, Fmoc-Glu-$NH_2$, Fmoc-Arg(Pbf)-OH, Fmoc-Pro-OH, Fmoc-Cit-OH, Fmoc-Asn(Trt)-OH, Fmoc-Gln(Trt)-OH, Fmoc-Phe-OH, Fmoc-D-Tyr(Me)-OH and PhAc—OH. Upon completion of the peptide synthesis, the peptide resin was washed with DCM and dried in vacuo. The peptide was cleaved from the resin with 20 mL of TFA/$H_2$O/TIS 96:2:2 (v/v/v) for 2 h. The subsequent steps were the same as in the synthesis of compound 2. The fractions were pooled and lyophilized. 174.3 mg (0.063 mmol, 21% assuming 85% peptide content) of white peptide powder was obtained.

The product purity was determined by analytical HPLC as 96.9% and the observed M+H was 2343.2 (calc. MH=2343.1).

5. Synthesis of Compound No. 29 by Boc/Fmoc Strategy

The fragment comprising residues 8-9 (referring to Formula (I)) was assembled manually starting from 5.00 g (3.5 mmol) of MBHA resin (EMD Biosciences, catalog number 855006, 0.70 mmol/g). DCC or DIC/HOBt mediated couplings in DCM were employed. Single cycles of at least 2 h with a 2-4-fold excess of activated Boc-protected amino acids were used during the synthesis. The completeness of couplings was assessed with the ninhydrin test. Removal of the Boc protecting group was achieved with two consecutive washes (5 and 25 min.) of the peptide resin with 50% TFA/DCM containing 1% m-cresol. Neutralization of the peptide resin was accomplished with two 5 min. washes with 5% TEA/DCM. The following amino acid derivatives were used to assemble the residue numbers 8-9 resin-bound peptide: Boc-Gly-OH and Boc-Dab(Fmoc)-OH. After the fragment comprising residues numbered 8-9 was assembled, the resin was split and the synthesis was continued manually at a 0.5 mmol scale. (The remainder of this product was used in the synthesis of other compounds as described herein.)

The fragment comprising residues numbered 2-7 (see Formula (I)) was subsequently assembled using synthetic methods described for the 8-9 fragment. The following derivatives were used in this segment: Boc-Pro-OH, Boc-Cys(Mob)-OH, Boc-Asn-OH, Boc-Gln-OH, Boc-Ile-OH and Boc-Phe-OH. The resin was split again and the synthesis was continued manually at a 0.13 mmol scale. The position 1 amino acid was introduced as Z(2-Cl)-Cys(Mob)-OH and the Fmoc group was removed with two consecutive washes with 25% piperidine in DMF (5 and 20 min., respectively). Fmoc-Lys(Boc)-OH was then coupled and the remaining fragment comprising residues numbered 10-18 (see Formula (I)) was subsequently assembled by Boc chemistry. The following amino acid derivatives were used to synthesize this fragment: Boc-Glu-$NH_2$, Boc-Arg(Tos)-OH, Boc-Pro-OH, Boc-Ala-OH, Boc-Asn-OH, Boc-Gln-OH, Boc-Phe-OH, Boc-D-Tyr(Me)-OH and PhAc—OH. After the entire peptide sequence has been assembled the resin was washed thoroughly with DMF and treated with 25% piperidine in DMF (5 and 20 min) The resin was then washed with DMF, suspended in NMP/DMSO (1:1, v/v) and guanylated with 1H-Pyrazole-1-carboxamidine HCl (Aldrich #02729LB)/DIPEA. Finally, the resin was washed with DMF, MeOH and DCM and dried in vacuo. The peptide was cleaved from the resin with 20 mL of HF/anisole 20:1 (v/v) for 1.5 h at 0° C. The resin/crude peptide was washed with 100 mL of ethyl ether and the peptide was extracted with 100 mL of acetic acid/water 3:1, (v/v). The subsequent steps were the same as in the synthesis of compound 2. The fractions were pooled and lyophilized. 47.5 mg (0.018 mmol, 7% assuming 85% peptide content) of white peptide powder was obtained.

The product purity was determined by analytical HPLC as 100.0% and the observed M+H was 2285.1 (calc. M+H=2285.2).

6. Analytical Data for Example Compounds

Additional example compounds were prepared, in general using synthetic methods analogous to those described above. Analytical data for example compounds that were prepared are provided in Table 2.

TABLE 2

Analytical Data for Example Compounds

| Compound | Structure | Mass Spectrometric Data (M + H) | |
|---|---|---|---|
| | | Calculated | Observed |
| 1 | H-Cys-Phe-Ile-Gln-Asn-Cys-Pro-Orn((CH$_2$)$_6$—NHCO—(CH$_2$)$_2$—CO)-Gly-NH$_2$<br>\|<br>PhAc-D-Tyr(Me)-Phe-Gln-Asn-Arg-Pro-Arg-Lys-NH$_2$ | 2412.0 | 2412.0 |
| 2 | H-Cys-Phe-Ile-Gln-Asn-Cys-Pro-Orn((CH$_2$)$_5$—NH)-Gly-NH$_2$<br>\|<br>PhAc-D-Tyr(Me)-Phe-Gln-Asn-Ala-Pro-Arg-Glu-NH$_2$ | 2214.1 | 2213.8 |
| 3 | H-Cys-Phe-Ile-Gln-Asn-Cys-Pro-Orn((CH$_2$)$_4$—NHCO—(CH$_2$)$_3$—CO)-Gly-NH$_2$<br>\|<br>PhAc-D-Tyr(Me)-Phe-Gln-Asn-Arg-Pro-Arg-Lys-NH$_2$ | 2398.2 | 2398.3 |
| 4 | H-Cys-Phe-Ile-Gln-Asn-Cys-Pro-Orn((CH$_2$)$_6$—NH)-Gly-NH$_2$<br>\|<br>PhAc-D-Tyr(Me)-Phe-Gln-Asn-Ala-Pro-Arg-Glu-NH$_2$ | 2228.1 | 2227.8 |
| 5 | H-Cys-Phe-Ile-Gln-Asn-Cys-Pro-Orn((CH$_2$)$_6$—NHCO—(CH$_2$)$_4$—NH)-Gly-NH$_2$<br>\|<br>PhAc-D-Tyr(Me)-Phe-Gln-Asn-Ala-Pro-Arg-Glu-NH$_2$ | 2327.2 | 2326.8 |
| 6 | H-Cys-Phe-Ile-Gln-Asn-Cys-Pro-Orn((CH$_2$)$_5$—CO)-Gly-NH$_2$<br>\|<br>PhAc-D-Tyr(Me)-Phe-Gln-Asn-Ala-Pro-Arg-Glu-NH$_2$ | 2327.2 | 2327.2 |
| 7 | H-Cys-Phe-Ile-Gln-Asn-Cys-Pro-Orn((CH$_2$)$_3$—CO)-Gly-NH$_2$<br>\|<br>PhAc-D-Tyr(Me)-Phe-Gln-Asn-Arg-Pro-Arg-Lys-NH$_2$ | 2299.1 | 2299.2 |
| 8 | H-Cys-Phe-Ile-Gln-Asn-Cys-Pro-Orn((CH$_2$)$_5$—CO)-Gly-NH$_2$<br>\|<br>PhAc-D-Tyr(Me)-Phe-Gln-Asn-Ala-Pro-Arg-Lys-NH$_2$ | 2242.1 | 2242.0 |
| 9 | H-Cys-Phe-Ile-Gln-Asn-Cys-Pro-Orn((CH$_2$)$_5$—CO)-Gly-NH$_2$<br>\|<br>PhAc-D-Tyr(Me)-Phe-Gln-Asn-Leu-Pro-Arg-Lys-NH$_2$ | 2284.2 | 2284.0 |
| 10 | H-Cys-Phe-Ile-Gln-Asn-Cys-Pro-Orn((CH$_2$)$_4$—NH)-Gly-NH$_2$<br>\|<br>PhAc-D-Tyr(Me)-Phe-Gln-Asn-Arg-Pro-Arg-Glu-NH$_2$ | 2285.1 | 2284.9 |
| 11 | H-Cys-Phe-Ile-Gln-Asn-Cys-Pro-Orn((CH$_2$)$_5$—NH)-Gly-NH$_2$<br>\|<br>PhAc-D-Tyr(Me)-Phe-Gln-Asn-Ser-Pro-Arg-Glu-NH$_2$ | 2230.1 | 2230.2 |

TABLE 2-continued

Analytical Data for Example Compounds

| Compound | Structure | Mass Spectrometric Data (M + H) | |
|---|---|---|---|
| | | Calculated | Observed |
| 12 | H-Cys-Phe-Ile-Gln-Asn-Cys-Pro-Orn((CH$_2$)$_5$—NH)-Gly-NH$_2$<br>　　　　　　　　　　　　　　　　　｜<br>PhAc-D-Tyr(Me)-Phe-Gln-Asn-Lys-Pro-Arg-Glu-NH$_2$ | 2271.1 | 2271.2 |
| 13 | H-Cys-Phe-Ile-Gln-Asn-Cys-Pro-Orn((CH$_2$)$_5$—NH)-Gly-NH$_2$<br>　　　　　　　　　　　　　　　　　｜<br>PhAc-D-Tyr(Me)-Phe-Gln-Asn-His-Pro-Arg-Glu-NH$_2$ | 2280.1 | 2280.2 |
| 14 | H-Cys-Phe-Ile-Gln-Asn-Cys-Pro-Orn((CH$_2$)$_5$—NH)-Gly-NH$_2$<br>　　　　　　　　　　　　　　　　　｜<br>PhAc-D-Tyr(Me)-Phe-Gln-Asn-Gln-Pro-Arg-Glu-NH$_2$ | 2271.1 | 2271.2 |
| 15 | H-Cys-Phe-Ile-Gln-Asn-Cys-Pro-Orn((CH$_2$)$_5$—NH)-Gly-NH$_2$<br>　　　　　　　　　　　　　　　　　｜<br>PhAc-D-Tyr(Me)-Phe-Gln-Asn-Cit-Pro-Arg-Glu-NH$_2$ | 2300.1 | 2300.2 |
| 16 | H-Cys-Phe-Ile-Gln-Asn-Cys-Pro-Orn((CH$_2$)$_5$—NH)-Gly-NH$_2$<br>　　　　　　　　　　　　　　　　　｜<br>PhAc-D-Tyr(Me)-Phe-Gln-Asn-Dab-Pro-Arg-Glu-NH$_2$ | 2243.1 | 2243.2 |
| 17 | H-Cys-Phe-Ile-Gln-Asn-Cys-Pro-Orn((CH$_2$)$_6$—NH)-Gly-NH$_2$<br>　　　　　　　　　　　　　　　　　｜<br>heptanoyl-D-Tyr(Me)-Phe-Gln-Asn-Ala-Pro-Arg-Glu-NH$_2$ | 2222.5 | 2222.4 |
| 18 | H-Cys-Phe-Ile-Gln-Asn-Cys-Pro-Dab(CO—CH(NH$_2$)—(CH$_2$)$_4$—NH)-Gly-NH$_2$ (S)<br>　　　　　　　　　　　　　　　　　｜<br>PhAc-D-Tyr(Me)-Phe-Gln-Asn-Ala-Pro-Arg-Glu-NH$_2$ | 2243.1 | 2243.2 |
| 19 | H-Cys-Phe-Ile-Gln-Asn-Cys-Pro-Orn((CH$_2$)$_6$—NH)-Gly-NH$_2$<br>　　　　　　　　　　　　　　　　　｜<br>cHxCO-D-Tyr(Me)-Phe-Gln-Asn-Ala-Pro-Arg-Glu-NH$_2$ | 2220.1 | 2220.2 |
| 20 | H-Cys-Phe-Ile-Gln-Asn-Cys-Pro-Orn((CH$_2$)$_5$—NHCO(CH$_2$)$_2$—NH)-Gly-NH$_2$<br>　　　　　　　　　　　　　　　　　｜<br>PhAc-D-Tyr(Me)-Phe-Gln-Asn-Ala-Pro-Arg-Glu-NH$_2$ | 2285.1 | 2285.4 |
| 21 | H-Cys-Phe-Ile-Gln-Asn-Cys-Pro-Orn((CH$_2$)$_6$—NH)-Gly-NH$_2$<br>　　　　　　　　　　　　　　　　　｜<br>iBuCO-D-Tyr(Me)-Phe-Gln-Asn-Ala-Pro-Arg-Glu-NH$_2$ | 2194.1 | 2194.2 |
| 22 | H-Cys-Phe-Ile-Gln-Asn-Cys-Pro-Orn(CO—CH(NH$_2$)—(CH$_2$)$_4$—NH)-Gly-NH$_2$ (S)<br>　　　　　　　　　　　　　　　　　｜<br>PhAc-D-Tyr(Me)-Phe-Gln-Asn-Arg-Pro-Arg-Glu-NH$_2$ | 2315.2 | 2314.8 |
| 23 | H-Hmp-Phe-Ile-Gln-Asn-Cys-Pro-Orn((CH$_2$)$_5$—NH)-Gly-NH$_2$<br>　　　　　　　　　　　　　　　　　｜<br>PhAc-D-Tyr(Me)-Phe-Gln-Asn-Ala-Pro-Arg-Glu-NH$_2$ | 2215.1 | 2215.0 |
| 24 | H-Cys-Phe-Ile-Gln-Asn-Cys-Pro-Orn(CO—CH(NH$_2$)—(CH$_2$)$_4$—NH)-Gly-NH$_2$ (S)<br>　　　　　　　　　　　　　　　　　｜<br>PhAc-D-Tyr(Me)-Phe-3-Pal-Asn-Arg-Pro-Arg-Glu-NH$_2$ | 2362.2 | 2362.2 |
| 25 | H-Cys-Phe-Ile-Gln-Asn-Cys-Pro-Orn(CO—CH(NH$_2$)—(CH$_2$)$_4$—NH)-Gly-NH$_2$ (S)<br>　　　　　　　　　　　　　　　　　｜<br>PhAc-D-Phe(4-Cl)-Phe-Gln-Asn-Arg-Pro-Arg-Glu-NH$_2$ | 2346.1 | 2346.0 |

TABLE 2-continued

Analytical Data for Example Compounds

| Compound | Structure | Mass Spectrometric Data (M + H) Calculated | Mass Spectrometric Data (M + H) Observed |
|---|---|---|---|
| 26 | H-Cys-Phe-Ile-Gln-Asn-Cys-Pro-Orn(CO—CH(NHC(=NH)NH$_2$)—(CH$_2$)$_4$—NH)-Gly-NH$_2$ (S)<br>\|<br>PhAc-D-Tyr(Me)-Phe-Gln-Asn-Arg-Pro-Arg-Glu-NH$_2$ | 2384.2 | 2384.2 |
| 27 | H-Cys-Phe-Ile-Gln-Asn-Cys-Pro-Orn(CO—CH(NH$_2$)—(CH$_2$)$_4$—NH)-Gly-NH$_2$ (S)<br>\|<br>PhAc-Phe(4-Cl)-Phe-Gln-Asn-Arg-Pro-Arg-Glu-NH$_2$ | 2346.1 | 2346.0 |
| 28 | H-Cys-Phe-Ile-Gln-Asn-Cys-Pro-Orn(CO—CH(NH$_2$)—(CH$_2$)$_4$—NH)-Gly-NH$_2$ (S)<br>\|<br>PhAc-D-Tyr(Me)-Phe-Gln-Asn-Ala-Pro-Arg-Glu-NH$_2$ | 2257.1 | 2257.0 |
| 29 | H-Cys-Phe-Ile-Gln-Asn-Cys-Pro-Dab(CO—CH(NHC(=NH)NH$_2$)—(CH$_2$)$_4$—NH)-Gly-NH$_2$ (S)<br>\|<br>PhAc-D-Tyr(Me)-Phe-Gln-Asn-Ala-Pro-Arg-Glu-NH$_2$ | 2285.1 | 2285.2 |
| 30 | H-Hmp-Phe-Ile-Gln-Asn-Cys-Pro-Dab(CO—CH(NH$_2$)—(CH$_2$)$_4$—NH)-Gly-NH$_2$ (S)<br>\|<br>PhAc-D-Tyr(Me)-Phe-Gln-Asn-Ala-Pro-Arg-Glu-NH$_2$ | 2244.1 | 2244.2 |
| 31 | H-Hmp-Phe-Ile-Gln-Asn-Cys-Pro-Dab(CO—CH(NH$_2$)—(CH$_2$)$_4$—NH)-Gly-NH$_2$ (S)<br>\|<br>PhAc-D-Tyr(Me)-Phe-Gln-Asn-Arg-Pro-Arg-Glu-NH$_2$ | 2329.1 | 2329.4 |
| 32 | H-Hmp-Phe-Ile-Gln-Asn-Cys-Pro-Dab(CO—CH(NH$_2$)—(CH$_2$)$_4$—NH)-Gly-NH$_2$ (S)<br>\|<br>PhAc-D-Tyr(Me)-Phe-Gln-Asn-Lys-Pro-Arg-Glu-NH$_2$ | 2301.1 | 2031.2 |
| 33 | H-Hmp-Phe-Ile-Gln-Asn-Cys-Pro-Dab(CO—CH(NH$_2$)—(CH$_2$)$_4$—NH)-Gly-NH$_2$ (S)<br>\|<br>iBuCO-D-Tyr(Me)-Phe-Gln-Asn-Lys-Pro-Arg-Glu-NH$_2$ | 2267.1 | 2267.2 |
| 35 | H-Cys-Phe-Ile-Gln-Asn-Cys-Pro-Dab(CO—CH(NH$_2$)—(CH$_2$)$_4$—NH)-Gly-NH$_2$ (S)<br>\|<br>PhAc-D-Tyr(Me)-Phe-Gln-Asn-Lys-Pro-Arg-Glu-NH$_2$ | 2300.1 | 2300.2 |
| 36 | H-Cys-Phe-Ile-Gln-Asn-Cys-Pro-Dab(CO—CH(NH$_2$)—(CH$_2$)$_4$—NH)-Gly-NH$_2$ (S)<br>\|<br>PhAc-D-Tyr(Me)-Ile-Gln-Asn-Arg-Pro-Arg-Glu-NH$_2$ | 2294.1 | 2294.4 |
| 37 | H-Cys-Phe-Ile-Gln-Asn-Cys-Pro-Dab(CO—CH(NH$_2$)(CH$_2$)$_4$—NHCO—(CH$_2$)$_4$—NH)-Gly-NH$_2$ (S)<br>\|<br>PhAc-D-Tyr(Me)-Phe-Gln-Asn-Ala-Pro-Arg-Glu-NH$_2$ | 2342.1 | 2342.4 |
| 38 | H-Cys-Phe-Ile-Gln-Asn-Cys-Pro-Dab(CO—CH(NH$_2$)—(CH$_2$)$_2$—CO)-Gly-NH$_2$ (S)<br>\|<br>PhAc-D-Tyr(Me)-Phe-Gln-Asn-Ala-Pro-Arg-Lys-NH$_2$ | 2243.1 | 2243.2 |
| 39 | H-Cys-Phe-Ile-Gln-Asn-Cys-Pro-Dab(CO—CH(NH$_2$)—(CH$_2$)$_4$—NH)-Gly-NH$_2$ (R)<br>\|<br>PhAc-D-Tyr(Me)-Phe-Gln-Asn-Ala-Pro-Arg-Glu-NH$_2$ | 2243.1 | 2242.8 |
| 41 | H-Cys-Phe-Ile-Gln-Asn-Cys-Pro-Dab(CO—CH(NH$_2$)—(CH$_2$)$_4$—NH—CO—CH((CH$_2$)$_4$NH$_2$)—NH)-Gly-NH$_2$ (S) (S)<br>\|<br>PhAc-D-Tyr(Me)-Phe-Gln-Asn-Ala-Pro-Arg-Glu-NH$_2$ | 2371.2 | 2371.4 |

TABLE 2-continued

Analytical Data for Example Compounds

| Compound | Structure | Mass Spectrometric Data (M + H) Calculated | Observed |
|---|---|---|---|
| 42 | H-Cys-Phe-Ile-Gln-Asn-Cys-Pro-Dab(CO—CH(NH$_2$)$^{(S)}$—(CH$_2$)$_4$—NH—CO—CH((CH$_2$)$_4$NHaC)$^{(S)}$—NH)-Gly-NH$_2$<br>\|<br>PhAc-D-Tyr(Me)-Phe-Gln-Asn-Ala-Pro-Arg-Glu-NH$_2$ | 2413.2 | 2413.0 |
| 43 | H-Cys-Phe-Ile-Gln-Asn-Cys-Pro-Dab(CO—CH(NH$_2$)$^{(S)}$—(CH$_2$)$_4$—NH—CO—CH((CH$_2$)$_4$NH(heptanoyl))$^{(S)}$—NH)-Gly-NH$_2$<br>\|<br>PhAc-D-Tyr(Me)-Phe-Gln-Asn-Ala-Pro-Arg-Glu-NH$_2$ | 2483.3 | 2483.6 |
| 44 | H-Cys-Phe-Ile-Gln-Asn-Cys-Pro-Dab(CO—CH(NH$_2$)$^{(S)}$—(CH$_2$)$_4$—NH)-Gly-NH$_2$<br>\|<br>PhAc-D-Tyr(Me)-Phe-Gln-Asn-Cit-Pro-Arg-Glu-NH$_2$ | 2329.1 | 2329.4 |
| 45 | H-Cys-Phe-Ile-Gln-Asn-Cys-Pro-Orn((CH$_2$)$_5$—NH-Gly-NH$_2$<br>\|<br>PhAc-D-Tyr(Me)-Phe(4-Cl)-Gln-Asn-Cit-Pro-Arg-Glu-NH$_2$ | 2334.1 | 2334.4 |
| 46 | H-Cys-Phe-Ile-Gln-Asn-Cys-Pro-Orn((CH$_2$)$_5$—NH-Gly-NH$_2$<br>\|<br>PhAc-D-Tyr(Me)-Ala(t-Bu)-Gln-Asn-Cit-Pro-Arg-Glu-NH$_2$ | 2280.1 | 2280.4 |
| 47 | H-Cys-Phe-Ile-Hgn-Asn-Cys-Pro-Dab(CO—CH(NH$_2$)$^{(S)}$—(CH$_2$)$_4$—NH)-Gly-NH$_2$<br>\|<br>PhAc-D-Tyr(Me)-Phe-Gln-Asn-Cit-Pro-Arg-Glu-NH$_2$ | 2343.1 | 2343.2 |
| 48 | H-Hmp-Phe-Ile-Hgn-Asn-Cys-Pro-Dab(CO—CH(NH$_2$)$^{(S)}$—(CH$_2$)$_4$—NH)-Gly-NH$_2$<br>\|<br>PhAc-D-Tyr(Me)-Phe-Gln-Asn-Cit-Pro-Arg-Glu-NH$_2$ | 2344.1 | 2344.4 |
| 49 | H-Cys-Phe-Ile-Gln-Asn-Cys-Pro-Dab(CO—CH(NH$_2$)$^{(R)}$—(CH$_2$)$_4$—NH)-Gly-NH$_2$<br>\|<br>PhAc-D-Tyr(Me)-Phe-Gln-Asn-Cit-Pro-Arg-Glu-NH$_2$ | 2329.1 | 2329.0 |
| 50 | H-Cys-Phe-Ile-Hgn-Asn-Cys-Pro-Dab(CO—CH(NH$_2$)$^{(S)}$—(CH$_2$)$_4$—NH)-Gly-NH$_2$<br>\|<br>PhAc-D-Tyr(Me)-Phe-Gln-Asn-Ala-Pro-Arg-Glu-NH$_2$ | 2257.1 | 2257.4 |
| 51 | H-Cys-Phe-Ile-Hgn-Asn-Cys-Pro-Dab(CO—CH(NH$_2$)$^{(R)}$—(CH$_2$)$_4$—NH)-Gly-NH$_2$<br>\|<br>PhAc-D-Tyr(Me)-Phe-Gln-Asn-Ala-Pro-Arg-Glu-NH$_2$ | 2257.1 | 2257.4 |
| 52 | H-Cys-Phe-Ile-Hgn-Asn-Cys-Pro-Dab(CO—CH(NH$_2$)$^{(R)}$—(CH$_2$)$_4$—NH)-Gly-NH$_2$<br>\|<br>PhAc-D-Tyr(Me)-Phe-Gln-Asn-Cit-Pro-Arg-Glu-NH$_2$ | 2343.1 | 2343.4 |
| 53 | H-Cys-Phe-Ile-Hgn-Asn-Cys-Pro-Dab(CO—CH(NH$_2$)$^{(S)}$—(CH$_2$)$_4$—NH)-Gly-NH$_2$<br>\|<br>PhAc-D-Tyr(Me)-Phe-Gln-Asn-Ala-Pro-Arg-D-Glu-NH$_2$ | 2257.1 | 2257.4 |
| 54 | H-Cys-Phe-Ile-Hgn-Asn-Cys-Pro-Dab(CO—CH(NH$_2$)$^{(S)}$—(CH$_2$)$_4$—NH)-Gly-NH$_2$<br>\|<br>PhAc-D-Tyr(Me)-Phe-Gln-Asn-Ala-Pro-Arg-D-Glu-NH$_2$ | 2243.1 | 2243.4 |
| 55 | H-Cys-Phe-Ile-Gln-Asn-Cys-Pro-Dab(CO—CH(NH$_2$)$^{(R)}$—(CH$_2$)$_4$—NH)-Gly-NH$_2$<br>\|<br>PhAc-D-Tyr(Me)-Phe-Gln-Asn-Cit-Pro-Arg-D-Glu-NH$_2$ | 2329.1 | 2329.4 |

TABLE 2-continued

Analytical Data for Example Compounds

| Compound | Structure | Mass Spectrometric Data (M + H) Calculated | Observed |
|---|---|---|---|
| 56 | H-Cys-Phe-Ile-Gln-Asn-Cys-Pro-Dab(CO—$\overset{(R)}{CH(NH_2)}$—(CH$_2$)$_4$—NH)-Gly-NH$_2$<br>\|<br>PhAc-D-Tyr(Me)-Phe-Gln-Asn-Ala-Pro-Arg-D-Glu-NH$_2$ | 2243.1 | 2243.4 |
| 57 | H-Cys-Phe-Ile-Gln-Asn-Cys-Pro-Dab(CO—$\overset{(S)}{CH(NH_2)}$—(CH$_2$)$_4$—NH)-Gly-NH$_2$<br>\|<br>PhAc-D-Tyr(Me)-Phe-Gln-Asn-Cit-Pro-Arg-D-Glu-NH$_2$ | 2329.1 | 2329.4 |
| 58 | H-Cys-Phe-Ile-Hgn-Asn-Cys-Pro-Dab(CO—$\overset{(R)}{CH(NH_2)}$—(CH$_2$)$_4$—NHCO—$\overset{(S)}{CH((CH_2)_4-NHAc)}$—NH)-Gly-NH$_2$<br>\|<br>PhAc-D-Tyr(Me)-Phe-Gln-Asn-Ala-Pro-Arg-Glu-NH$_2$ | 2427.2 | 2427.3 |
| 59 | H-Cys-Phe-Ile-Asn-Asn-Cys-Pro-Dab(CO—$\overset{(R)}{CH(NH_2)}$—(CH$_2$)$_4$—NH)-Gly-NH$_2$<br>\|<br>PhAc-D-Tyr(Me)-Phe-Gln-Asn-Dab-Pro-Arg-Glu-NH$_2$ | 2258.1 | 2258.3 |
| 60 | H-Cys-Phe-Ile-Asn-Asn-Cys-Pro-Dab(CO—$\overset{(R)}{CH(NH_2)}$—(CH$_2$)$_4$—NH)-Gly-NH$_2$<br>\|<br>PhAc-D-Tyr(Me)-Phe-Gln-Asn-Ala-Pro-Arg-Glu-NH$_2$ | 2229.1 | 2229.2 |
| 61 | H-Cys-Phe-Ile-Hgn-Asn-Cys-Pro-Dab(CO—$\overset{(R)}{CH(NH_2)}$—(CH$_2$)$_4$—NH)-Gly-NH$_2$<br>\|<br>PhAc-D-Tyr(Me)-Phe-Gln-Asn-Gln-Pro-Arg-Glu-NH$_2$ | 2314.1 | 2314.4 |
| 62 | H-Cys-Phe-Ile-Hgn-Asn-Cys-Pro-Dab(CO—$\overset{(R)}{CH(NH_2)}$—(CH$_2$)$_4$—NH)-Gly-NH$_2$<br>\|<br>PhAc-D-Tyr(Me)-Phe-Gln-Asn-Ala-Pro-Arg-Glu-NH$_2$ | 2257.1 | 2257.3 |
| 63 | H-Cys-Phe-Ile-Asn-Asn-Cys-Pro-Dab(CO—$\overset{(S)}{CH(NH_2)}$—(CH$_2$)$_2$—CO)-Gly-NH$_2$<br>\|<br>PhAc-D-Tyr(Me)-Phe-Gln-Asn-Ala-Pro-Arg-Lys-NH$_2$ | 2229.1 | 2229.2 |
| 64 | H-Cys-Phe-Ile-Hgn-Asn-Cys-Pro-Dab(CO—$\overset{(S)}{CH(NH_2)}$—(CH$_2$)$_2$—CO)-Gly-NH$_2$<br>\|<br>PhAc-D-Tyr(Me)-Phe-Gln-Asn-Ala-Pro-Arg-Lys-NH$_2$ | 2257.1 | 2257.3 |
| 65 | H-Cys-Phe-Ile-Hgn-Asn-Cys-Pro-Dab(CO—$\overset{(R)}{CH(NH_2)}$—(CH$_2$)$_2$—CO)-Gly-NH$_2$<br>\|<br>PhAc-D-Tyr(Me)-Phe-Gln-Asn-Ala-Pro-Arg-Lys-NH$_2$ | 2257.1 | 2257.3 |
| 66 | H-Cys-Phe-Ile-Asn-Asn-Cys-Pro-Dab(CO—$\overset{(R)}{CH(NH_2)}$—(CH$_2$)$_2$—CO)-Gly-NH$_2$<br>\|<br>PhAc-D-Tyr(Me)-Phe-Gln-Asn-Ala-Pro-Arg-Lys-NH$_2$ | 2229.1 | 2229.3 |

7. Biological Data for Illustrative Compounds a. Agonist Activity at Vasopressin V1a Receptors The method is designed to determine the agonist activity of compounds at the vasopressin V1a receptors in a cell-based Fluorescence Imaging Plate Reader (FLIPR) assay and to evaluate their $EC_{50}$ values (the concentration of a compound that produces 50% of the maximum possible response). Efficacy (% MPE) is also determined as the percentage of maximal possible effect. This agonist assay utilizes cells from a stable cell line (HEK-flpin) expressing the vasopressin V1a receptor. Intracellular calcium increase in response to agonist is measured through real-time fluorescence of an intracellular calcium-sensitive dye. Cells are exposed to varying concentrations of test agonist compounds whereupon release of intracellular calcium is measured to determine the agonist potency and efficacy.

Materials

Human cells used were from the Flp-In™ 293 cell line (HEK-flpin). The cell line stably expresses the lacZ-Zeocin™ fusion gene and is designed for use with the Flp-In™ expression vector containing the gene of interest and the Flp recombinase expression plasmid, pOG44. The cell line contains a single integrated Flp Recombination Target (FRT) site from pFRT/lacZeo or pFRT/lacZeo2. To generate the HEK-flpin cell line stably expressing the human V1aR, the cells were co-transfected with the Flp-In™ expression vector containing the gene of interest (pcDNA5/FRT-hV1aR) and the Flp recombinase expression plasmid pOG44. Flp recombinase mediates insertion of the Flp-In™ expression vector into the genome at the integrated FRT site through site-specific DNA recombination. Stable cell lines expressing the hV1aR from the Flp-In™ expression vector can be generated by selection using hygromycin B. See Life Technologies/Invitrogen manual, Growth and Maintenance of Flp-In™ Cell Lines, Version E, published Feb. 12, 2003, for detailed information.

Arginine vasopressin (AVP) was used as reference agonist in the assay. Efficacy of this compound was set to be 100%. A stock solution of 5 mM was made up in DMSO and stored at −20° C.

Reagents used were the following: Dimethyl sulfoxide (DMSO) (Sigma, D8779); Dulbecco's Modification of Eagle's Medium (DMEM) with glucose and sodium pyruvate without L-glutamine (Mediatech, 15-013-CV); Fetal Bovine Serum-Heat inactivated (FBS-HI) (Invitrogen, 16140-071); FLIPR Calcium 4 Assay Kit, bulk format (Molecular Devices, R8141); Hanks' Balanced Salt Solution (HBSS) (Invitrogen, 14025-092); Hepes Buffer, pH 7.2 (Mediatech, 25-060-CI); Hygromycin B 50 mg/mL (Mediatech, 30-240-CR); GlutaMAX™-I Supplement, 200 mM (Invitrogen, 35050-061); Phenol red-free DMEM: DMEM with 4.5 g/L glucose and sodium pyruvate without L-glutamine and phenol red (Mediatech, 17-205-CV); Probenecid (Sigma-Aldrich, P-8761); and Trypsin EDTA: 0.05% Trypsin/0.53 mM EDTA (Mediatech, 25-052-CI).

Supplies used were the following: 384 well black clear bottom, poly-D-lysine-coated Assay Plate (Corning, 3712); 384 well V-bottom plate, Dilution Plate (Greiner, 781280); Polystyrene test tube (BD Biosciences, 352057); and T175 Cell+ Flask (Sarstedt, 83.1812.302). Equipment and software used were the following: Fluorometric Imaging Plate Reader (FLIPR Tetra) (Molecular Devices); and ActivityBase software (IDBS, UK).

HEK-flpin-hV1aR, cmcqV1aR, dV1aR and pV1aR cells were maintained in DMEM containing 10% (v/v) FBS-HI, 4 mM GlutaMAX™-I, 25 µg/mL Hygromycin B at 37° C. under 5% $CO_2$ in a humidified atmosphere. Subculture was achieved by splitting semi-confluent cultures 1:3 to 1:6. On the day prior to the assay, cells were removed from culture flasks using Trypsin EDTA and harvested in phenol-red free DMEM containing 10% FBS-HI, 4 mM GlutaMAX™-I. Cells were seeded into 384-well, black clear bottom, poly-D-lysine-treated plates (20 µl/well), at cell density of 20,000 cells/well and incubated overnight.

All compounds were made up in 100% DMSO at 10 mM stock concentrations and stored at −20° C. The compounds were allowed to thaw just before the assay. Compounds were assayed in duplicate at descending concentrations in half-log increments with the highest concentration of 1 or 10 µm depending on the potency of the compounds. Typical dilution procedure of 10× final assay concentration involved a 1:100 top dilution (e.g., 2 µl Stock into 198 µl dilution medium) followed by half-log serial dilutions (e.g., 25.3 µA into 54.7 µl dilution medium supplemented with 1% DMSO (v/v)). (Dilution media consisted of phenol-red free DMEM containing 10% FBS-HI, 4 mM GlutaMAX™-I). The reference (AVP) was tested at 1 µm highest concentration (e.g., 1 µl stock into 999 µl dilution medium). The final DMSO concentration in the assay was 0.1%. The reference (AVP) and the Blank consisting of dilution media supplemented with 0.1% DMSO (v/v) were included in each study.

$EC_{50}$ Determination

Loading Buffer was prepared by dissolving 1 vial of Calcium 4 Assay reagent in 100 mL of 1×HBSS-20 mM Hepes buffer. Probenecid was resuspended at 250 mM in 1 M NaOH followed by a 1:100 dilution in the Loading Buffer for a final working concentration of 2.5 mM. The pH was adjusted to 7.4.

The cells were loaded with Loading Buffer as follows. Cell plates were removed from the incubator and 20 µl of Loading Buffer containing probenecid (2.5 mM) was added to each well. The cells were incubated for 1 hr at 37° C. under 5% $CO_2$ in a humidified atmosphere. The calcium image was obtained as follows. FLIPR Tetra was setup with the following default parameters and a read mode with an excitation wavelength of 470-495 nm and an emission wavelength of 515-575 nm as determined by filter selection: Gain of 20; Excitation Intensity of 80% (Default); Exposure Time of 0.4 seconds (Default).

The cell plates were transferred to FLIPR Tetra, along with a 384 well V-bottom plate pre-loaded with half-log concentrations of test compounds at 10× final test concentrations. The remaining steps of the assay were carried forward by FLIPR Tetra. A baseline reading was taken at 1-second (s) intervals for 5 s followed by the addition of 5 µl of 10× compounds (test, reference, or Blank). The agonist-induced fluorescence signal was then measured for 180 s with initial 120 readings at 1-second intervals followed by 20 readings at 3-second intervals. Overall, each well in the FLIPR assay was composed of the following components in a total volume of 50 µl: 20 µl cells; 20 µl Calcium 4 Loading Buffer; 4.4 µl 10× test or reference compound.

Averaged $EC_{50}$ (in nM) and Efficacy Average (as compared to AVP) are presented in Table 3.

TABLE 3

Assay Results

| Compound # | $EC_{50}$ (Avg) nM | Efficacy Avg. (%) |
|---|---|---|
| AVP | 0.07 | 100.0 |
| 1 | 1.0 | 30 |
| 2 | 0.69 | 52 |
| 3 | 2.9 | 39 |
| 4 | 1.5 | 24 |
| 5 | 1.3 | 28 |
| 6 | 2.5 | 28 |
| 7 | >10,000 | 24 |
| 8 | >10,000 | 50 |
| 9 | >10,000 | 34 |
| 10 | >10,000 | 26 |
| 11 | 2.2 | 51 |
| 12 | 2.3 | 39 |
| 13 | 2.4 | 48 |
| 14 | 2.1 | 37 |
| 15 | 2.3 | 44 |
| 16 | 2.4 | 46 |
| 17 | 2.9 | 62 |
| 18 | 3.9 | 49 |
| 19 | 2.5 | 50 |
| 20 | 2.7 | 42 |
| 21 | 1.5 | 47 |
| 22 | 0.95 | 29 |
| 23 | 1.7 | 51 |
| 24 | 2.3 | 33 |
| 25 | 1.4 | 49 |
| 26 | 0.93 | 32 |
| 27 | 1.0 | 70 |
| 28 | 1.2 | 44 |
| 29 | 1.2 | 39 |
| 30 | 1.1 | 50 |

TABLE 3-continued

Assay Results

| Compound # | EC$_{50}$ (Avg) nM | Efficacy Avg. (%) |
|---|---|---|
| 31 | 0.83 | 63 |
| 32 | 1.0 | 56 |
| 33 | 1.1 | 50 |
| 35 | 1.2 | 43 |
| 36 | 1.2 | 46 |
| 37 | 1.3 | 44 |
| 38 | 1.4 | 46 |
| 39 | 1.8 | 48 |
| 41 | 1.2 | 37 |
| 42 | 1.0 | 37 |
| 43 | 1.4 | 59 |
| 44 | 2.0 | 40 |
| 45 | 0.80 | 72 |
| 46 | 1.4 | 62 |
| 47 | 1.8 | 45 |
| 48 | 1.4 | 67 |
| 49 | 0.76 | 55 |
| 50 | 0.90 | 40 |
| 51 | 1.4 | 43 |
| 52 | 1.5 | 47 |
| 53 | 1.7 | 43 |
| 54 | 1.4 | 51 |
| 55 | 1.7 | 56 |
| 56 | 1.8 | 60 |
| 57 | 1.4 | 63 |
| 58 | 2.6 | 26 |
| 59 | 1.7 | 26 |
| 60 | 2.3 | 42 |
| 61 | 2.5 | 38 |
| 62 | 2.5 | 31 |
| 63 | 1.1 | 36 |
| 64 | 2.9 | 42 |
| 65 | 4.5 | 31 |
| 66 | 2.3 | 30 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages and modifications are within the scope of the following claims.

What is claimed is:

1. A compound according to formula (I):

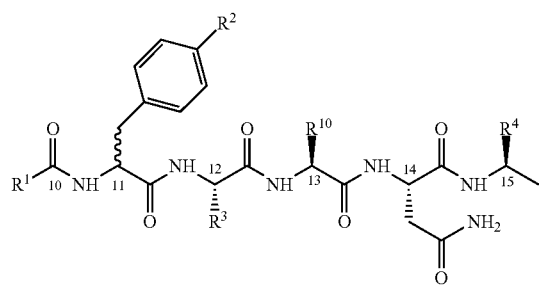

(I)

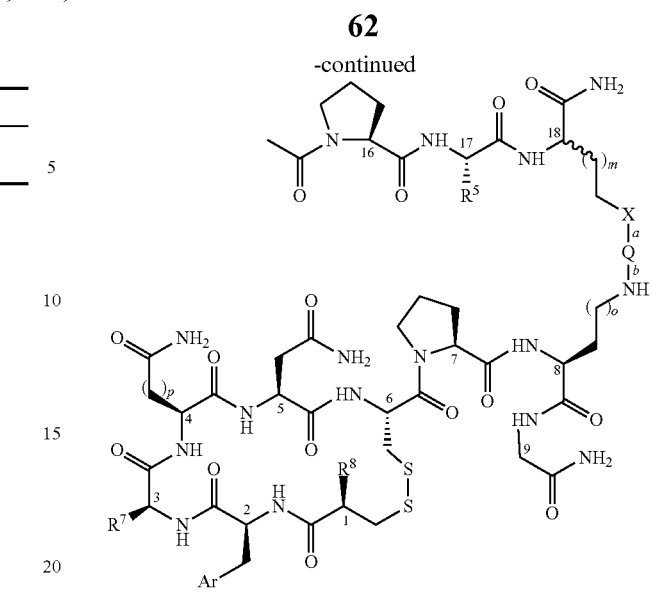

or a salt thereof, wherein:

$R^1$ is selected from $(C_1-C_{10})$alkyl, $(C_1-C_{10})$alkoxy, $(C_1-C_{10})$alkylNH, $Ar^1-L^1-$ and unsubstituted or substituted cycloalkyl;

$Ar^1-L^1-$ is selected from $Ar^1—$, $Ar^1—CH_2—$, $Ar^1—CH_2CH_2—$, $Ar^1—O—$, $Ar^1—CH_2O—$, $Ar^1—NH—$ and $Ar^1—CH_2NH—$;

$Ar^1$ is unsubstituted aryl or substituted aryl;

$R^2$ is selected from hydrogen, $(C_1-C_6)$alkyl, hydroxy, $(C_1-C_6)$alkoxy and halogen;

$R^3$ is selected from $(C_1-C_6)$alkyl, unsubstituted or substituted cycloalkyl and $Cy^3-CH_2—$;

$Cy^3-$ is unsubstituted or substituted aryl or unsubstituted or substituted cycloalkyl;

$R^4$ is selected from $(C_1-C_6)$alkyl, $(C_2-C_6)$alkenyl, $(C_2-C_6)$alkynyl, $(C_1-C_6)$haloalkyl, $—((C_1-C_6)$alkylene$)-OR^{4a}$, $—((C_1-C_6)$alkylene$)-NR^{4a}{}_2$, $—((C_1-C_6)$alkylene$)-S(C_1-C_6)$alkyl, $—((C_1-C_6)$alkylene$)-C(=O)OR^{4a}{}_2$, $—((C_1-C_6)$alkylene$)-C(=O)NR^{4a}{}_2$, $—((C_1-C_6)$alkylene$)-C(=NR^{4a})NR^{4a}{}_2$, $—((C_1-C_6)$alkylene$)-OC(=O)R^{4a}$, $—((C_1-C_6)$alkylene$)-OC(=O)OR^{4a}$, $—((C_1-C_6)$alkylene$)-OC(=O)NR^{4a}{}_2$, $—((C_1-C_6)$alkylene$)-NR^{4a}C(=O)R^{4a}$, $—((C_1-C_6)$alkylene$)-NR^{4a}C(=O)OR^{4a}$, $—((C_1-C_6)$alkylene$)-NR^{4a}C(=O)NR^{4a}{}_2$, $—((C_1-C_6)$alkylene$)-NR^{4a}C(=NR^{4a})NR^{4a}{}_2$, $Ar^4$ and $—((C_1-C_6)$alkylene$)-Ar^4$;

each $R^{4a}$ is independently selected from hydrogen and $(C_1-C_6)$alkyl;

$Ar^4$ is selected from unsubstituted or substituted aryl and unsubstituted or substituted heteroaryl;

$R^5$ is selected from $—((C_1-C_6)$alkylene$)-NR^{5a}{}_2$ and $—((C_1-C_6)$alkylene$)-NR^{5a}C(=NR^{5a})NR^{5a}{}_2$;

each $R^{5a}$ is independently selected from hydrogen and $(C_1-C_6)$alkyl;

Q is selected from the groups $Q^1$, $Q^2$, $Q^3$ and $Q^4$:

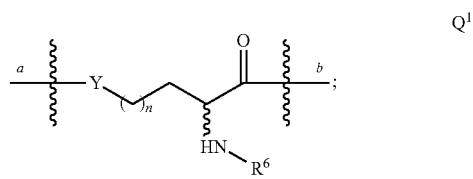

$Q^1$

-continued

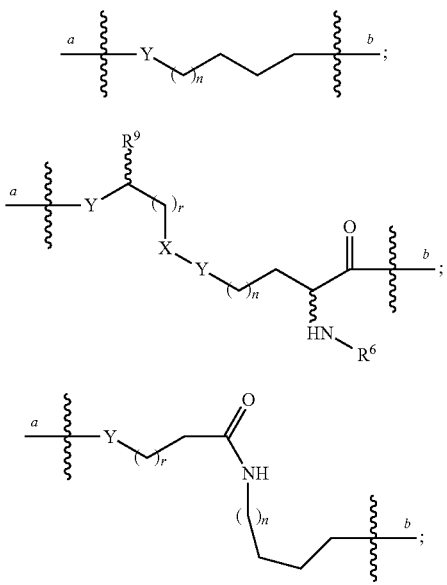

a and b denote the bonds attaching Q to the remainder of the molecule;
$R^6$ is selected from hydrogen, $(C_1-C_6)$alkyl and $—C(=NR^{6a})NR^{6a}{}_2$;
each $R^{6a}$ is hydrogen or $(C_1-C_6)$alkyl;
$R^7$ is selected from $(C_1-C_6)$alkyl, unsubstituted aryl, substituted aryl, unsubstituted cycloalkyl and substituted cycloalkyl;
$R^8$ is selected from $NH_2$ and hydroxyl;
$R^9$ is selected from hydrogen, $(C_1-C_6)$alkyl, $(C_2-C_6)$alkenyl, $(C_2-C_6)$alkynyl, $(C_1-C_6)$haloalkyl, $—((C_1-C_6)$alkylene)-$OR^{9a}$, $—((C_1-C_6)$alkylene)-$NR^{9a}{}_2$, $—((C_1-C_6)$alkylene)-$SR^{9a}$, $—((C_1-C_6)$alkylene)-$C(=O)OR^{9a}{}_2$, $—((C_1-C_6)$alkylene)-$C(=O)NR^{9a}{}_2$, $—((C_1-C_6)$alkylene)-$C(=NR^{9a})NR^{9a}{}_2$, $—((C_1-C_6)$alkylene)-$OC(=O)R^{9a}$, $—((C_1-C_6)$alkylene)-$OC(=O)OR^{9a}$, $—((C_1-C_6)$alkylene)-$OC(=O)NR^{9a}{}_2$, $—((C_1-C_6)$alkylene)-$NR^{9a}C(=O)R^{9b}$, $—((C_1-C_6)$alkylene)-$NR^{9a}C(=O)OR^{9a}$, $—((C_1-C_6)$alkylene)-$NR^{9a}C(=O)NR^{9a}{}_2$, $—((C_1-C_6)$alkylene)-$NR^{9a}C(=NR^{9a})NR^{9a}{}_2$, $Ar^9$ and $—((C_1-C_6)$alkylene)-$Ar^9$;
each $R^{9a}$ is independently selected from hydrogen and $(C_1-C_6)$alkyl;
each $R^{9b}$ is independently selected from hydrogen and $(C_1-C_{10})$alkyl;
$Ar^9$ is selected from unsubstituted aryl, substituted aryl, unsubstituted heteroaryl, and substituted heteroaryl;
$R^{10}$ is selected from $—((C_1-C_6)$alkylene)-$OR^{10a}$, $—((C_1-C_6)$alkylene)-$C(=O)NR^{10a}{}_2$ and $Ar^{10}—CH_2—$;
$Ar^{10}$ is unsubstituted heteroaryl or substituted heteroaryl;
each $R^{10a}$ is selected from hydrogen and $(C_1-C_6)$alkyl;
Ar is selected from aryl and substituted aryl;
each X is NH and each Y is C=O; or
each X is C=O and each Y is NH;
m is 0, 1, 2, 3, 4 or 5;
n is 0, 1, 2, 3 or 4;
o is 1 or 2;
p is 1, 2 or 3; and
r is 0, 1, 2, 3, 4, 5 or 6; provided that $R^9$ is hydrogen if r is greater than one.

2. The compound or salt thereof according to claim 1, wherein:
$R^1$ is selected from $(C_1-C_{10})$alkyl, $(C_1-C_{10})$alkoxy, $(C_1-C_{10})$alkylNH, $Ar^1-L^1-$ and $Cy^1$;
$Cy^1$ is unsubstituted cycloalkyl or cycloalkyl substituted by 1, 2 or 3 substituents independently selected from $(C_1-C_6)$alkyl, $(C_2-C_6)$alkenyl, $(C_2-C_6)$alkynyl, halogen, $(C_1-C_6)$haloalkyl, $—OR^{1a}$ and oxo;
$Ar^1$ is unsubstituted aryl or aryl substituted by 1, 2 or 3 substituents independently selected from $(C_1-C_6)$alkyl, $(C_2-C_6)$alkenyl, $(C_2-C_6)$alkynyl, halogen, $(C_1-C_6)$haloalkyl, $—CN$, $—NO_2$, $—OR^{1a}$, $—NR^{1a}{}_2$ and $—NR^{1a}C(=O)R^{1a}$;
each $R^{1a}$ is independently selected from hydrogen and $(C_1-C_6)$alkyl;
$Cy^3$ is $Ar^3$ or unsubstituted cycloalkyl or cycloalkyl substituted by 1, 2 or 3 substituents independently selected from $(C_1-C_6)$alkyl, $(C_2-C_6)$alkenyl, $(C_2-C_6)$alkynyl, halogen, $(C_1-C_6)$haloalkyl, $—OR^{3a}$ and oxo;
$Ar^3—$ is unsubstituted aryl or aryl substituted by 1, 2 or 3 substituents independently selected from $C_1-C_6$ alkyl, $(C_2-C_6)$alkenyl, $(C_2-C_6)$alkynyl, halogen, $(C_1-C_6)$haloalkyl, $—CN$, $—NO_2$, $—OR^{3a}$, $—NR^{3a}{}_2$ and $—NR^{3a}C(=O)R^{3a}$;
each $R^{3a}$ is independently selected from hydrogen and $(C_1-C_6)$alkyl;
$Ar^4$ is selected from unsubstituted aryl, unsubstituted heteroaryl and aryl and heteroaryl substituted by 1, 2 or 3 substituents independently selected from $(C_1-C_6)$alkyl, $(C_2-C_6)$alkenyl, $(C_2-C_6)$alkynyl, halogen, $(C_1-C_6)$haloalkyl, $—CN$, $—NO_2$, $—OR^{4b}$, $—NR^{4b}{}_2$ and $—NR^{4b}C(=O)R^{4b}$;
each $R^{4b}$ is selected from hydrogen and $(C_1-C_6)$alkyl;
$R^7$ is selected from $(C_1-C_6)$alkyl, $Ar^7$ and $Cy^7$;
$Cy^7$ is unsubstituted cycloalkyl or cycloalkyl substituted by 1, 2 or 3 substituents independently selected from $(C_1-C_6)$alkyl, $(C_2-C_6)$alkenyl, $(C_2-C_6)$alkynyl, halogen, $(C_1-C_6)$haloalkyl, $—OR^{7a}$ and oxo;
$Ar^7$ is unsubstituted aryl or aryl substituted by 1, 2 or 3 substituents independently selected from $(C_1-C_6)$alkyl, $(C_2-C_6)$alkenyl, $(C_2-C_6)$alkynyl, halogen, $(C_1-C_6)$haloalkyl, $—CN$, $—NO_2$, $—OR^{7a}$, $—NR^{7a}{}_2$ and $—NR^{7a}C(=O)R^{7a}$;
each $R^{7a}$ is independently selected from hydrogen and $(C_1-C_6)$alkyl;
$Ar^9$ is selected from unsubstituted aryl, unsubstituted heteroaryl and aryl and heteroaryl substituted by 1, 2 or 3 substituents selected from $(C_1-C_6)$alkyl, $(C_2-C_6)$alkenyl, $(C_2-C_6)$alkynyl, halogen, $(C_1-C_6)$haloalkyl, $—CN$, $—NO_2$, $—OR^{9c}$, $—NR^{9c}{}_2$ and $—NR^{9c}C(=O)R^{9c}$;
each $R^{9c}$ is selected from hydrogen and $(C_1-C_6)$alkyl;
$Ar^{10}$ is selected from unsubstituted heteroaryl and heteroaryl substituted by 1, 2 or 3 substituents selected from $(C_1-C_6)$alkyl, $(C_2-C_6)$alkenyl, $(C_2-C_6)$alkynyl, halogen, $(C_1-C_6)$haloalkyl, $—CN$, $—NO_2$, $—OR^{10b}$, $—NR^{10b}{}_2$ and $—NR^{10b}C(=O)R^{10b}$;
each $R^{10b}$ is independently selected from hydrogen and $(C_1-C_6)$alkyl;
Ar is selected from unsubstituted aryl and aryl substituted by 1, 2 or 3 substituents selected from $(C_1-C_6)$alkyl, $(C_2-C_6)$alkenyl, $(C_2-C_6)$alkynyl, halogen, $(C_1-C_6)$haloalkyl, $—CN$, $—NO_2$, $—OR^{Ar}$, $—NR^{Ar}{}_2$ and $—NR^{Ar}C(=O)R^{Ar}$; and
each $R^{Ar}$ is independently selected from hydrogen and $(C_1-C_6)$alkyl.

3. The compound or salt thereof according to claim 1, wherein $R^1$ is $(C_1\text{-}C_{10})$alkyl, $(C_5\text{-}C_7)$cycloalkyl or $Ar^1$—$CH_2$—.

4. The compound or salt thereof according to claim 3, wherein $R^1$ is isobutyl, n-hexyl, cyclohexyl or benzyl.

5. The compound or salt thereof according to claim 1, wherein $R^2$ is selected from hydroxy, $(C_1\text{-}C_6)$alkoxy and halogen.

6. The compound or salt thereof according to claim 5, wherein $R^2$ is $(C_1\text{-}C_6)$alkoxy.

7. The compound or salt thereof according to claim 5, wherein $R^2$ is methoxy.

8. The compound or salt thereof according to claim 1, wherein $R^3$ is selected from $(C_1\text{-}C_6)$alkyl and $Ar^3$—$CH_2$—, wherein $Ar^3$— is unsubstituted or halo-substituted aryl.

9. The compound or salt thereof according to claim 1, wherein $R^3$ is selected from $(C_1\text{-}C_6)$alkyl and $Ar^3$—$CH_2$—, wherein $Ar^3$ is phenyl or halo-substituted phenyl.

10. The compound or salt thereof according to claim 9, wherein $R^3$ is selected from s-butyl, neopentyl, benzyl and 4-chlorobenzyl.

11. The compound or salt thereof according to claim 1, wherein $R^4$ is selected from $(C_1\text{-}C_6)$alkyl, —$((C_1\text{-}C_6)$alkylene)-$OR^{4a}$, —$((C_1\text{-}C_6)$alkylene)-$NR^{4a}_2$, —$((C_1\text{-}C_6)$alkylene)-$C(=O)NR^{4a}_2$, —$((C_1\text{-}C_6)$alkylene)-$NR^{4a}C(=O)NR^{4a}_2$, —$((C_1\text{-}C_6)$alkylene)-$NR^{4a}C(=NR^{4a})NR^{4a}_2$ and —$((C_1\text{-}C_6)$alkylene)-$Ar^4$.

12. The compound or salt thereof according to claim 11, wherein $R^4$ is selected from $(C_1\text{-}C_6)$alkyl, —$(CH_2)_{1-6}$—$OR^{4a}$, —$(CH_2)_{1-6}$—$NR^{4a}_2$, —$(CH_2)_{1-6}$—$C(=O)NR^{4a}_2$, —$(CH_2)_{1-6}$—$NR^{4a}C(=O)NR^{4a}_2$, —$(CH_2)_{1-6}$—$NR^{4a}C(=NR^{4a})NR^{4a}_2$ and —$(CH_2)_{1-6}$—$Ar^4$.

13. The compound or salt thereof according to claim 12, wherein each $R^{4a}$ is hydrogen or methyl and $Ar^4$ is imidazolyl or indolyl.

14. The compound or salt thereof according to claim 11, wherein $R^4$ is selected from Me, isobutyl, —$CH_2OH$, —$(CH_2)_2$—$NH_2$, —$(CH_2)_3$—$NH_2$, —$(CH_2)_4$—$NH_2$, —$(CH_2)_2$—$C(=O)NH_2$, —$(CH_2)_3$—$NHC(=NH)NH_2$, —$(CH_2)_3$—$NHC(=O)NH_2$ and —$CH_2(1H$-imidazol-4-yl).

15. The compound or salt thereof according to claim 1, wherein $R^5$ is selected from —$(CH_2)_{1-6}$—$NR^{5a}_2$ and —$(CH_2)_{1-6}$—$NR^{5a}C(=NR^{5a})NR^{5a}_2$.

16. The compound or salt thereof according to claim 15, wherein each $R^{5a}$ is independently selected from hydrogen and methyl.

17. The compound or salt thereof according to claim 15, wherein $R^5$ is —$(CH_2)_2$—$NH_2$, —$(CH_2)_3$—$NH_2$, —$(CH_2)_4$—$NH_2$ or —$(CH_2)_3$—$NHC(=NH)NH_2$.

18. The compound or salt thereof according to claim 1, wherein $R^7$ is $(C_1\text{-}C_6)$alkyl or $(C_4\text{-}C_7)$cycloalkyl.

19. The compound or salt thereof according to claim 18, wherein $R^7$ is s-butyl.

20. The compound or salt thereof according to claim 1, wherein $R^8$ is —$NH_2$.

21. The compound or salt thereof according to claim 1, wherein $R^8$ is —OH.

22. The compound or salt thereof according to claim 1, wherein $R^{10}$ is selected from —$(CH_2)_{1-6}$—$C(=O)NR^{10a}_2$ and $Ar^{10}$—$CH_2$—.

23. The compound or salt thereof according to claim 1, wherein each $R^{10a}$ is hydrogen or methyl and $Ar^{10}$ is pyridyl.

24. The compound or salt thereof according to claim 1, wherein $R^{10}$ is selected from 1-hydroxyethyl, —$(CH_2)_2$—$C(=O)NH_2$ and 3-pyridyl-$CH_2$—.

25. The compound or salt thereof according to claim 1, wherein Ar is phenyl or substituted phenyl.

26. The compound or salt thereof according to claim 25, wherein Ar is phenyl.

27. The compound or salt thereof according to claim 1, wherein each X is NH and each Y is C=O.

28. The compound or salt thereof according to claim 1, wherein each X is C=O and each Y is NH.

29. The compound or salt thereof according to claim 1, wherein m is 0, 1, 2, 3 or 4.

30. The compound or salt thereof according to claim 1, wherein o is 1 or 2.

31. The compound or salt thereof according to claim 1, wherein p is 1, 2 or 3.

32. The compound or salt thereof according to claim 1, wherein Q is $Q^1$.

33. The compound or salt thereof according to claim 32, wherein n is 1, 2 or 3.

34. The compound or salt thereof according to claim 32, wherein $Q^1$ is $^a$—$NH(CH_2)_4CH(NH_2)$—$C(=O)$—$^b$, $^a$—$NH(CH_2)_4CH(NHC(=NH)NH_2)$—$C(=O)$—$^b$ or $^a$—$C(=O)(CH_2)_2CH(NH_2)$—$C(=O)$—$^b$.

35. The compound or salt thereof according to claim 32, wherein $Q^1$ is $^a$—$NH(CH_2)_4C^{(S)}H(NH_2)$—$C(=O)$—$^b$, $^a$—$NH(CH_2)_4C^{(S)}H(NHC(=NH)NH_2)$—$C(=O)$—$^b$ or $^a$—$C(=O)(CH_2)_2C^{(S)}H(NH_2)$—$C(=O)$—$^b$ or $^a$—$C(=O)(CH_2)_2C^{(R)}H(NH_2)$—$C(=O)$—$^b$.

36. The compound or salt thereof according to claim 1, wherein Q is $Q^3$.

37. The compound or salt thereof according to claim 36, wherein n is 3.

38. The compound or salt thereof according to claim 36, wherein r is 0 or 3.

39. The compound or salt thereof according to claim 36, wherein $R^9$ is selected from —$(CH_2)_{1-6}$—$NR^{9a}_2$ and —$(CH_2)_{1-6}$—$NR^{9a}C(=O)R^{9b}$, each $R^{9a}$ is hydrogen and each $R^{9b}$ is hydrogen or $(C_1\text{-}C_6)$alkyl.

40. The compound or salt thereof according to claim 1, wherein Q is $Q^1$ or $Q^3$ and $R^6$ is hydrogen or —$C(=NH)NH_2$.

41. The compound or salt thereof according to claim 36, wherein $Q^3$ is $^a$—$NH(CH_2)_4$—$C(=O)$—$NH$—$(CH_2)_4CH(NH_2)$—$C(=O)$—$^b$, $^a$—$NHCH((CH_2)_4NH_2)$—$C(=O)$—$NH$—$(CH_2)_4CH(NH_2)$—$C(=O)$—$^b$, $^a$—$NHCH((CH_2)_4NHAc)$—$C(=O)$—$NH$—$(CH_2)_4CH(NH_2)$—$C(=O)$—$^b$ or $^a$—$NHCH((CH_2)_4NHHeptanoyl)$-$C(=)$—$NH$—$(CH_2)_4CH(NH_2)$—$C(=O)$—$^b$.

42. The compound or salt thereof according to claim 36, wherein $Q^3$ is $^a$—$NH(CH_2)_4$—$C(=O)$—$NH$—$(CH_2)_4C^{(S)}H(NH_2)$—$C(=O)$—$^b$, $^a$—$NHC^{(S)}H((CH_2)_4NH_2)$—$C(=O)$—$NH$—$(CH_2)_4C^{(S)}H(NH_2)$—$C(=O)$—$^b$, $^a$—$NHC^{(S)}H((CH_2)_4NHAc)$—$C(=O)$—$NH$—$(CH_2)_4C^{(S)}H(NH_2)$—$C(=O)$—$^b$, $^a$—$NHC^{(S)}H((CH_2)_4NHAc)$—$C(=O)$—$NH$—$(CH_2)_4C^{(R)}H(NH_2)$—$C(=O)$—$^b$ or $^a$—$NHC^{(S)}H((CH_2)_4NHHeptanoyl)$-$C(=O)$—$NH$—$(CH_2)_4C^{(S)}H(NH_2)$—$C(=O)$—$^b$.

43. The compound or salt thereof according to claim 1, wherein Q is $Q^2$.

44. The compound or salt thereof according to claim 43, wherein n is 0, 1, 2 or 3.

45. The compound or salt thereof according to claim 44, wherein $Q^2$ is $^a$—$NH(CH_2)_4$—$^b$, $^a$—$NH(CH_2)_5$—$^b$, $^a$—$NH(CH_2)_6$—$^b$, $^a$—$C(=O)$—$(CH_2)_3$—$^b$ or $^a$—$C(=O)$—$(CH_2)_5$—$^b$.

46. The compound or salt thereof according to claim 1, wherein Q is $Q^4$.

47. The compound or salt thereof according to claim 46, wherein n is 1, 2 or 3.

48. The compound or salt thereof according to claim 46, wherein r is 1, 2 or 3.

49. The compound or salt thereof according to claim 46, wherein $Q^4$ is $^a$—NH—$(CH_2)_2$—C(=O)—NH—$(CH_2)_5$—$^b$, $^a$—NH—$(CH_2)_4$—C(=O)—NH—$(CH_2)_6$—$^b$, $^a$—C(=O)—$(CH_2)_2$—C(=O)—NH—$(CH_2)_6$—$^b$ or $^a$—C(=O)—$(CH_2)_3$—C(=O)—NH—$(CH_2)_4$—$^b$.

50. The compound or salt thereof according to claim 1, wherein:
$R^1$ is $(C_1$-$C_{10})$alkyl, $(C_5$-$C_7)$cycloalkyl or $Ar^1$—$CH_2$—;
$R^2$ is $(C_1$-$C_6)$alkoxy;
$R^3$ is selected from $(C_1$-$C_6)$alkyl and $Ar^3$—$CH_2$—, wherein $Ar^3$ is phenyl or halo-substituted phenyl;
$R^4$ is selected from $(C_1$-$C_6)$alkyl, —$(CH_2)$—$OR^{4a}$, —$(CH_2)_{2-4}$—$NR^{4a}_2$, —$(CH_2)_{1-3}$—C(=O)$NR^{4a}_2$, —$(CH_2)_{2-4}$—$NR^{4a}$C(=O)$NR^{4a}_2$, —$(CH_2)_{2-4}$—$NR^{4a}$C(=$NR^{4a}$)$NR^{4a}_2$ and —$(CH_2)$—$Ar^4$
each $R^{4a}$ is hydrogen or methyl;
$Ar^4$ is imidazolyl or indolyl;
$R^5$ is selected from —$(CH_2)_{1-6}$—$NR^{5a}_2$ and —$(CH_2)_{1-6}$—$NR^{5a}$C(=$NR^{5a}$)$NR^{5a}_2$;
each $R^{5a}$ is independently selected from hydrogen and methyl;
$R^6$ is hydrogen or —C(=NH)$NH_2$;
$R^7$ is $(C_1$-$C_6)$alkyl or $(C_4$-$C_7)$cycloalkyl;
$R^9$ is selected from —$(CH_2)_{1-6}$—$NR^{9a}_2$ and —$(CH_2)_{1-6}$—$NR^{9a}$C(=O)$R^{9b}$;
each $R^{9a}$ is hydrogen;
each $R^{9b}$ is hydrogen or $(C_1$-$C_6)$alkyl;
$R^{10}$ is selected from —$(CH_2)_{1-6}$—C(=O)$NR^{10a}_2$ and $Ar^{10}$—$CH_2$—;
each $R^{10a}$ is hydrogen or methyl;
$Ar^{10}$ is pyridyl;
Ar is phenyl;
m is 0, 1, 2, 3 or 4;
n is 0, 1, 2 or 3
o is 1 or 2
p is 1, 2 or 3; and
r is 0, 1, 2 or 3.

51. The compound or salt thereof according to claim 1, wherein:
$R^1$ is isobutyl, n-hexyl, cyclohexyl or benzyl;
$R^2$ is methoxy;
$R^3$ is selected from s-butyl, neopentyl, benzyl and 4-chlorobenzyl;
$R^4$ is selected from Me, sobutyl, —$CH_2OH$, —$(CH_2)_2$—$NH_2$, —$(CH_2)_3$—$NH_2$, —$(CH_2)_4$—$NH_2$, —$(CH_2)_2$—C(=O)$NH_2$, —$(CH_2)_3$—NHC(=NH)$NH_2$, —$(CH_2)_3$—NHC(=O)$NH_2$ and —$CH_2$(1H-imidazol-4-yl);
$R^5$ is —$(CH_2)_2$—$NH_2$, —$(CH_2)_3$—$NH_2$, —$(CH_2)_4$—$NH_2$ or —$(CH_2)_3$—NHC(=NH)$NH_2$;
$R^7$ is s-butyl;
$R^{10}$ is selected from 1-hydroxyethyl, —$(CH_2)_2$—C(=O)$NH_2$ and 3-pyridyl-$CH_2$—;
Ar is phenyl;
$Q^1$ is $^a$—NH$(CH_2)_4C^{(S)}$H$(NH_2)$—C(=O)—$^b$, $^a$—NH$(CH_2)_4C^{(S)}$H(NHC(=NH)$NH_2$)—C(=O)—$^b$ or $^a$—C(=O)$(CH_2)_2C^{(S)}$H$(NH_2)$—C(=O)—$^b$ or $^a$—C(=O)$(CH_2)_2C^{(R)}$H$(NH_2)$—C(=O)—$^b$;
$Q^2$ is $^a$—NH$(CH_2)_4$—$^b$, $^a$—NH$(CH_2)_5$—$^b$, $^a$—NH$(CH_2)_6$—$^b$, $^a$—C(=O)—$(CH_2)_3$—$^b$ or $^a$—C(=O)—$(CH_2)_5$—$^b$;
$Q^3$ is $^a$—NH$(CH_2)_4$—C(=O)—NH—$(CH_2)_4C^{(S)}$H$(NH_2)$—C(=O)—$^b$, $^a$—NHC$^{(S)}$H$((CH_2)_4NH_2)$—C(=O)—NH—$(CH_2)_4C^{(S)}$H$(NH_2)$—C(=O)—$^b$, $^a$—NHC$^{(S)}$H$((CH_2)_4NHAc)$—C(=O)—NH—$(CH_2)_4C^{(S)}$H$(NH_2)$—C(=O)—$^b$, $^a$—NHC$^{(S)}$H$((CH_2)_4NHAc)$—C(=O)—NH—$(CH_2)_4C^{(R)}$H$(NH_2)$—C(=O)—$^b$ or $^a$—NHC$^{(S)}$H$((CH_2)_4$NHHeptanoyl)-C(=O)—NH—$(CH_2)_4C^{(S)}$H$(NH_2)$—C(=O)—$^b$; and
$Q^4$ is $^a$—NH—$(CH_2)_2$—C(=O)—NH—$(CH_2)_5$—$^b$, $^a$—NH—$(CH_2)_4$—C(=O)—NH—$(CH_2)_6$—$^b$, $^a$—C(=O)—$(CH_2)_2$—C(=O)—NH—$(CH_2)_6$—$^b$ or $^a$—C(=O)—$(CH_2)_3$—C(=O)—NH—$(CH_2)_4$—$^b$.

52. A compound selected from compounds of the following formulae, and salts thereof:

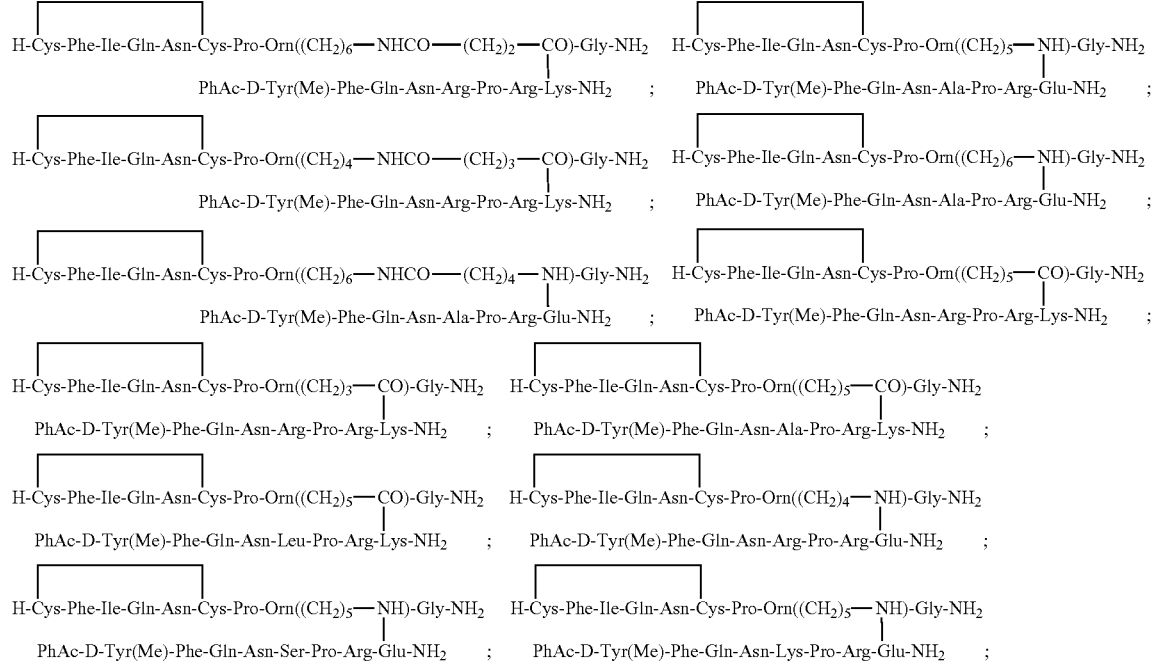

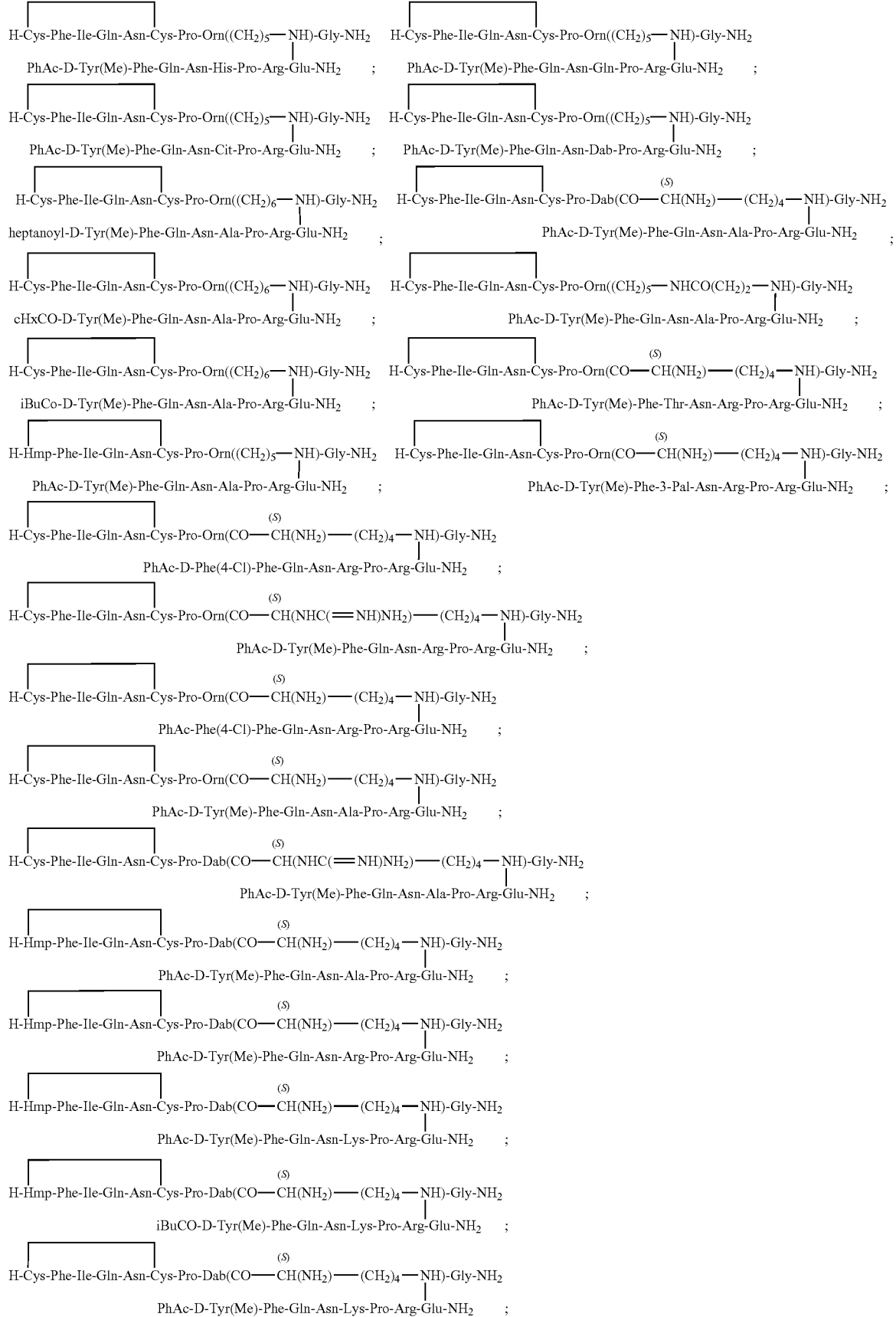

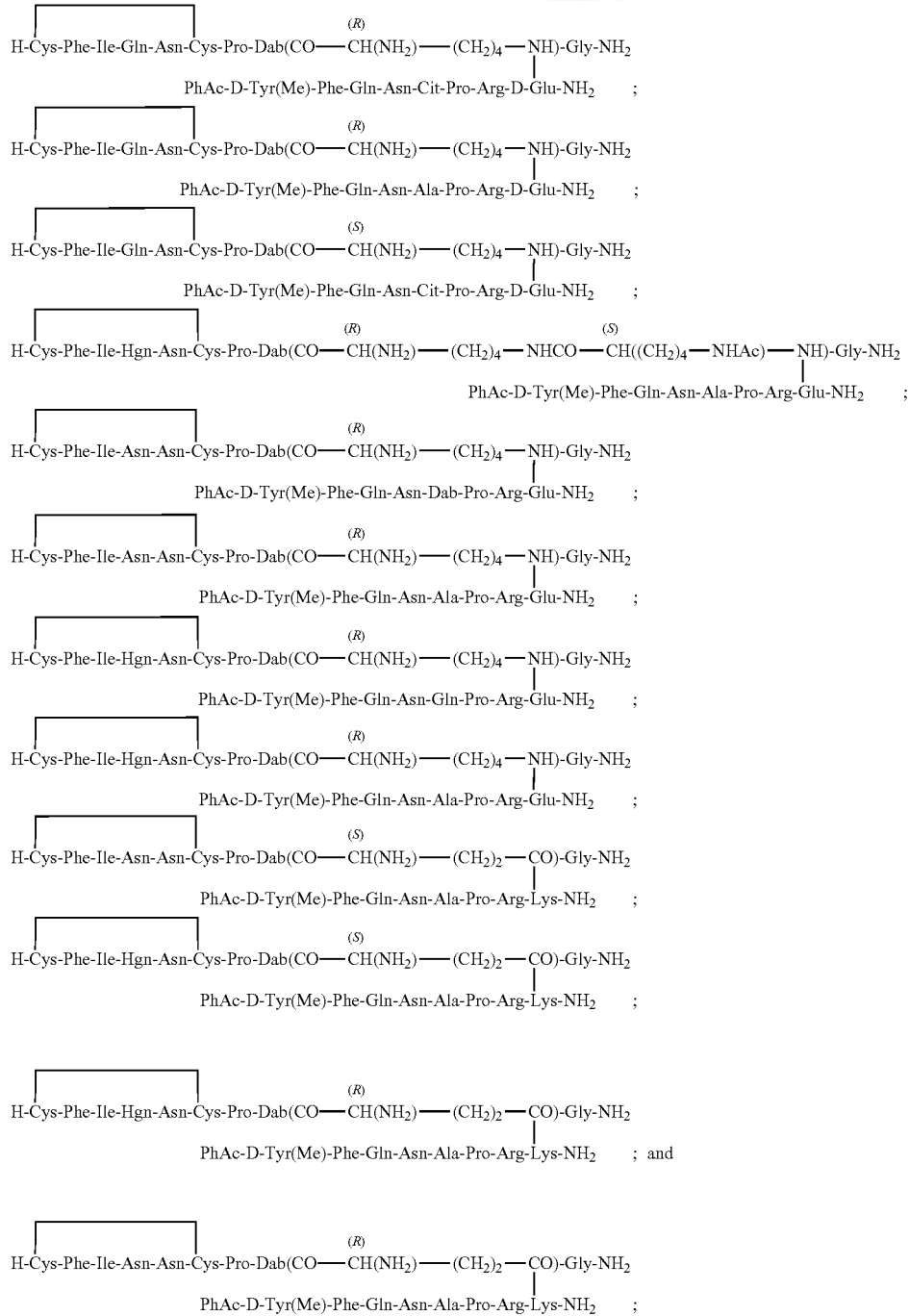
53. The compound or salt thereof according to claim 52, wherein the compound is a compound of the following formula:
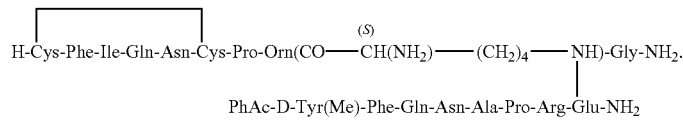

54. The compound or salt thereof according to claim 52, wherein the compound is a compound of the following formula:
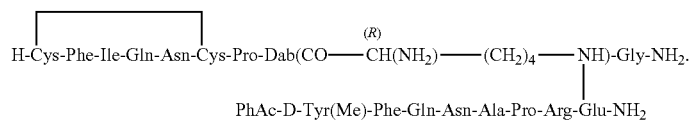
55. The compound or salt thereof according to claim 52, wherein the compound is a compound of the following formula:
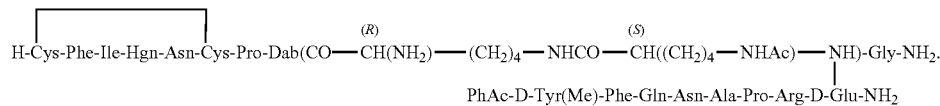
56. A compound or a salt thereof, wherein the compound is selected from compounds of the following structures:
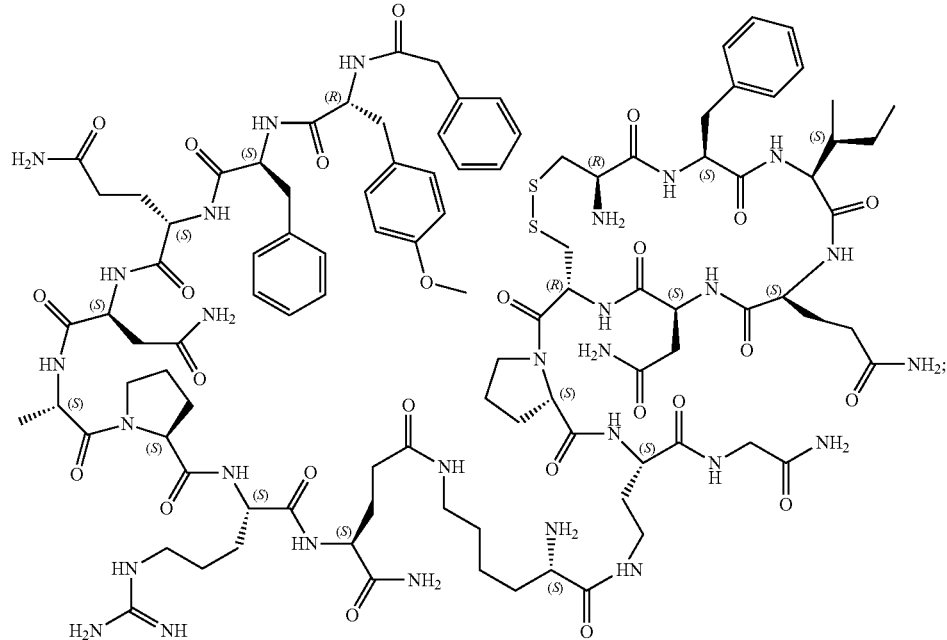

-continued
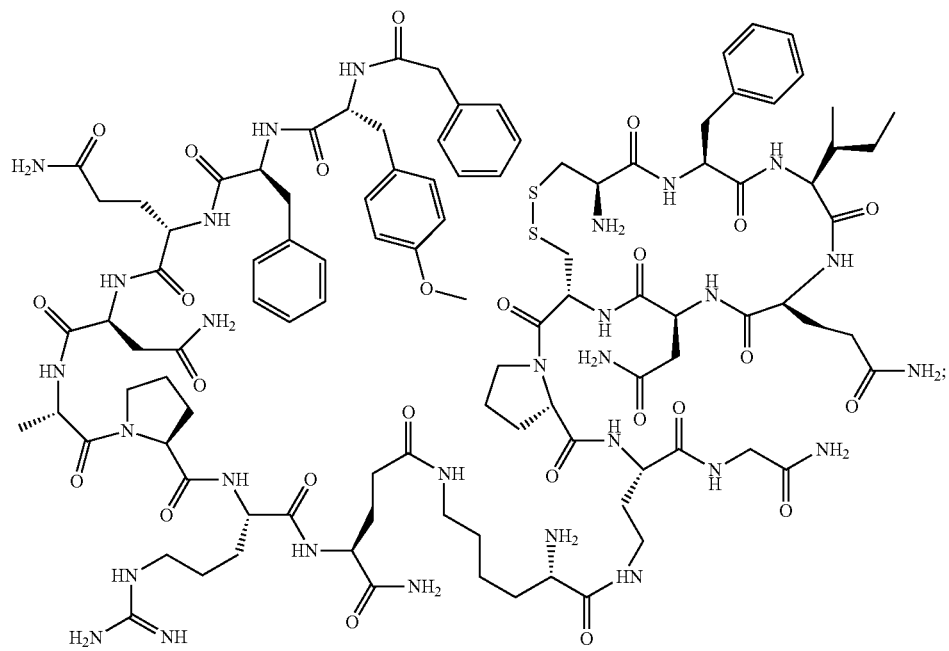
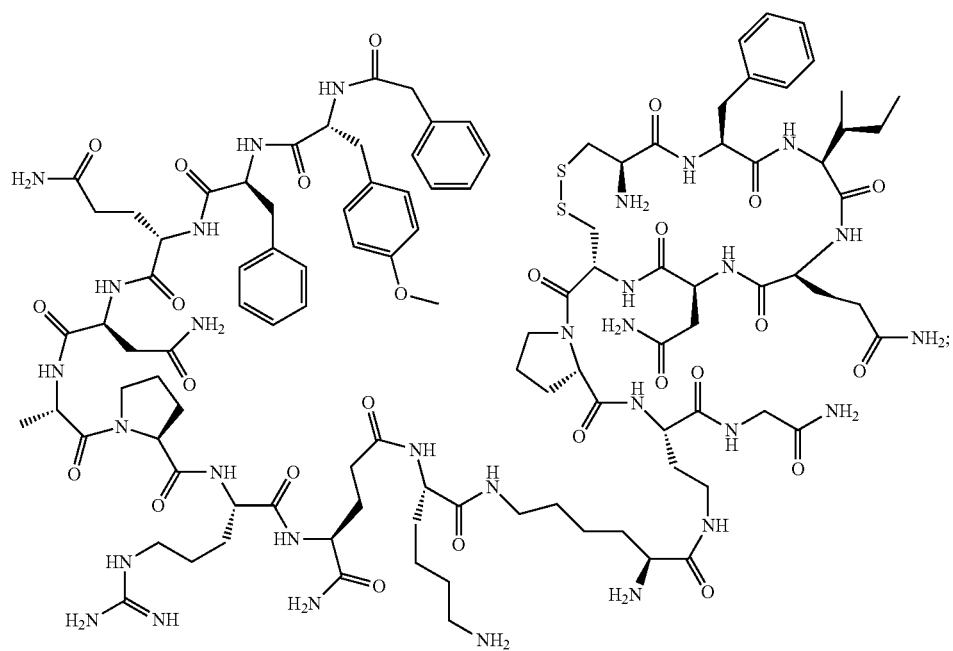

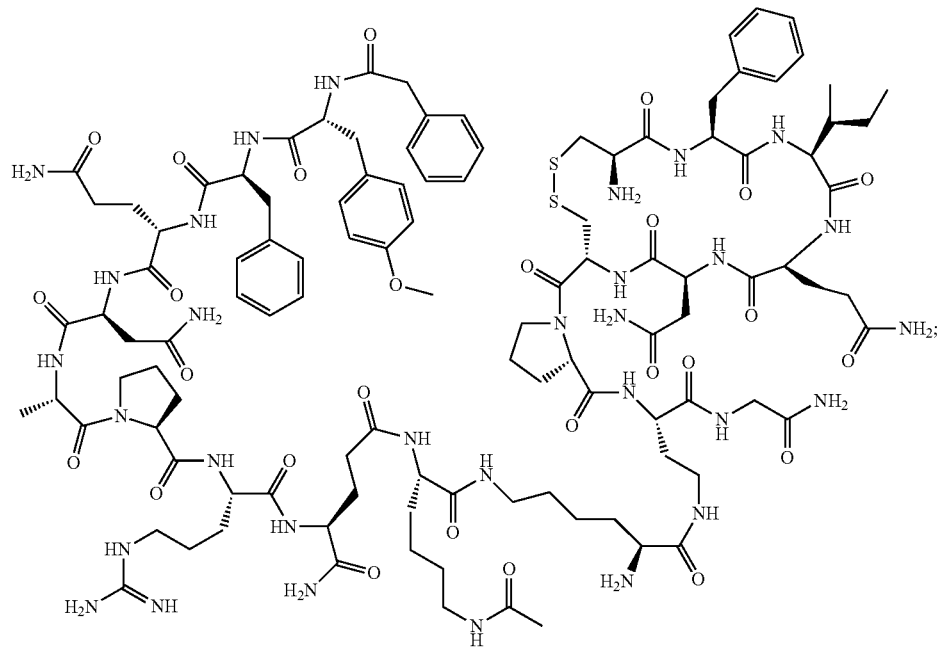
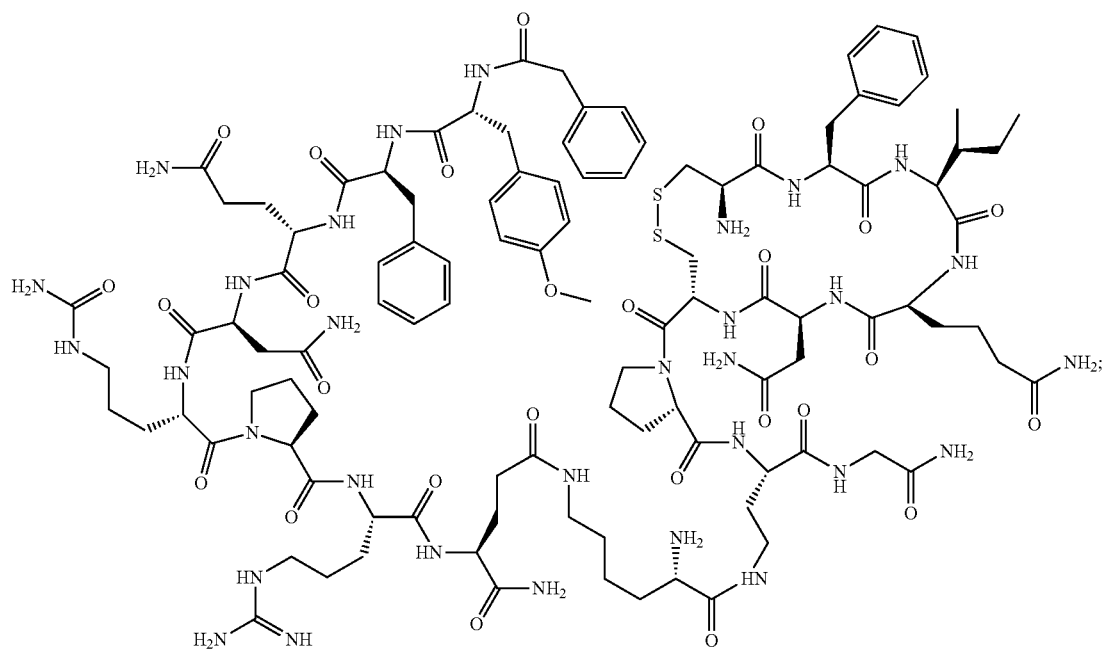

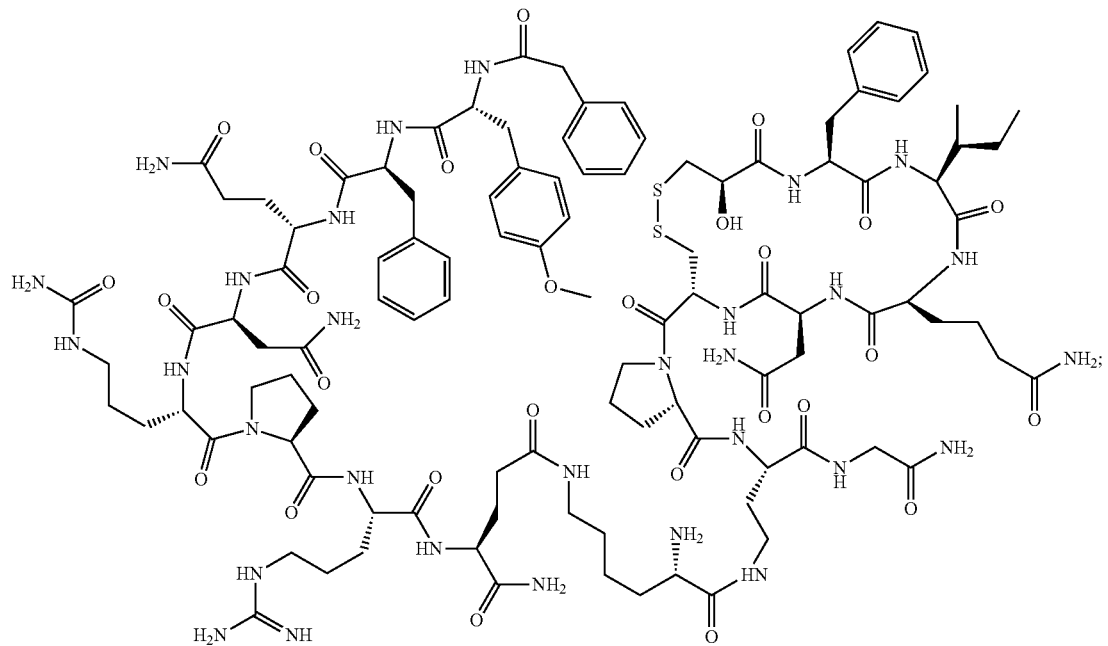
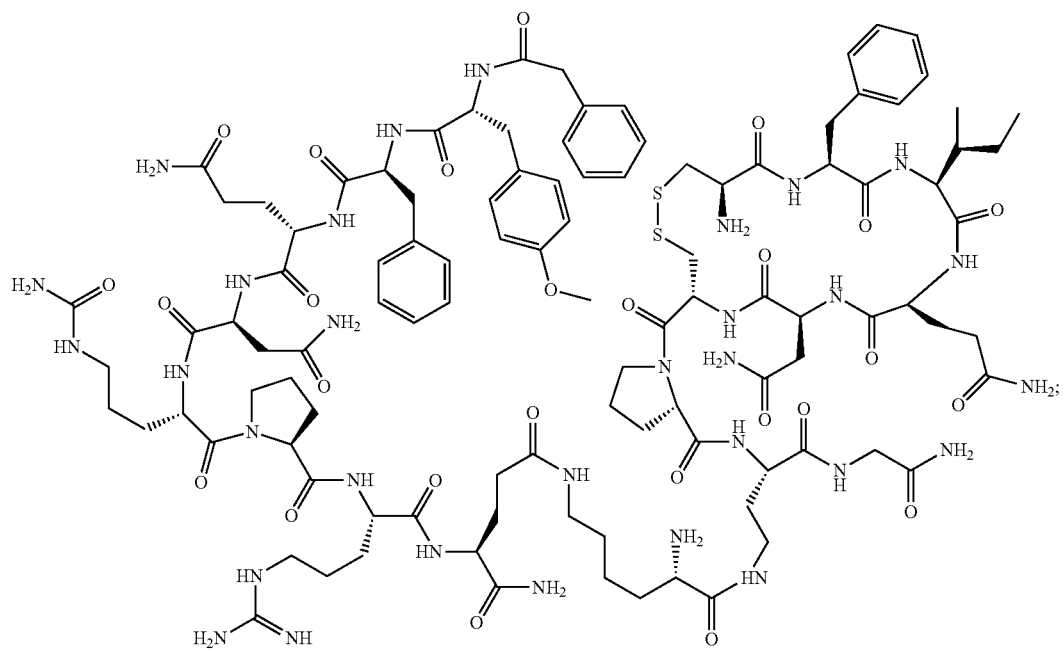

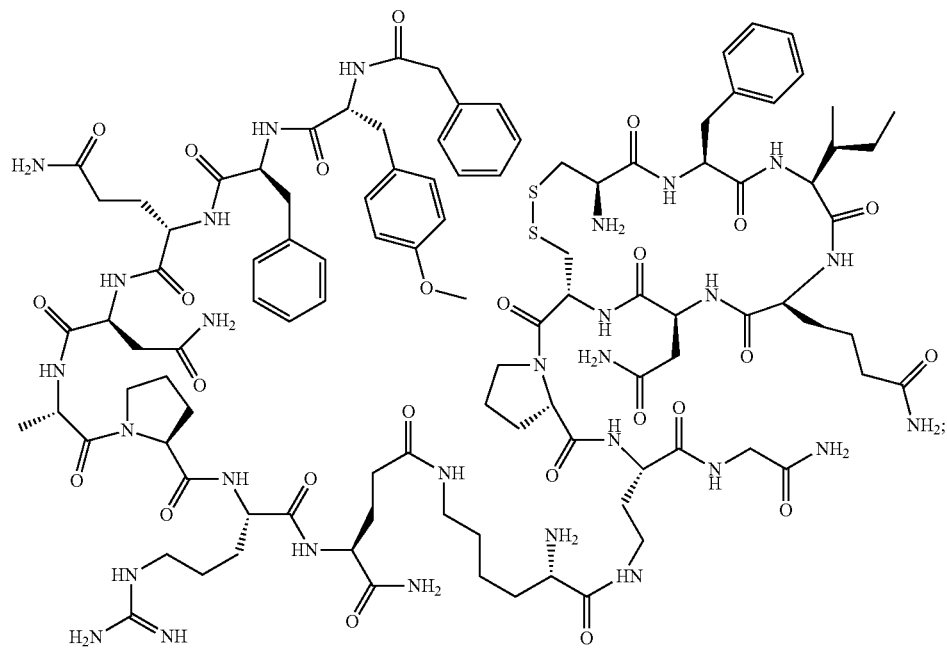
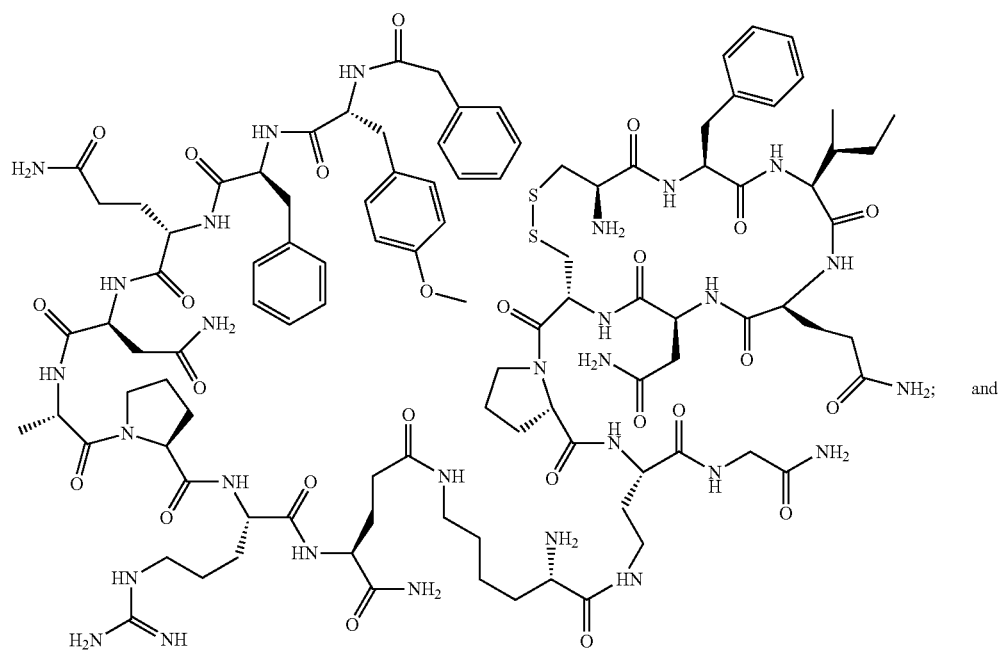
and

-continued
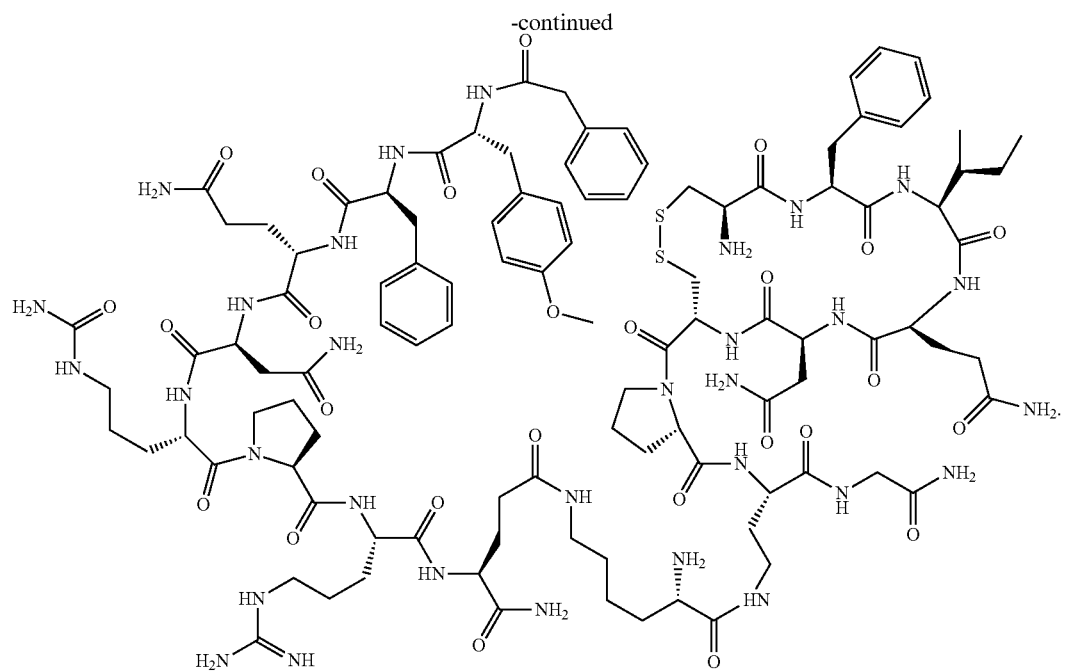
57. The compound or salt thereof according to claim 56, wherein the compound is of the following structure:
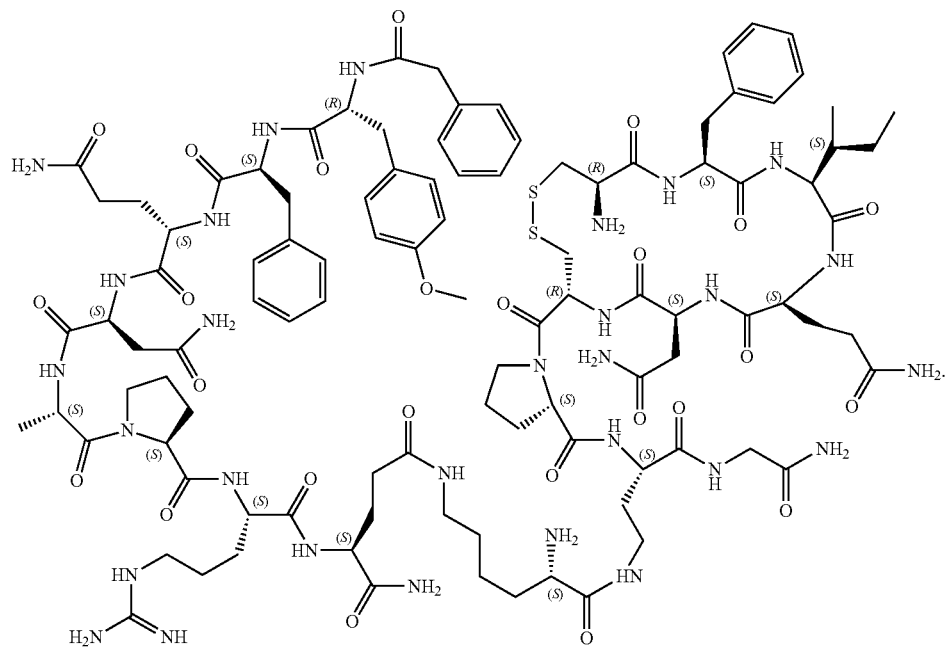

58. The compound or salt thereof according to claim 56, wherein the compound is of the following structure:
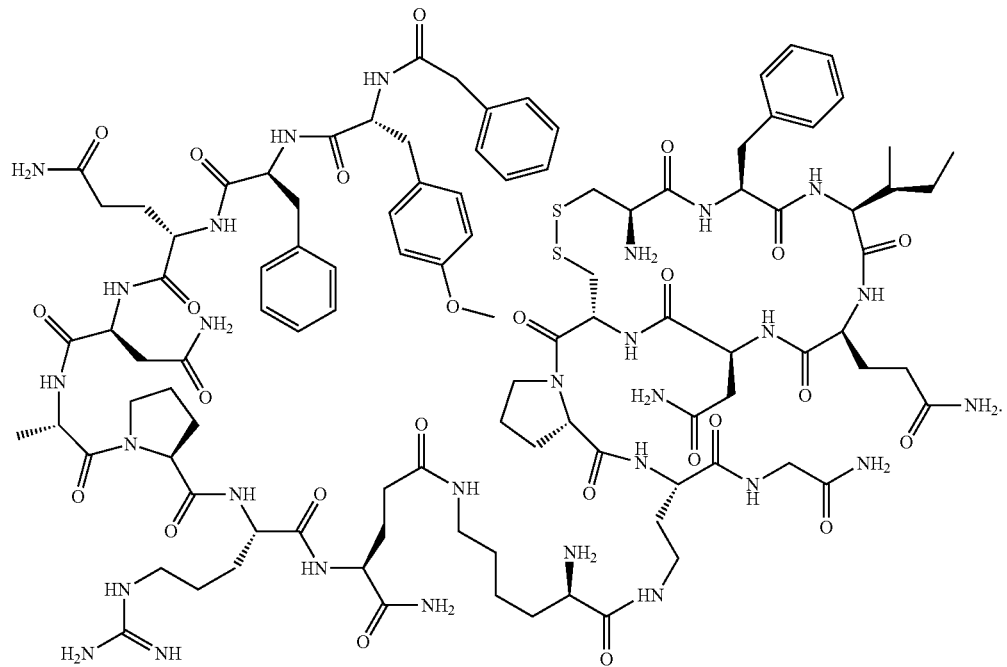 [SMILES: CC[C@H](C)[C@@H]1NC(=O)[C@H](Cc2ccccc2)NC(=O)[C@@H](N)CSSC[C@@H](C(=O)N2CCC[C@H]2C(=O)N[C@@H](CCNC(=O)[C@H](N)CCCCNC(=O)CC[C@H](NC(=O)[C@H](CCCNC(=N)N)NC(=O)[C@@H]2CCCN2C(=O)[C@H](C)NC(=O)[C@H](CC(N)=O)NC(=O)[C@H](CCC(N)=O)NC(=O)[C@H](Cc2ccccc2)NC(=O)[C@@H](Cc2ccc(OC)cc2)NC(=O)Cc2ccccc2)C(N)=O)C(=O)NCC(N)=O)NC(=O)[C@H](CC(N)=O)NC(=O)[C@H](CCC(N)=O)NC1=O]
59. The compound or salt thereof according to claim 56, wherein the compound is of the following structure:
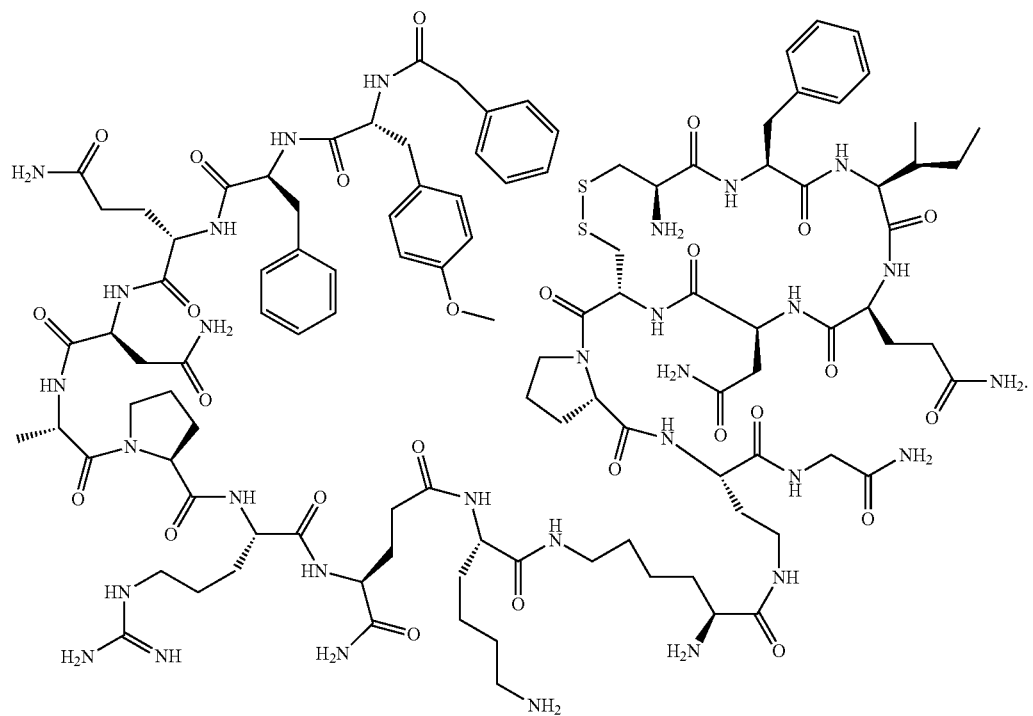 [SMILES: CC[C@H](C)[C@@H]1NC(=O)[C@H](Cc2ccccc2)NC(=O)[C@@H](N)CSSC[C@@H](C(=O)N2CCC[C@H]2C(=O)N[C@@H](CCNC(=O)[C@@H](N)CCCCNC(=O)[C@H](CCCCN)NC(=O)CC[C@H](NC(=O)[C@H](CCCNC(=N)N)NC(=O)[C@@H]2CCCN2C(=O)[C@H](C)NC(=O)[C@H](CC(N)=O)NC(=O)[C@H](CCC(N)=O)NC(=O)[C@H](Cc2ccccc2)NC(=O)[C@@H](Cc2ccc(OC)cc2)NC(=O)Cc2ccccc2)C(N)=O)C(=O)NCC(N)=O)NC(=O)[C@H](CC(N)=O)NC(=O)[C@H](CCC(N)=O)NC1=O]

60. The compound or salt thereof according to claim 56, wherein the compound is of the following structure:
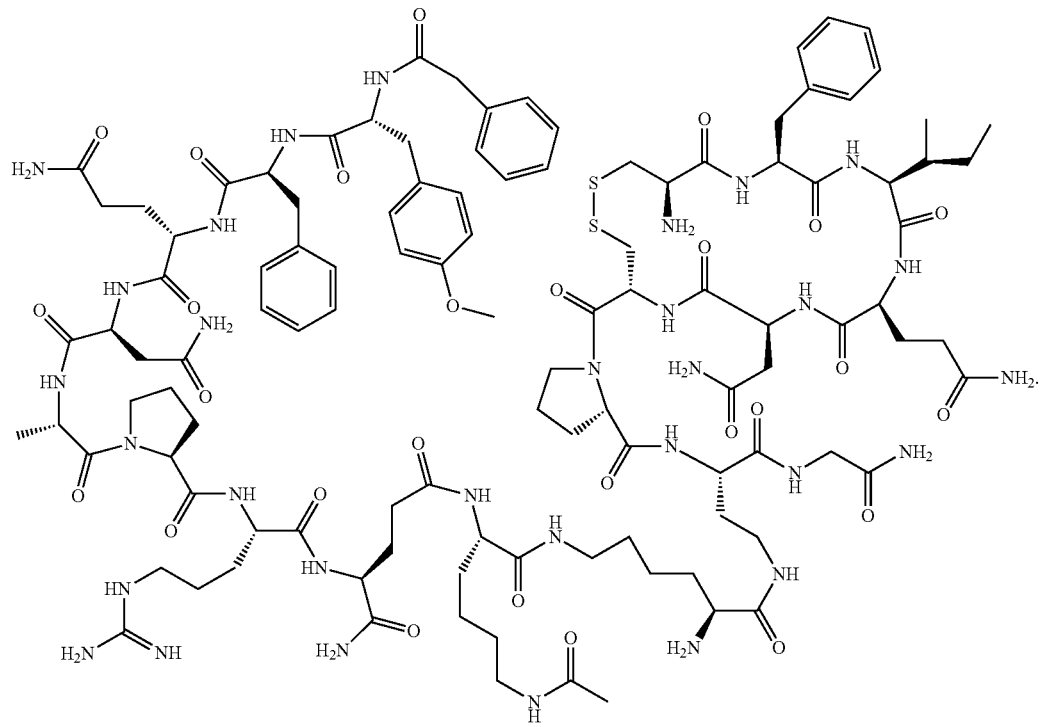 [SMILES: CC[C@H](C)[C@@H]1NC(=O)[C@H](Cc2ccccc2)NC(=O)[C@@H](N)CSSC[C@@H](C(=O)N2CCC[C@H]2C(=O)N[C@@H](CCNC(=O)[C@@H](N)CCCCNC(=O)[C@H](CCCCNC(C)=O)NC(=O)CC[C@H](NC(=O)[C@H](CCCNC(=N)N)NC(=O)[C@@H]2CCCN2C(=O)[C@H](C)NC(=O)[C@H](CC(N)=O)NC(=O)[C@H](CCC(N)=O)NC(=O)[C@H](Cc2ccccc2)NC(=O)[C@@H](Cc2ccc(OC)cc2)NC(=O)Cc2ccccc2)C(N)=O)C(=O)NCC(N)=O)NC(=O)[C@H](CC(N)=O)NC(=O)[C@H](CCC(N)=O)NC1=O]
61. The compound or salt thereof according to claim 56, wherein the compound is of the following structure:
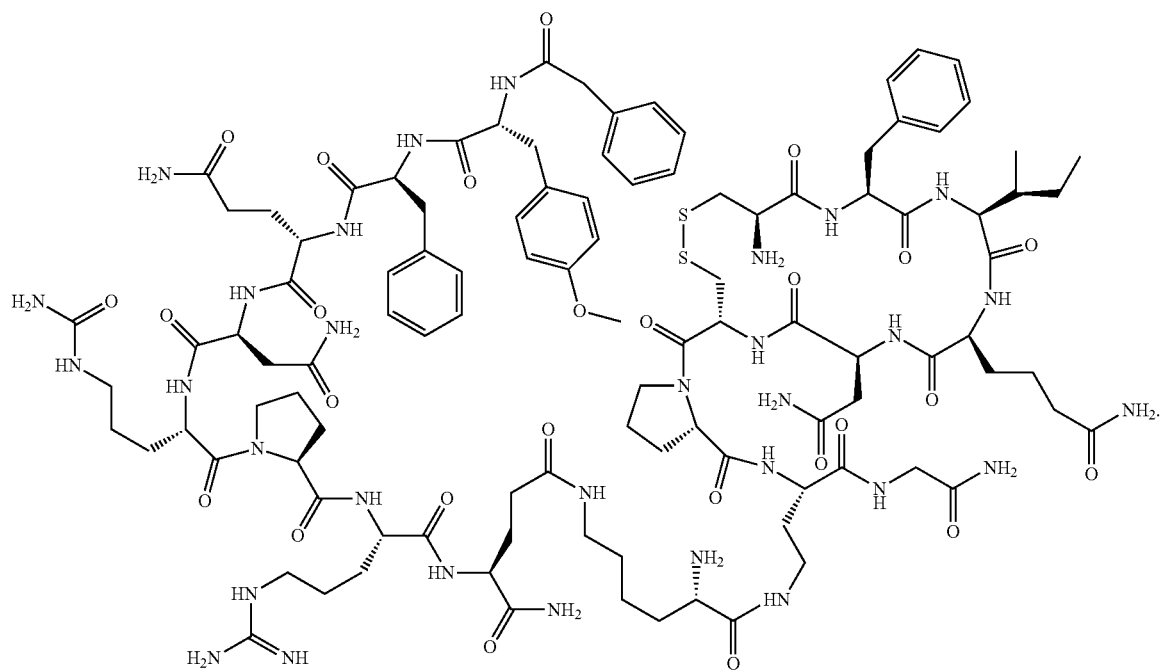 [SMILES: CC[C@H](C)[C@@H]1NC(=O)[C@H](Cc2ccccc2)NC(=O)[C@@H](N)CSSC[C@@H](C(=O)N2CCC[C@H]2C(=O)N[C@@H](CCNC(=O)[C@@H](N)CCCCNC(=O)CC[C@H](NC(=O)[C@H](CCCNC(=N)N)NC(=O)[C@@H]2CCCN2C(=O)[C@H](CCCNC(N)=O)NC(=O)[C@H](CC(N)=O)NC(=O)[C@H](CCC(N)=O)NC(=O)[C@H](Cc2ccccc2)NC(=O)[C@@H](Cc2ccc(OC)cc2)NC(=O)Cc2ccccc2)C(N)=O)C(=O)NCC(N)=O)NC(=O)[C@H](CC(N)=O)NC(=O)[C@H](CCCC(N)=O)NC1=O]

62. The compound or salt thereof according to claim 56, wherein the compound is of the following structure:
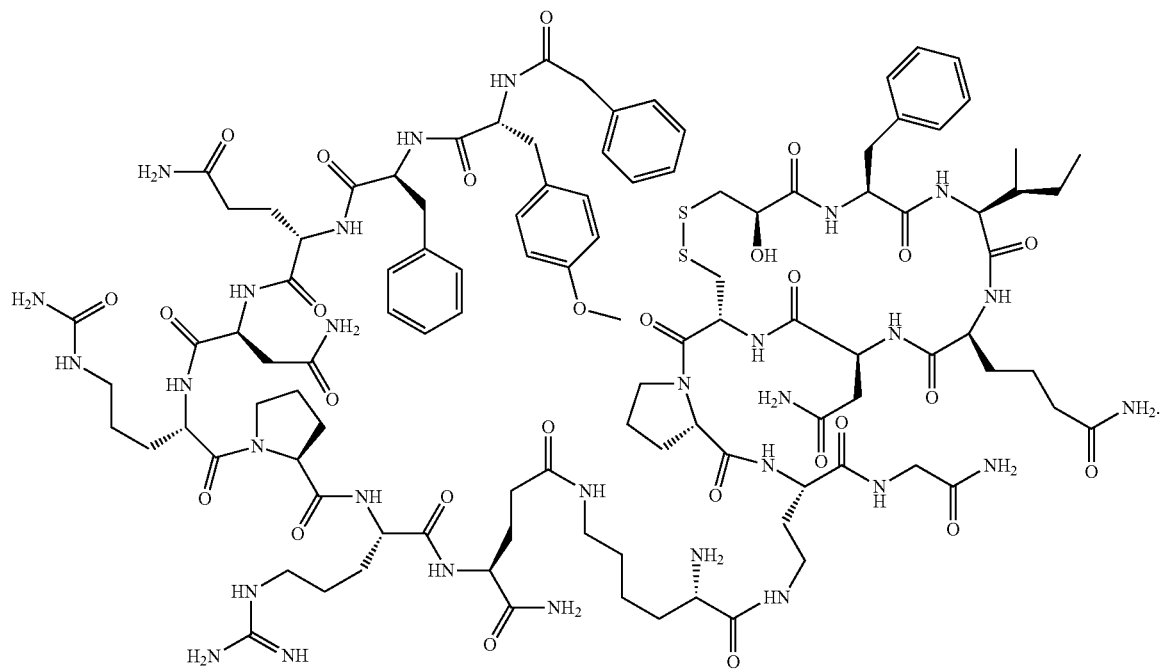 [SMILES: CC[C@H](C)[C@@H]1NC(=O)[C@H](Cc2ccccc2)NC(=O)[C@@H](O)CSSC[C@@H](C(=O)N2CCC[C@H]2C(=O)N[C@@H](CCNC(=O)[C@@H](N)CCCCNC(=O)CC[C@H](NC(=O)[C@H](CCCNC(=N)N)NC(=O)[C@@H]2CCCN2C(=O)[C@H](CCCNC(N)=O)NC(=O)[C@H](CC(N)=O)NC(=O)[C@H](CCC(N)=O)NC(=O)[C@H](Cc2ccccc2)NC(=O)[C@@H](Cc2ccc(OC)cc2)NC(=O)Cc2ccccc2)C(N)=O)C(=O)NCC(N)=O)NC(=O)[C@H](CC(N)=O)NC(=O)[C@H](CCCC(N)=O)NC1=O]
63. The compound or salt thereof according to claim 56, wherein the compound is of the following structure:
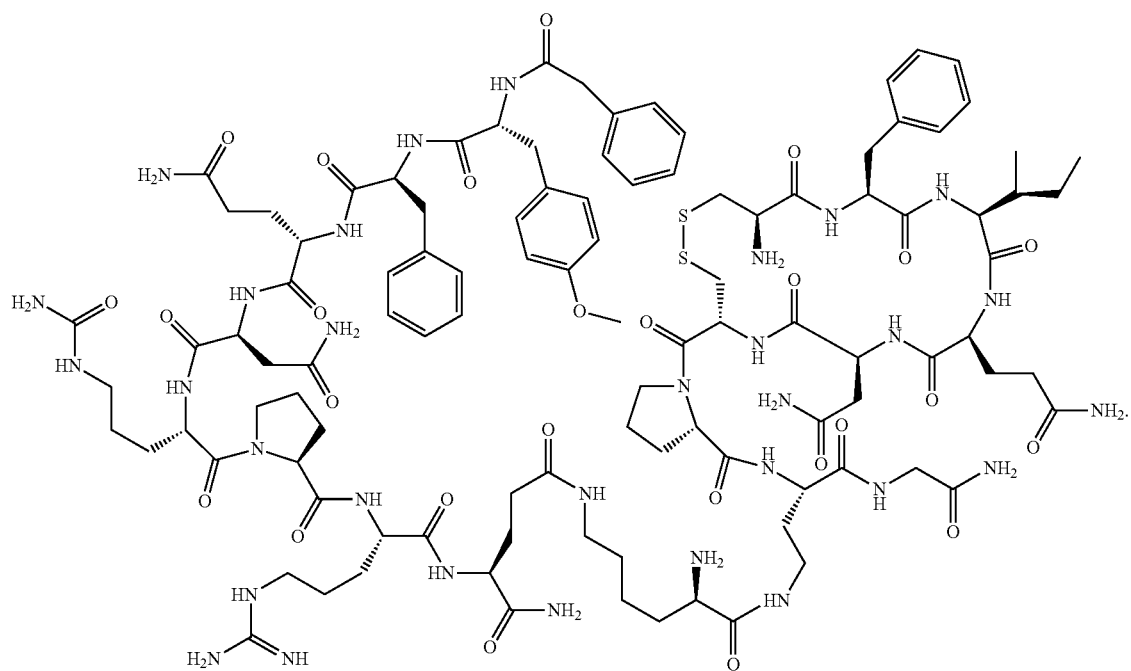 [SMILES: CC[C@H](C)[C@@H]1NC(=O)[C@H](Cc2ccccc2)NC(=O)[C@@H](N)CSSC[C@@H](C(=O)N2CCC[C@H]2C(=O)N[C@@H](CCNC(=O)[C@H](N)CCCCNC(=O)CC[C@H](NC(=O)[C@H](CCCNC(=N)N)NC(=O)[C@@H]2CCCN2C(=O)[C@H](CCCNC(N)=O)NC(=O)[C@H](CC(N)=O)NC(=O)[C@H](CCC(N)=O)NC(=O)[C@H](Cc2ccccc2)NC(=O)[C@@H](Cc2ccc(OC)cc2)NC(=O)Cc2ccccc2)C(N)=O)C(=O)NCC(N)=O)NC(=O)[C@H](CC(N)=O)NC(=O)[C@H](CCC(N)=O)NC1=O]

64. The compound or salt thereof according to claim 56, wherein the compound is of the following structure:
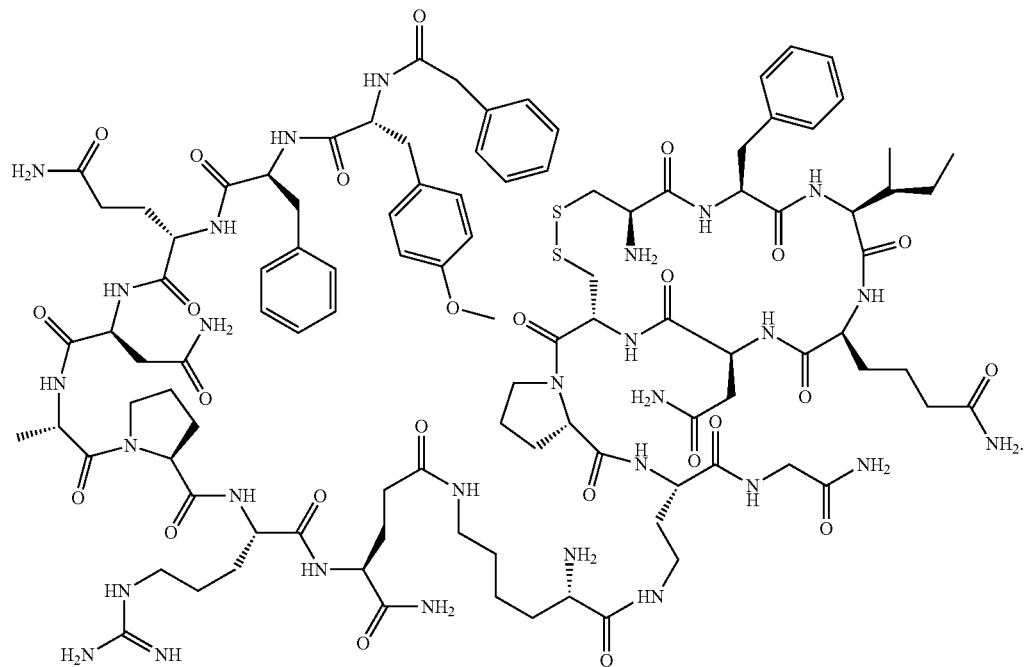 [SMILES: CC[C@H](C)[C@@H]1NC(=O)[C@H](Cc2ccccc2)NC(=O)[C@@H](N)CSSC[C@@H](C(=O)N2CCC[C@H]2C(=O)N[C@@H](CCNC(=O)[C@@H](N)CCCCNC(=O)CC[C@H](NC(=O)[C@H](CCCNC(=N)N)NC(=O)[C@@H]2CCCN2C(=O)[C@H](C)NC(=O)[C@H](CC(N)=O)NC(=O)[C@H](CCC(N)=O)NC(=O)[C@H](Cc2ccccc2)NC(=O)[C@@H](Cc2ccc(OC)cc2)NC(=O)Cc2ccccc2)C(N)=O)C(=O)NCC(N)=O)NC(=O)[C@H](CC(N)=O)NC(=O)[C@H](CCCC(N)=O)NC1=O]
65. The compound or salt thereof according to claim 56, wherein the compound is of the following structure:
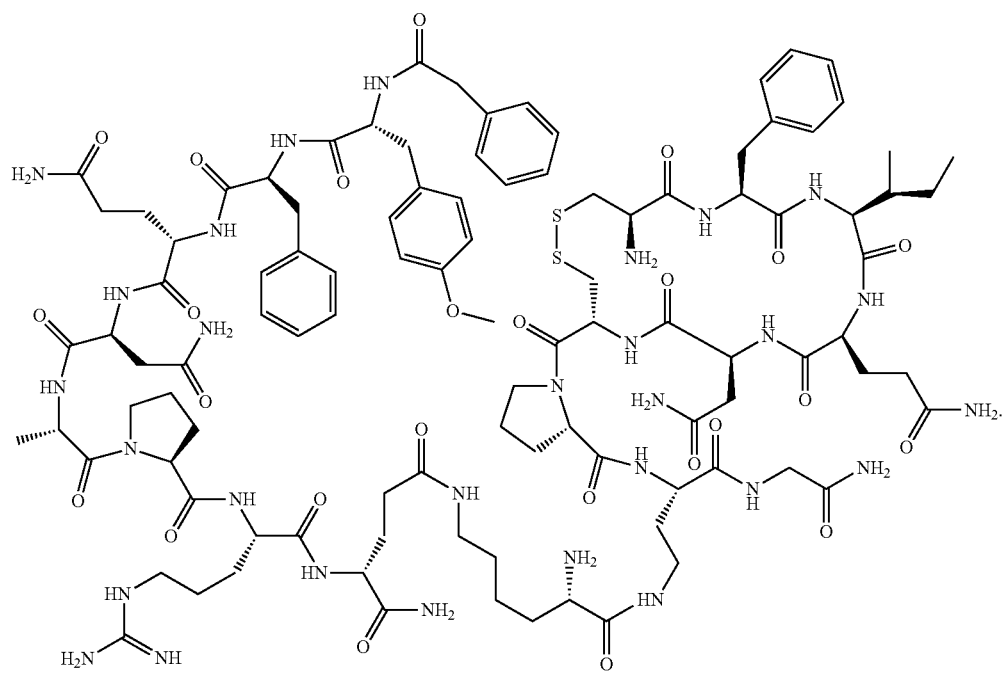 [SMILES: CC[C@H](C)[C@@H]1NC(=O)[C@H](Cc2ccccc2)NC(=O)[C@@H](N)CSSC[C@@H](C(=O)N2CCC[C@H]2C(=O)N[C@@H](CCNC(=O)[C@@H](N)CCCCNC(=O)CC[C@@H](NC(=O)[C@H](CCCNC(=N)N)NC(=O)[C@@H]2CCCN2C(=O)[C@H](C)NC(=O)[C@H](CC(N)=O)NC(=O)[C@H](CCC(N)=O)NC(=O)[C@H](Cc2ccccc2)NC(=O)[C@@H](Cc2ccc(OC)cc2)NC(=O)Cc2ccccc2)C(N)=O)C(=O)NCC(N)=O)NC(=O)[C@H](CC(N)=O)NC(=O)[C@H](CCC(N)=O)NC1=O]

66. The compound or salt thereof according to claim 56, wherein the compound is of the following structure:

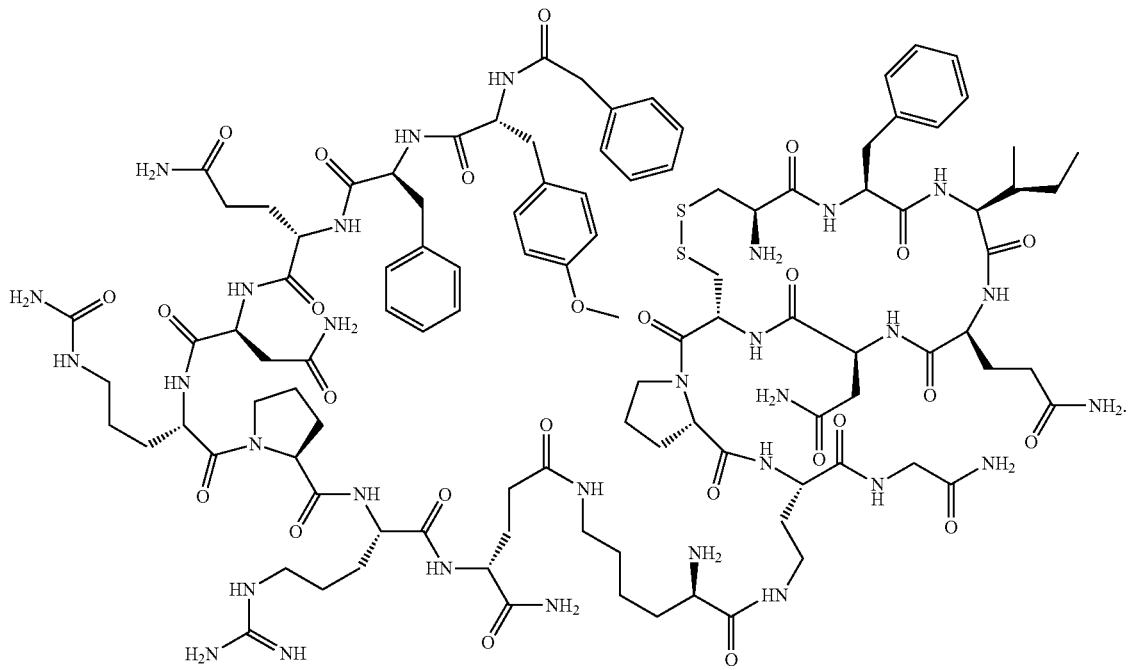 [SMILES: CC[C@H](C)[C@@H]1NC(=O)[C@H](Cc2ccccc2)NC(=O)[C@@H](N)CSSC[C@@H](C(=O)N2CCC[C@H]2C(=O)N[C@@H](CCNC(=O)[C@H](N)CCCCNC(=O)CC[C@@H](NC(=O)[C@H](CCCNC(=N)N)NC(=O)[C@@H]2CCCN2C(=O)[C@H](CCCNC(N)=O)NC(=O)[C@H](CC(N)=O)NC(=O)[C@H](CCC(N)=O)NC(=O)[C@H](Cc2ccccc2)NC(=O)[C@@H](Cc2ccc(OC)cc2)NC(=O)Cc2ccccc2)C(N)=O)C(=O)NCC(N)=O)NC(=O)[C@H](CC(N)=O)NC(=O)[C@H](CCC(N)=O)NC1=O]

67. A pharmaceutical composition comprising a compound according to claim 1, or a pharmaceutically acceptable salt thereof, and a pharmaceutically acceptable carrier.

68. A method of treating a complication arising from cirrhosis, wherein the complication is spontaneous bacterial peritonitis, type II hepatorenal syndrome (HRS2) or ascites, the method comprising administering to an individual in need of such treatment an effective amount of a compound according to claim 1, or a pharmaceutically acceptable salt thereof.

69. The method according to claim 68, wherein the complication is spontaneous bacterial peritonitis.

70. The method according to claim 68, wherein the complication is type II hepatorenal syndrome (HRS2).

71. The method according to claim 68, wherein the complication is refractory ascites.

72. A method of treatment of bleeding esophageal varices comprising administering to an individual in need of such treatment an effective amount of a compound according to claim 1, or a pharmaceutically acceptable salt thereof.

73. A method of treatment of type II hepatorenal syndrome comprising administering to an individual in need of such treatment an effective amount of a compound according to claim 1, or a pharmaceutically acceptable salt thereof.

74. A method of treatment of ascites comprising administering to an individual in need of such treatment an effective amount of a compound according to claim 1, or a pharmaceutically acceptable salt thereof.

75. The method according to claim 68, wherein the compound is a compound of one of the following structures:

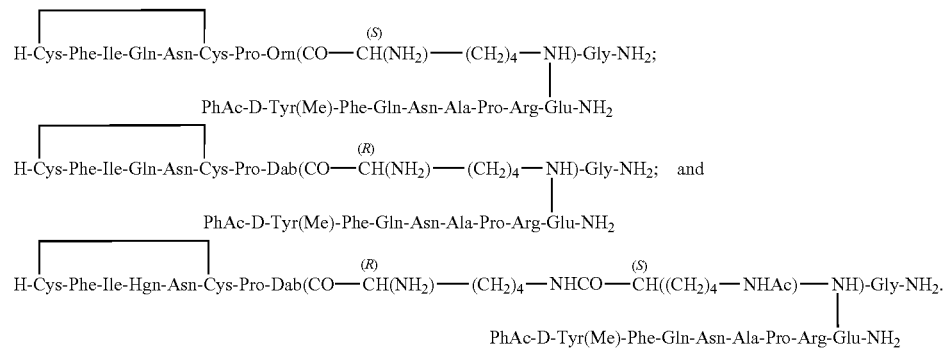

76. The method according to claim 68, wherein the compound is a compound of one of the following structures:

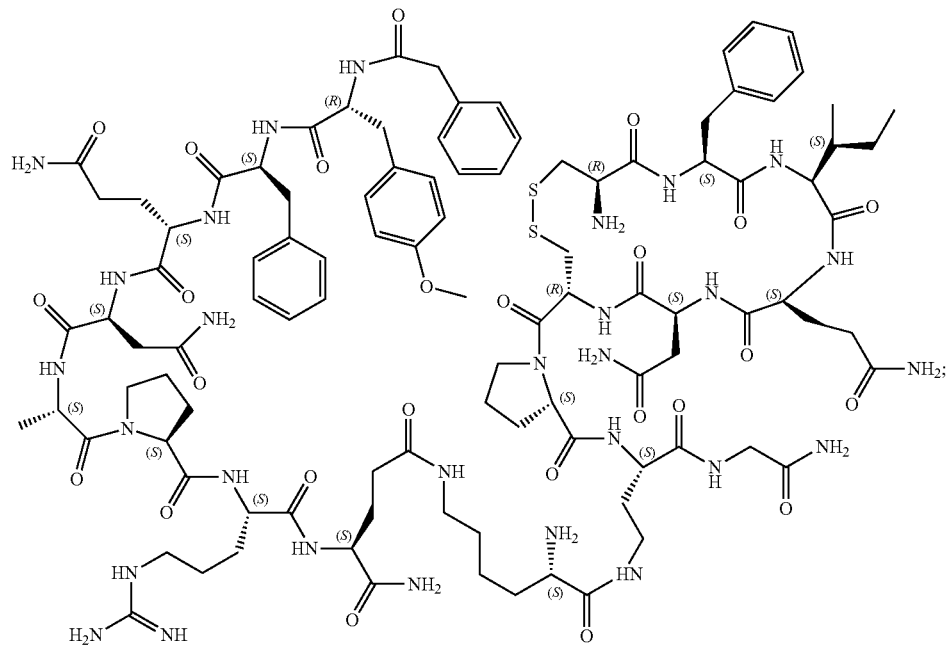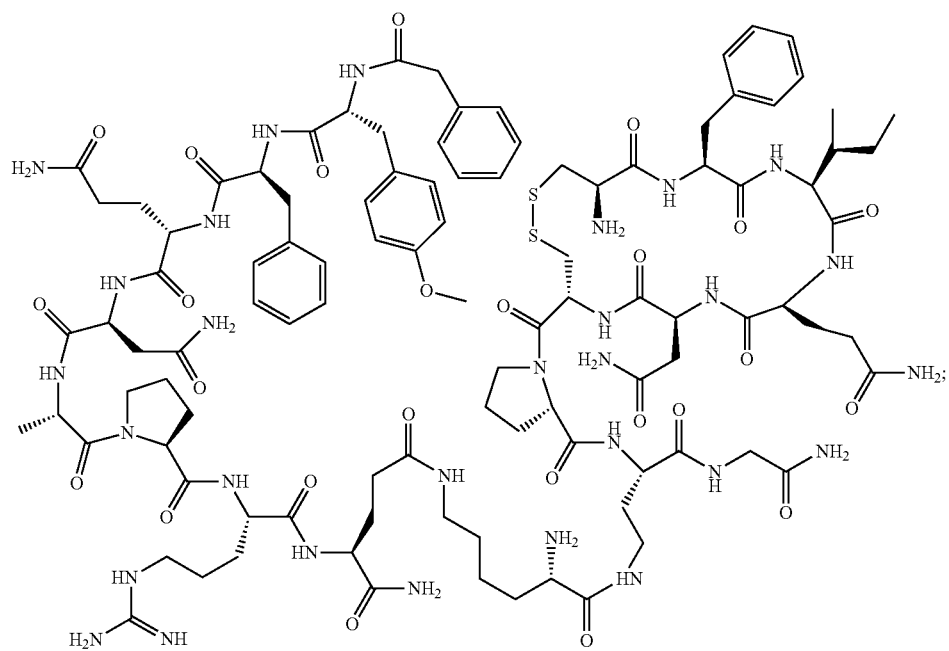

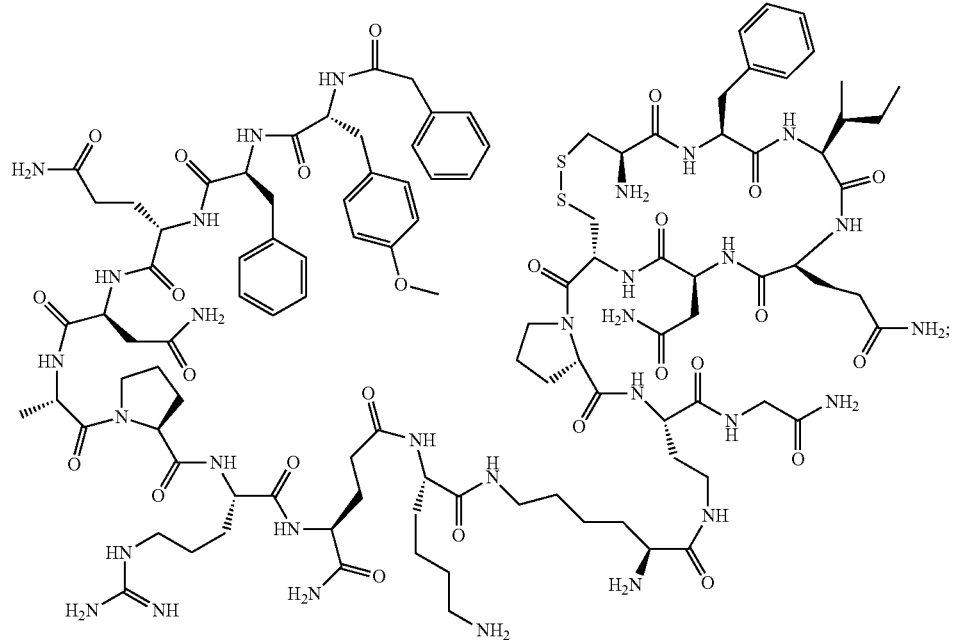
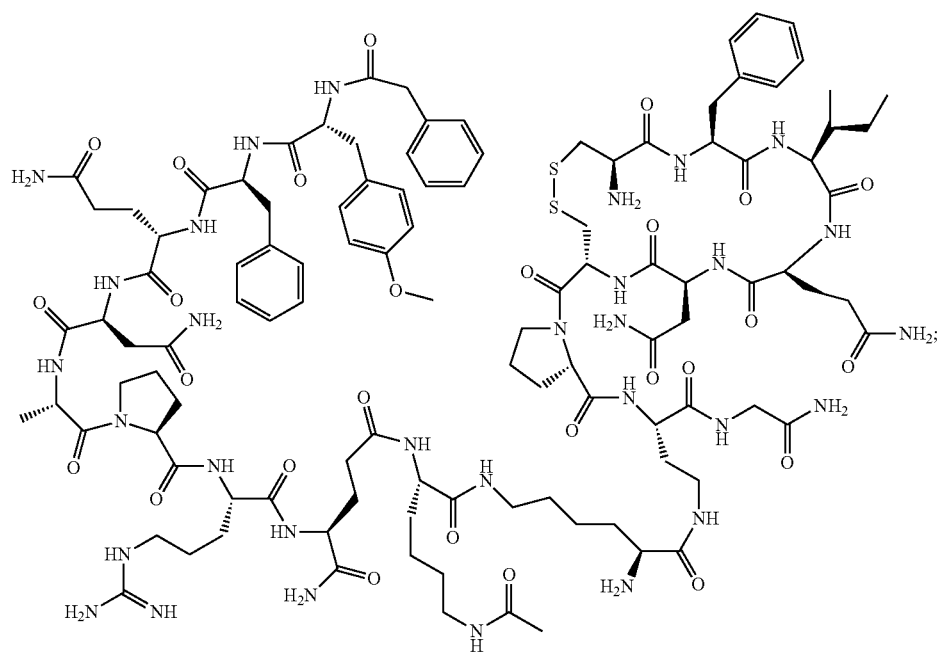

101
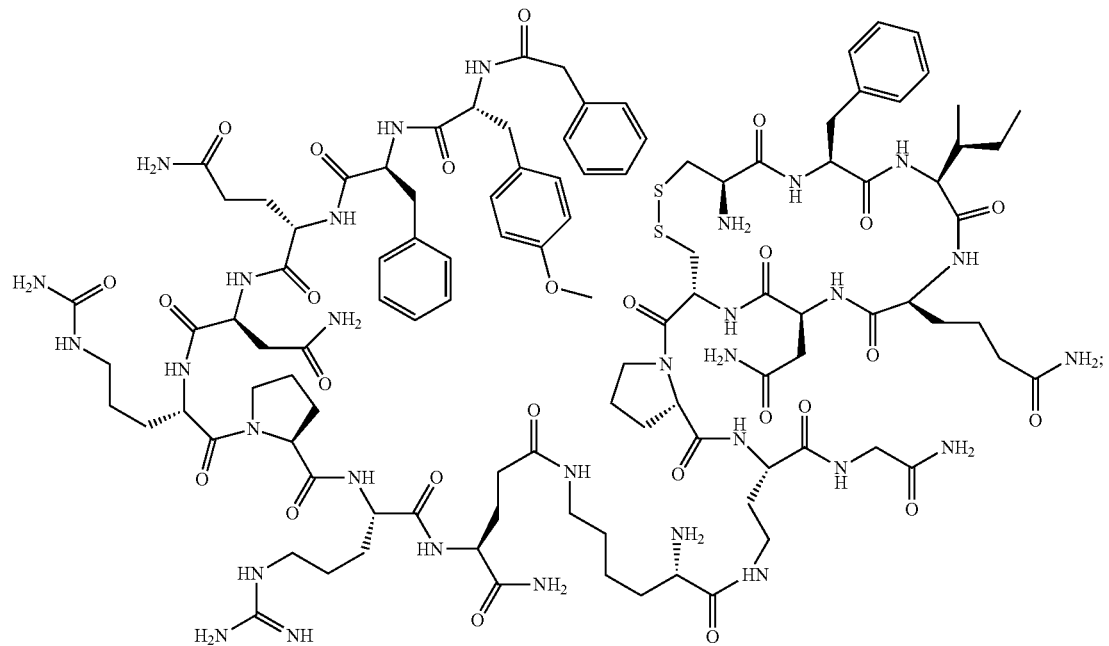
102
-continued
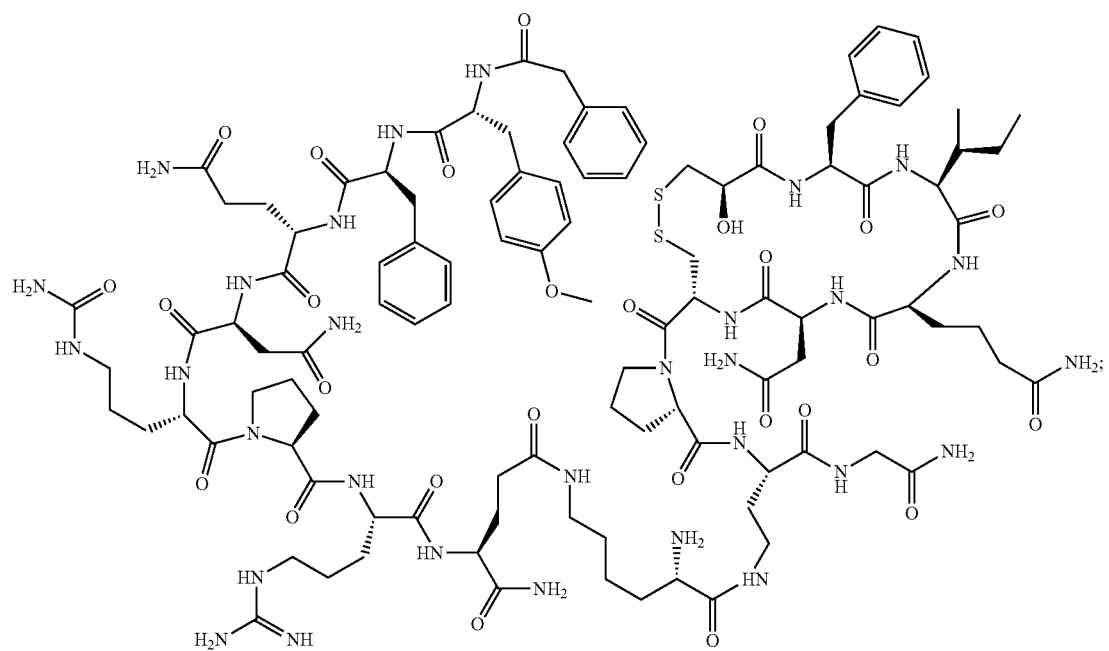

103
104
-continued
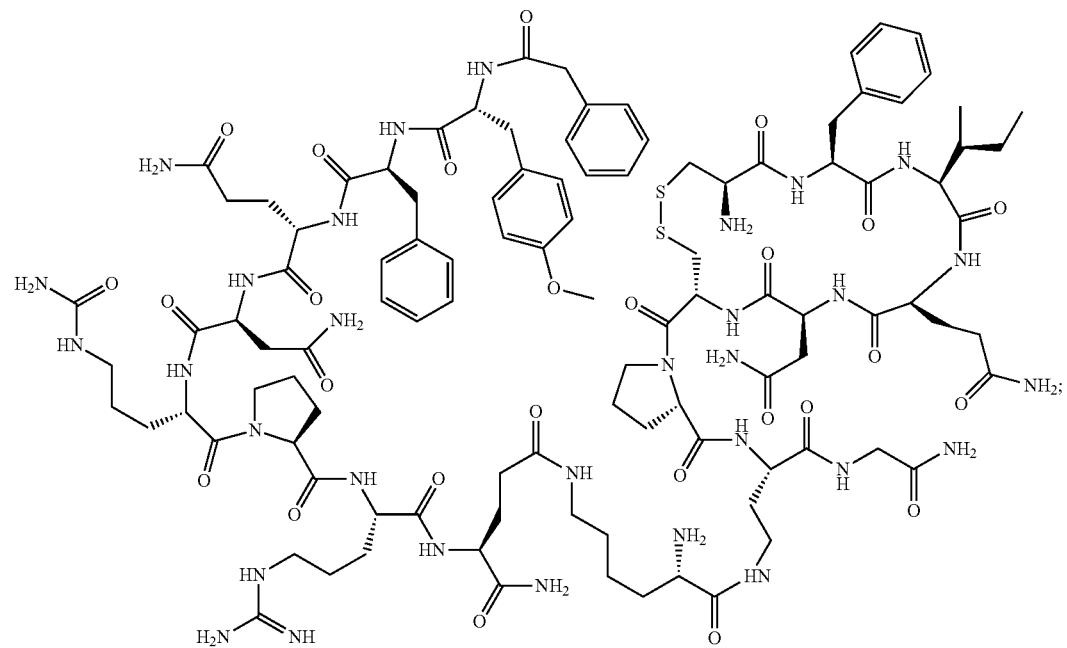
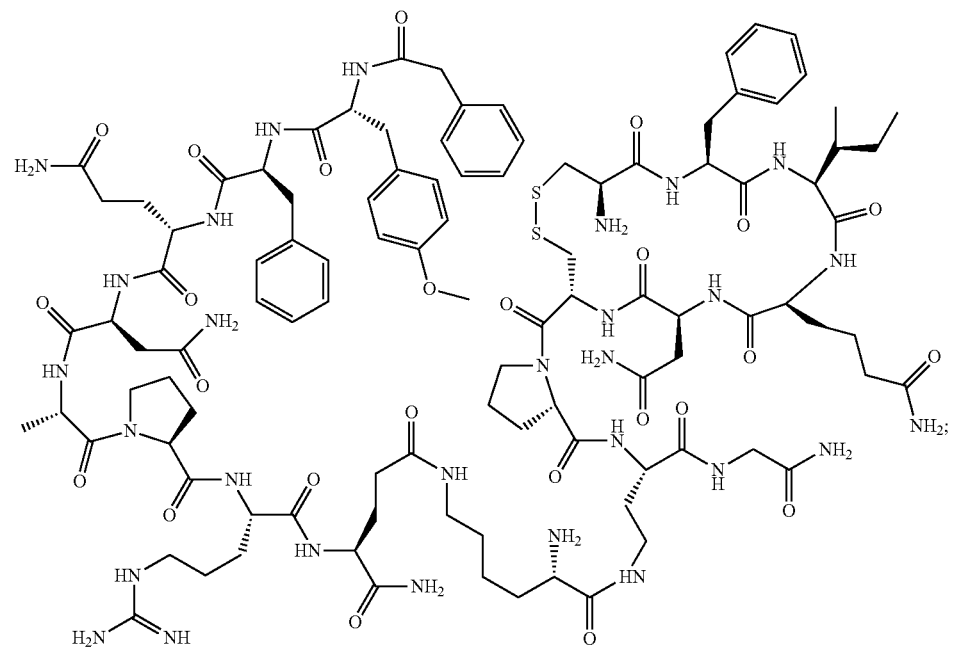

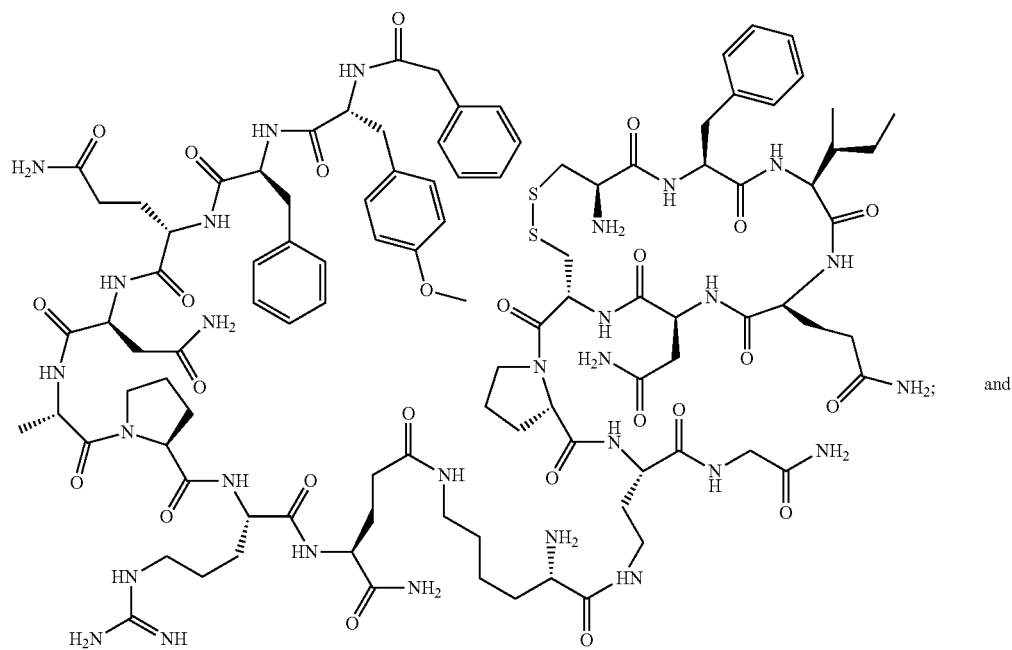
and
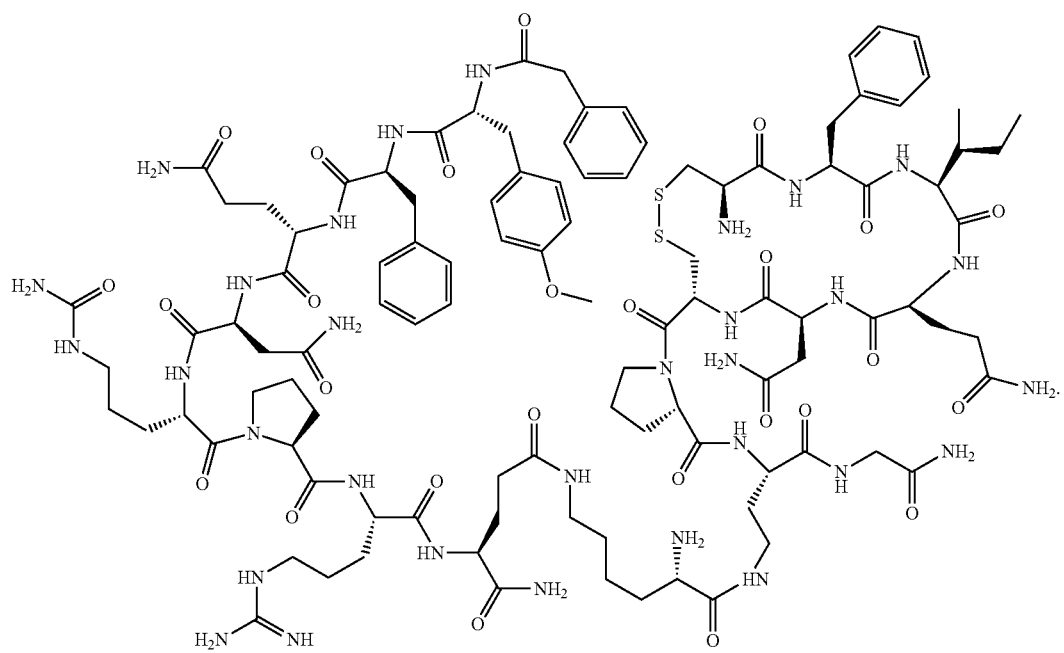

77. The method according to claim 68, wherein the compound is a compound of the following formula:
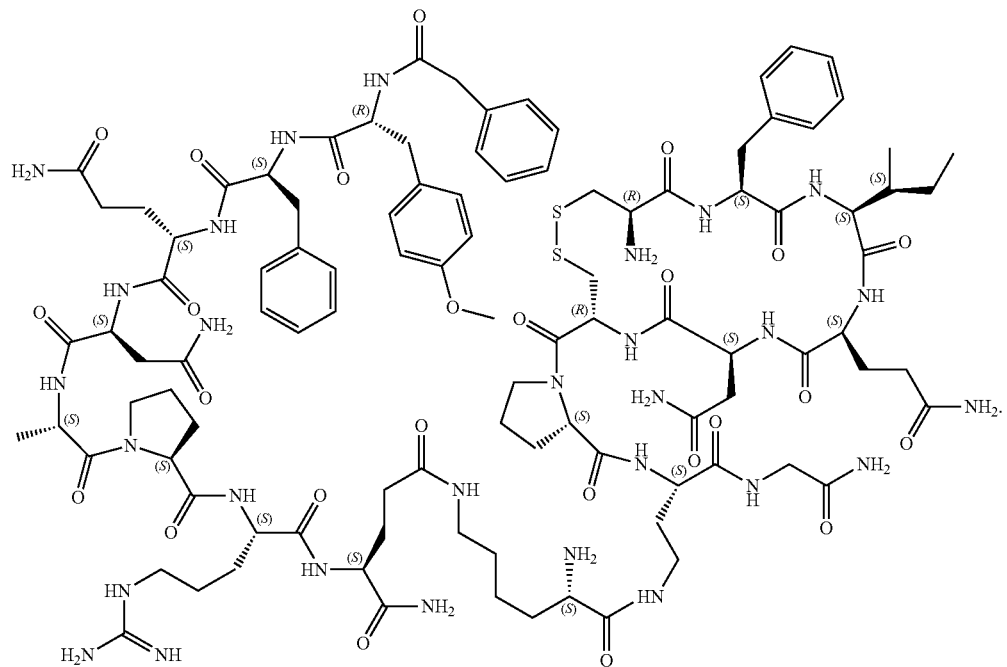
78. The method according to claim 68, wherein the compound is a compound of the following formula:
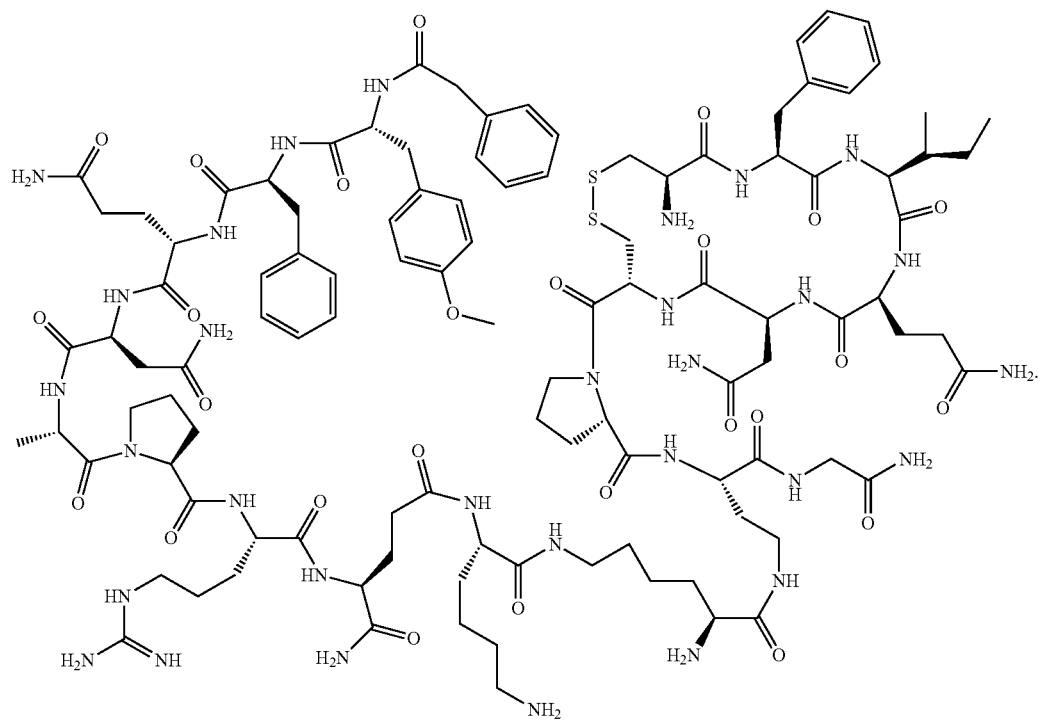 [SMILES: CC[C@H](C)[C@@H]1NC(=O)[C@H](Cc2ccccc2)NC(=O)[C@@H](N)CSSC[C@@H](C(=O)N2CCC[C@H]2C(=O)N[C@@H](CCNC(=O)[C@@H](N)CCCCNC(=O)[C@H](CCCCN)NC(=O)CC[C@H](NC(=O)[C@H](CCCNC(=N)N)NC(=O)[C@@H]2CCCN2C(=O)[C@H](C)NC(=O)[C@H](CC(N)=O)NC(=O)[C@H](CCC(N)=O)NC(=O)[C@H](Cc2ccccc2)NC(=O)[C@@H](Cc2ccc(OC)cc2)NC(=O)Cc2ccccc2)C(N)=O)C(=O)NCC(N)=O)NC(=O)[C@H](CC(N)=O)NC(=O)[C@H](CCC(N)=O)NC1=O]

79. The method according to claim 68, wherein the compound is a compound of the following formula:
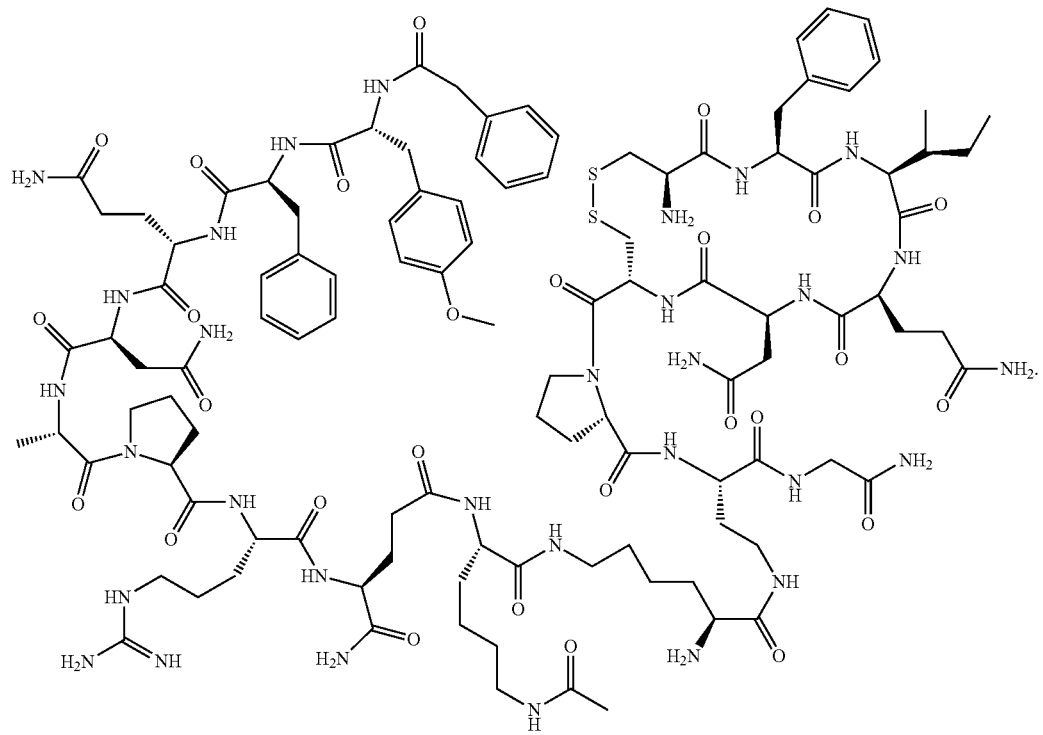 [SMILES: CC[C@H](C)[C@@H]1NC(=O)[C@H](Cc2ccccc2)NC(=O)[C@@H](N)CSSC[C@@H](C(=O)N2CCC[C@H]2C(=O)N[C@@H](CCNC(=O)[C@@H](N)CCCCNC(=O)[C@H](CCCCNC(C)=O)NC(=O)CC[C@H](NC(=O)[C@H](CCCNC(=N)N)NC(=O)[C@@H]2CCCN2C(=O)[C@H](C)NC(=O)[C@H](CC(N)=O)NC(=O)[C@H](CCC(N)=O)NC(=O)[C@H](Cc2ccccc2)NC(=O)[C@@H](Cc2ccc(OC)cc2)NC(=O)Cc2ccccc2)C(N)=O)C(=O)NCC(N)=O)NC(=O)[C@H](CC(N)=O)NC(=O)[C@H](CCC(N)=O)NC1=O]
* * * * *

UNITED STATES PATENT AND TRADEMARK OFFICE
CERTIFICATE OF CORRECTION

PATENT NO. : 9,644,000 B2
APPLICATION NO. : 14/400282
DATED : May 9, 2017
INVENTOR(S) : Wisniewski et al.

It is certified that error appears in the above-identified patent and that said Letters Patent is hereby corrected as shown below:

In the Specification

Column 1, Line 6: delete "371" and insert -- § 371 --.

In the Claims

Column 62, Line 35: in Claim 1, delete "Cy³-" and insert -- Cy³ --.

Column 64, Line 21: in Claim 2, delete "Ar³—" and insert -- Ar³ --.

Column 64, Line 22: in Claim 2, delete "C₁-C₆)" and insert -- (C₁-C₆) --.

Column 65, Line 15: in Claim 8, delete "Ar³—" and insert -- Ar³ --.

Column 66, Line 45: in Claim 42, delete "-C(=)—" and insert -- -C(=O)— --.

Column 68, Line 7: in Claim 51, delete "sobutyl," and insert -- isobutyl, --.

Column 73-74, Line 54: in Claim 52, delete ";" and insert therefor -- . --.

Column 75, Line 6: in Claim 54, delete:

"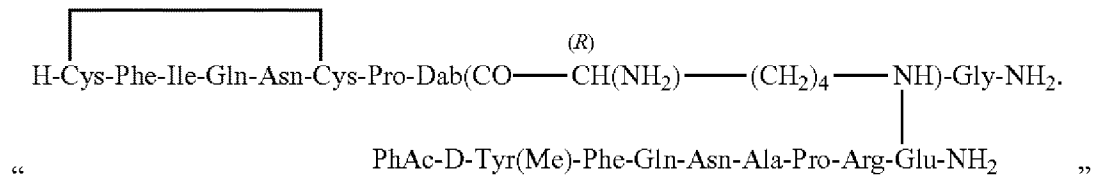"

Signed and Sealed this
Twelfth Day of February, 2019

Andrei Iancu
*Director of the United States Patent and Trademark Office*

CERTIFICATE OF CORRECTION (continued)
U.S. Pat. No. 9,644,000 B2

And insert:

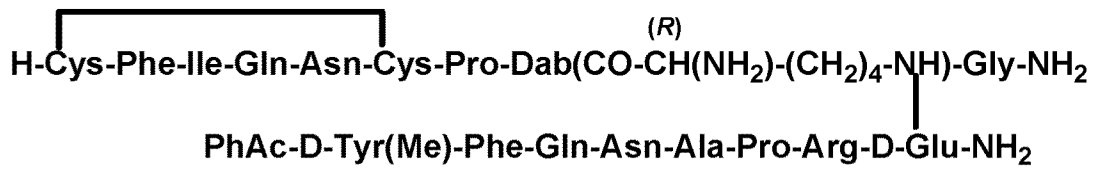

-- --.

Column 75-76, Line 11: in Claim 55, delete:

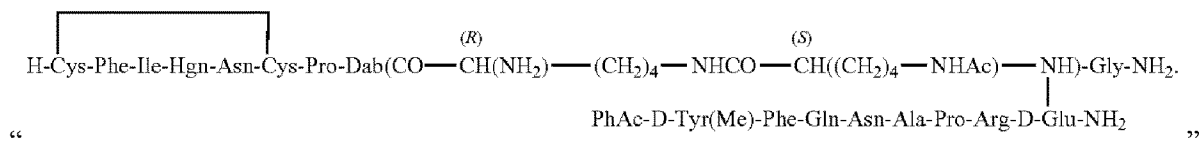

" "

And insert:

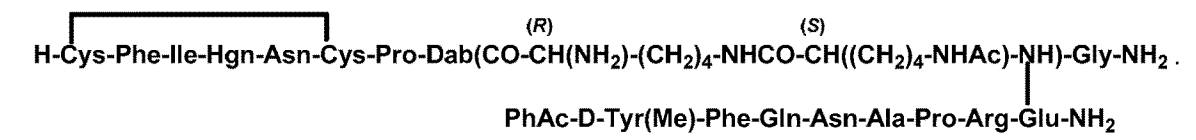

-- --.

Column 75-76, Line 14: in Claim 56, delete:

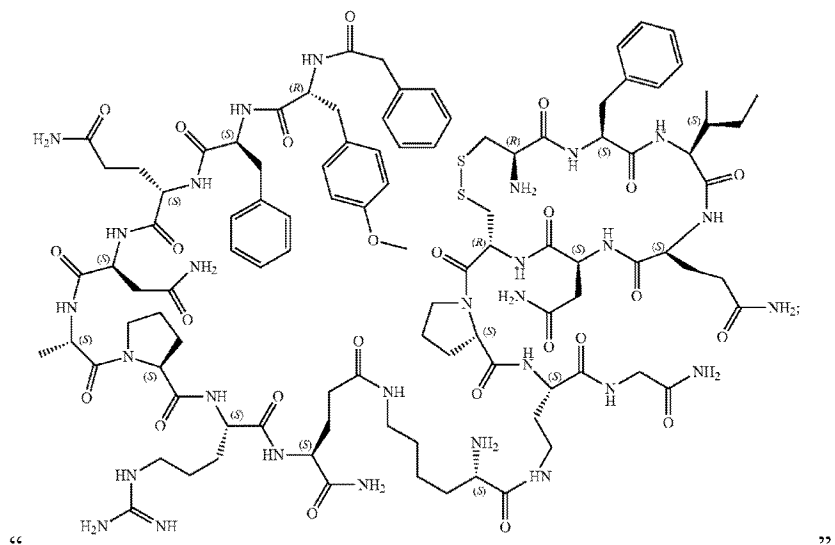

" "

And insert:
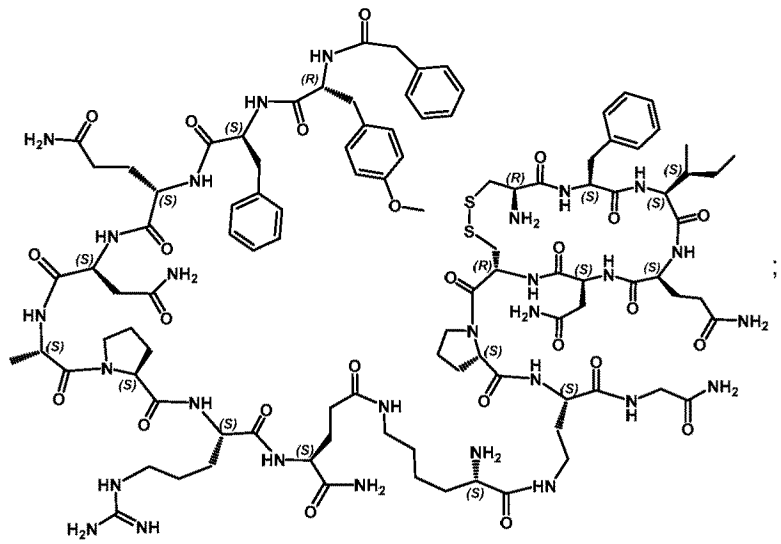
-- --.
Column 77-78, Line 2: in Claim 56, delete:
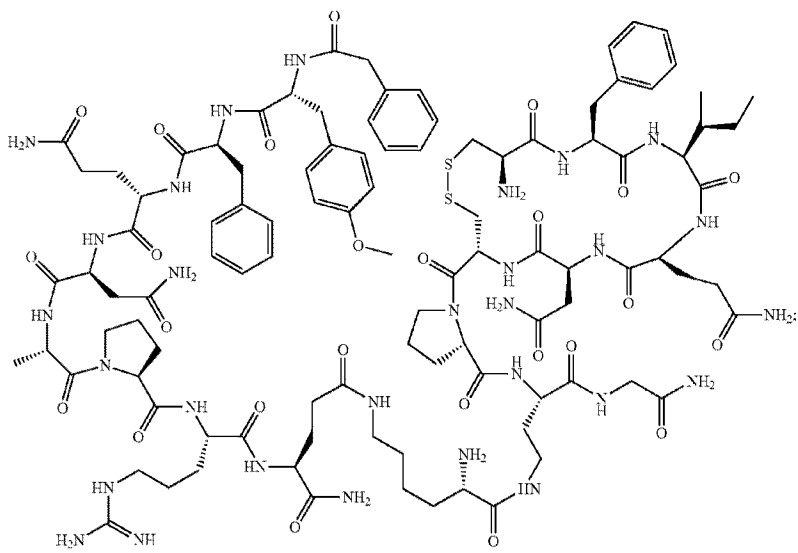
" "
And insert:

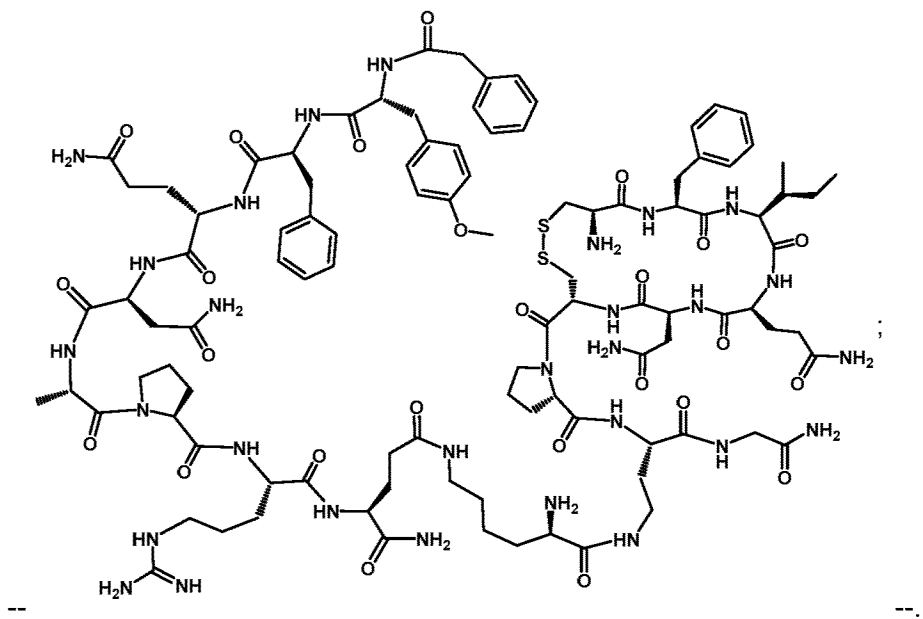
--.
Column 81-82, Line 35 (approx.): in Claim 56, delete:
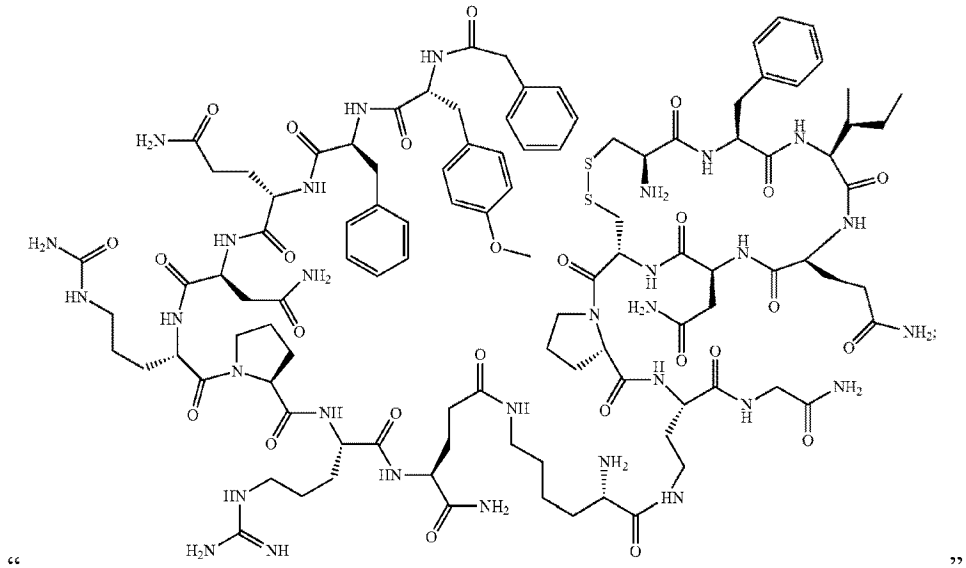
"
"
And insert:

CERTIFICATE OF CORRECTION (continued)
U.S. Pat. No. 9,644,000 B2

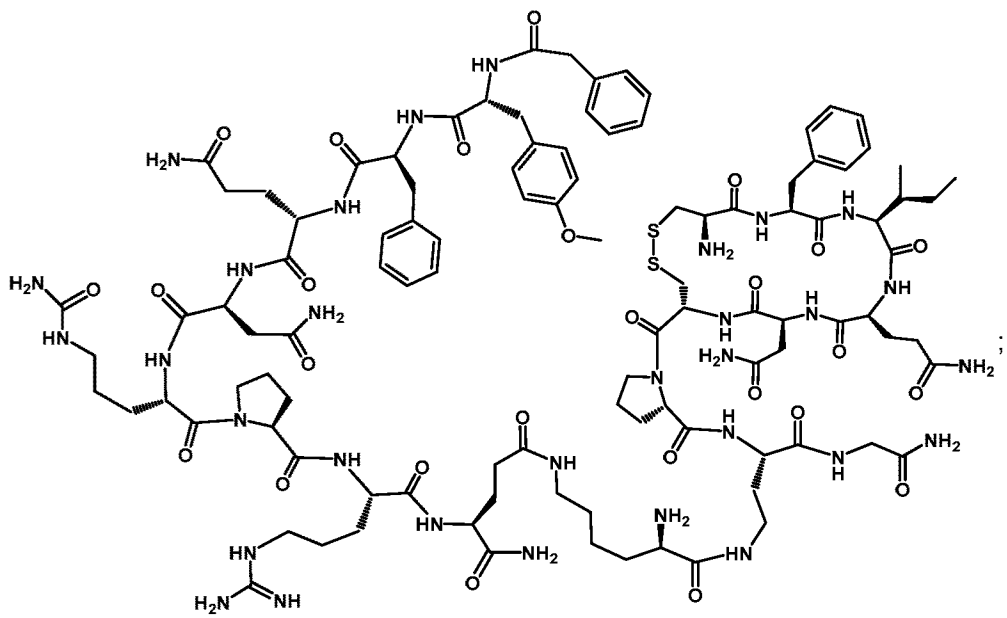

--

--.

Column 83-84, Line 35 (approx.): in Claim 56, delete:

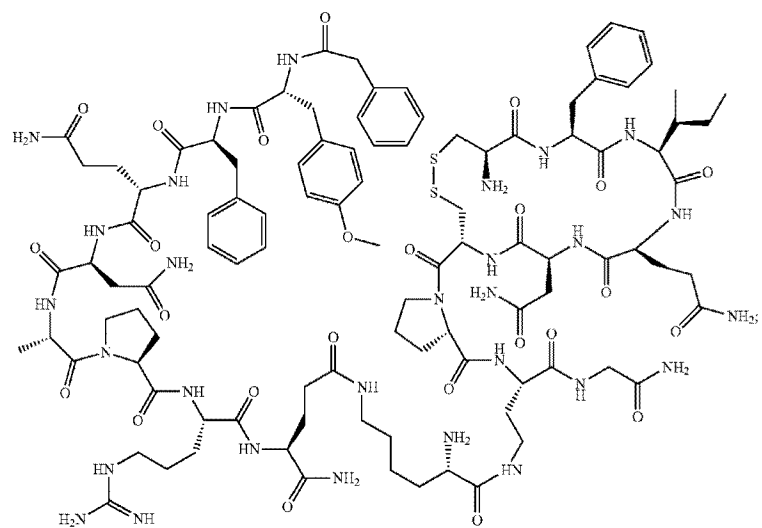

"                                                                    "

And insert:

CERTIFICATE OF CORRECTION (continued)
U.S. Pat. No. 9,644,000 B2

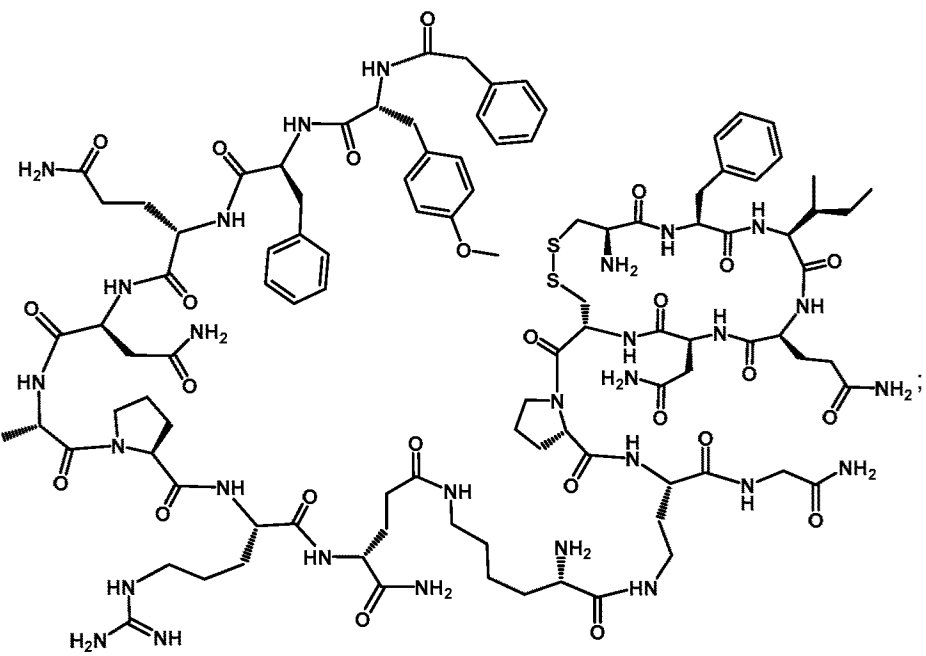

--

Column 85-86, Line 2: in Claim 56, delete:

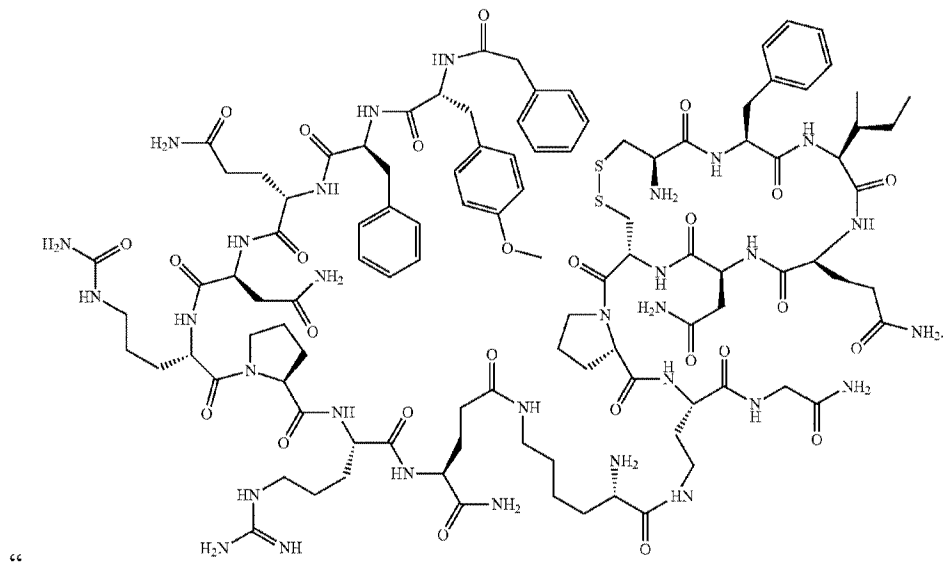

"                                                                                                                          "

And insert:

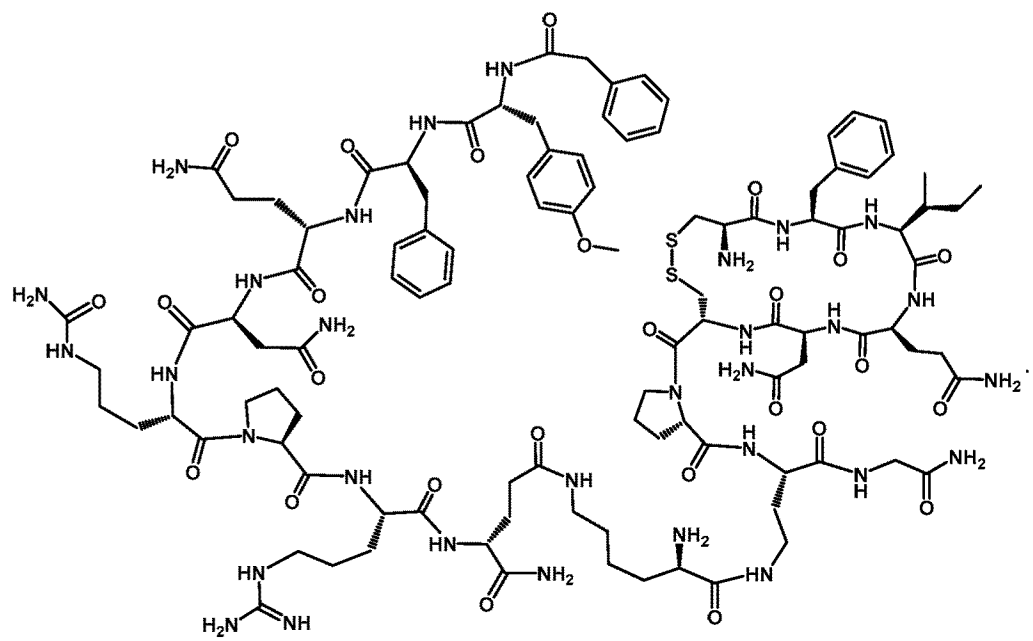
--            --.
Column 85-86, Line 38: in Claim 57, delete:
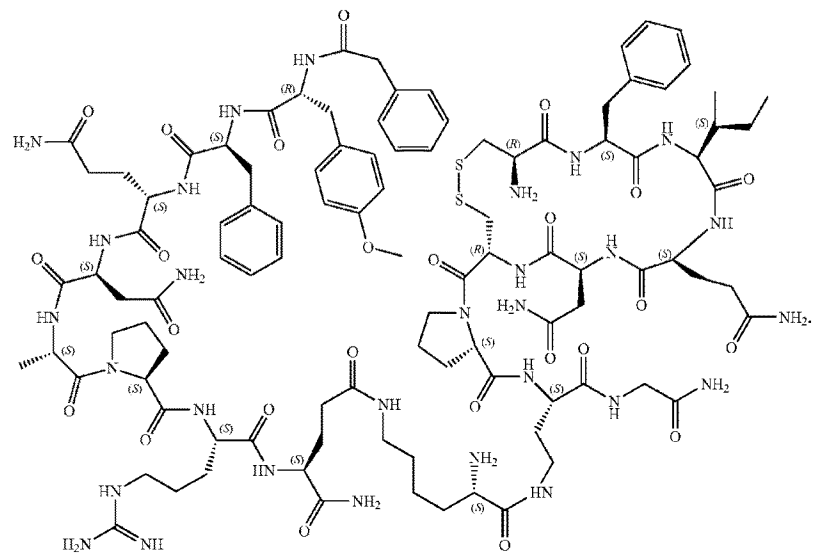
"            "
And insert:

CERTIFICATE OF CORRECTION (continued)
U.S. Pat. No. 9,644,000 B2

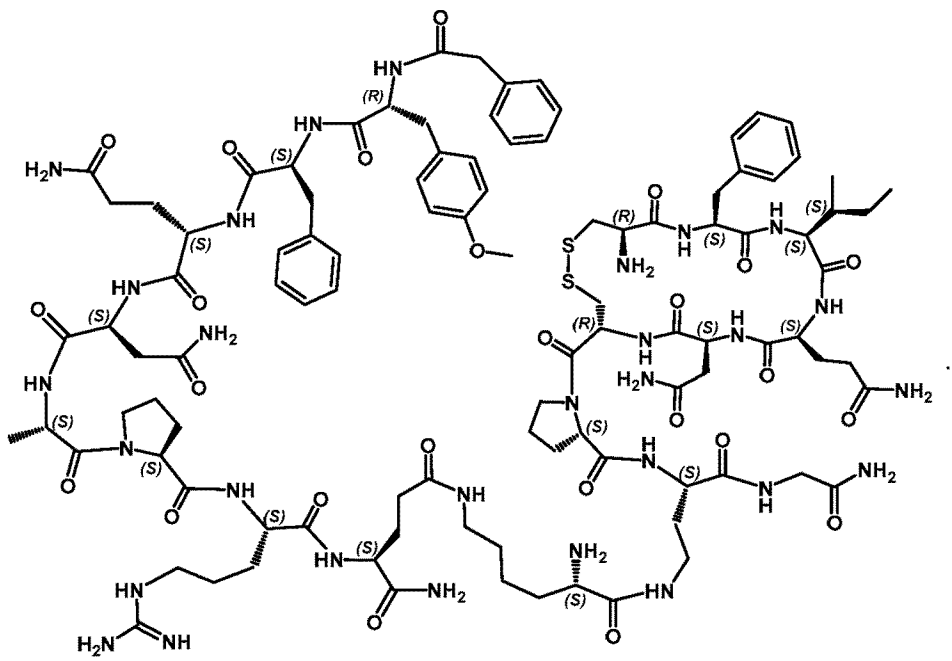

--                                                                          --.

Column 95-96, Line 55 (approx.): in Claim 75, delete:

"
H-Cys-Phe-Ile-Gln-Asn-Cys-Pro-Dab(CO—(R)CH(NH₂)—(CH₂)₄—NH)-Gly-NH₂;
                                                          |
                    PhAc-D-Tyr(Me)-Phe-Gln-Asn-Ala-Pro-Arg-Glu-NH₂
"

And insert:

H-Cys-Phe-Ile-Gln-Asn-Cys-Pro-Dab(CO-CH(NH₂)-(CH₂)₄-NH)-Gly-NH₂ ;
                                                          |
           PhAc-D-Tyr(Me)-Phe-Gln-Asn-Ala-Pro-Arg-D-Glu-NH₂

--                                                                          --.

Column 97-98, Line 1: in Claim 76, delete:

CERTIFICATE OF CORRECTION (continued)
U.S. Pat. No. 9,644,000 B2

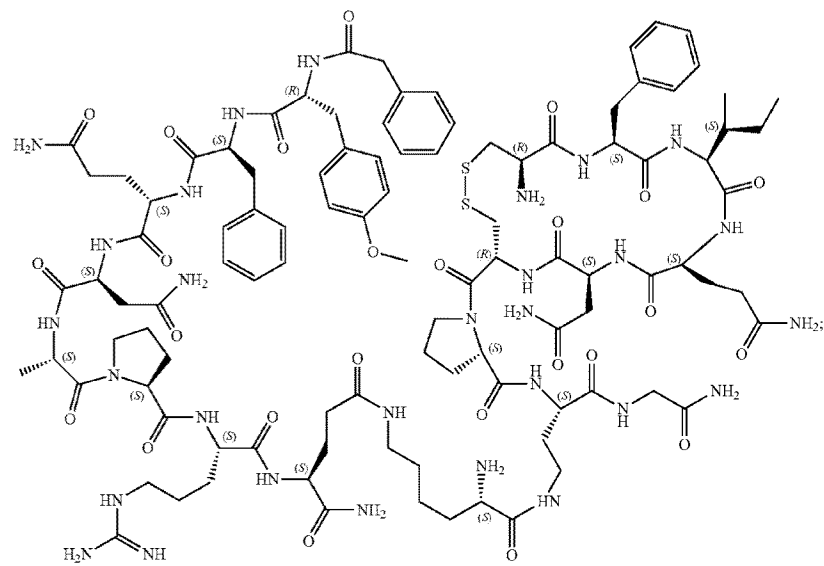

"

And insert:

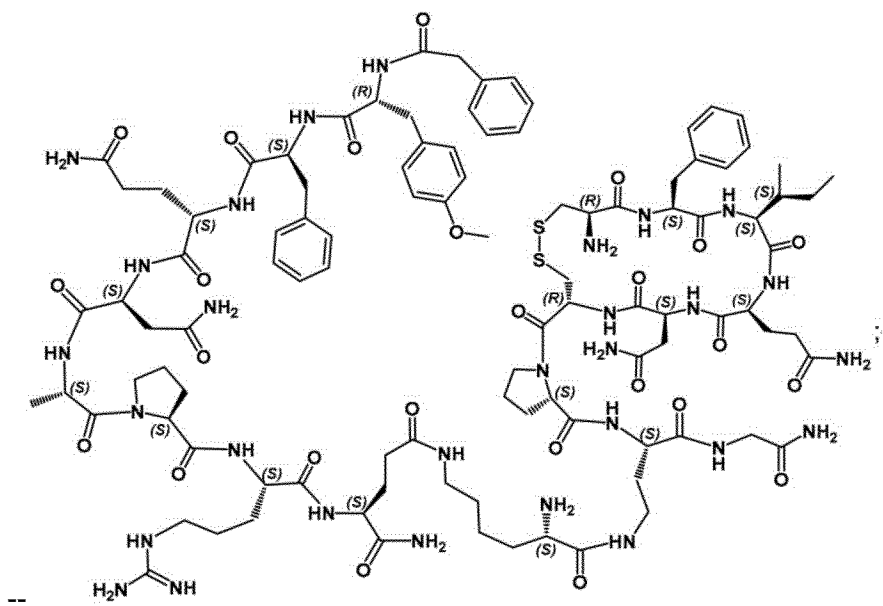

--  --.

Column 101-102, Line 2: in Claim 76, delete:

"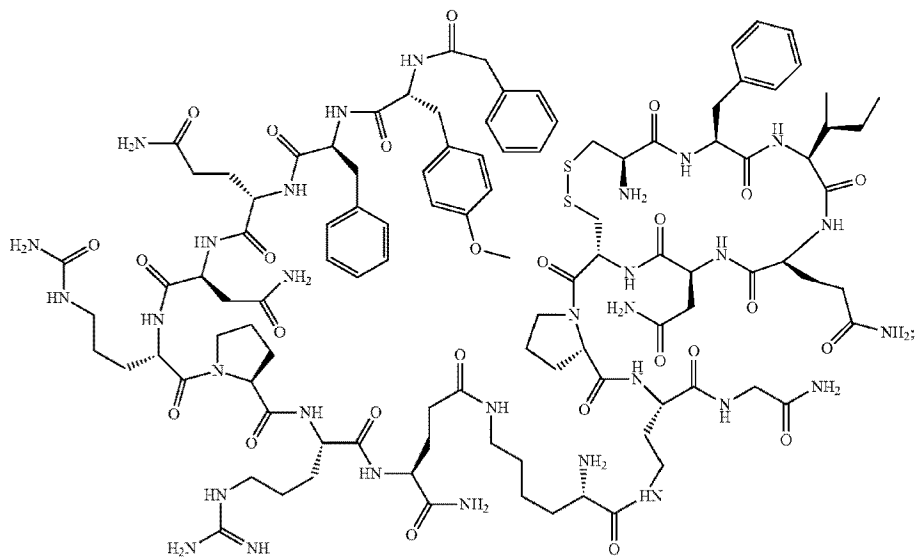"
And insert:
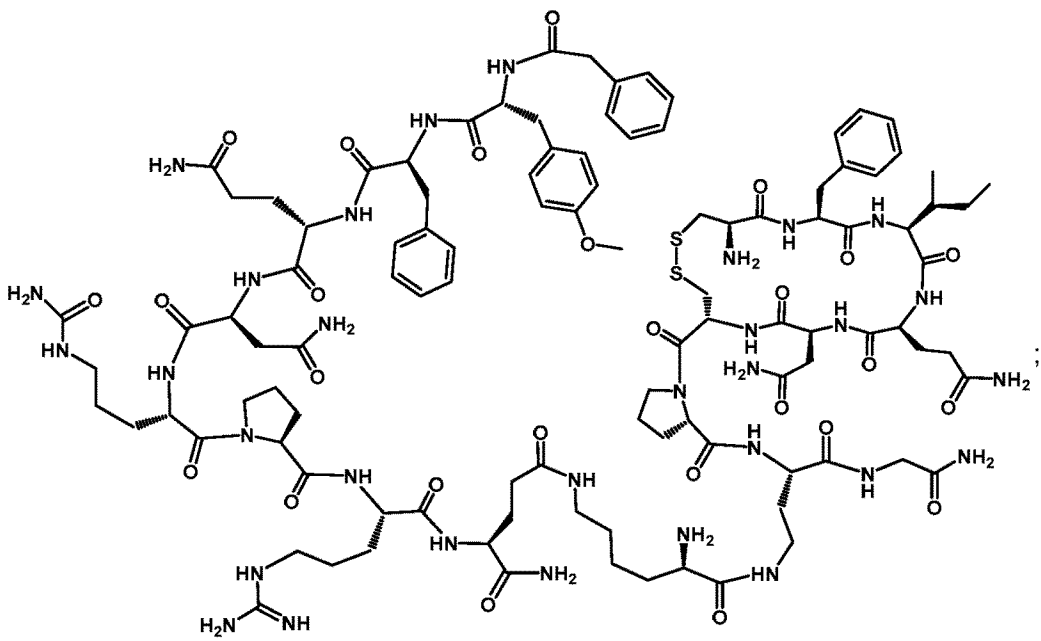
--            --.
Column 105-106, Line 2: in Claim 76, delete:

"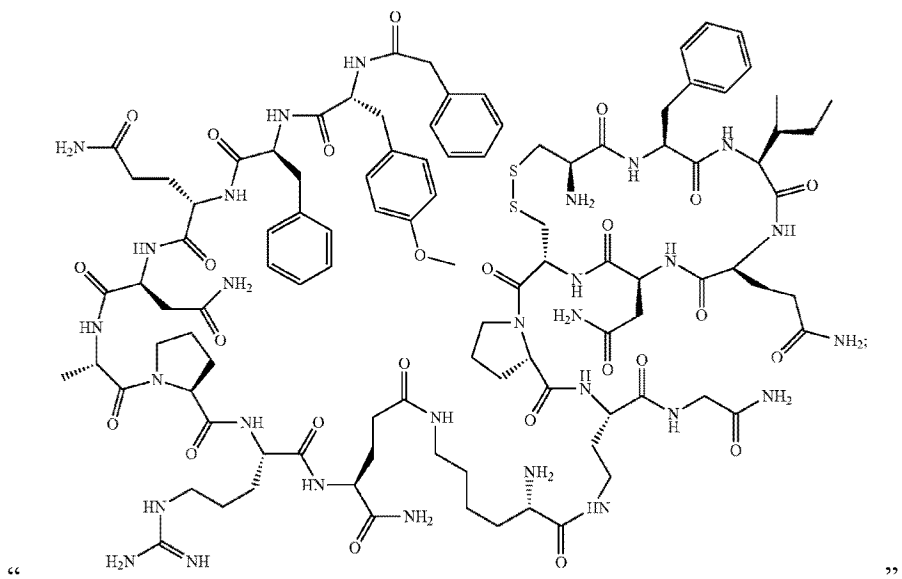"
And insert:
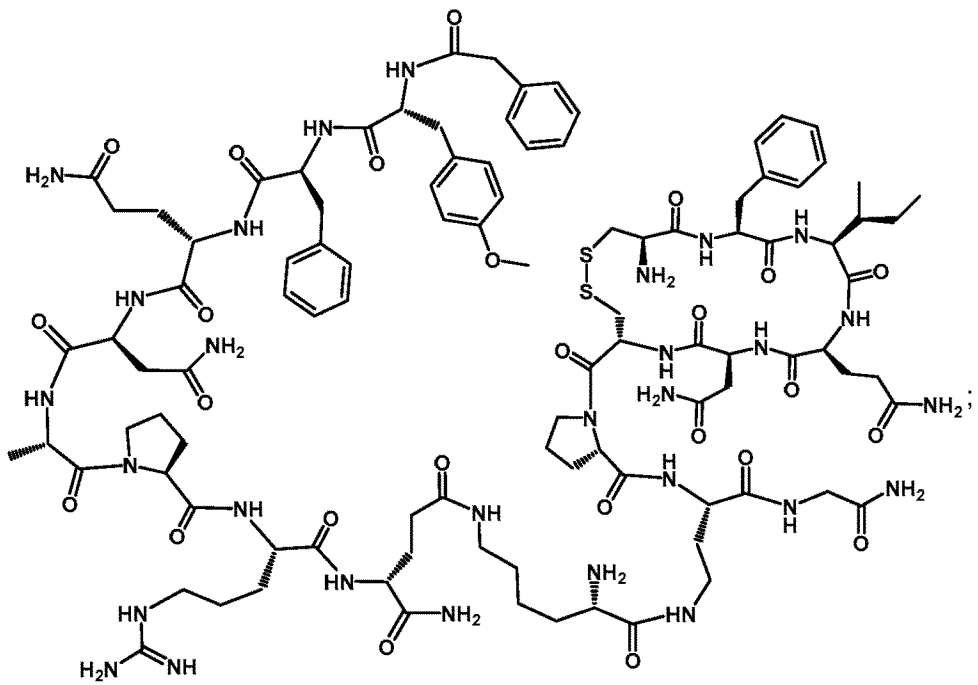
-- --.
Column 105-106, Line 35 (approx.): in Claim 76, delete:

"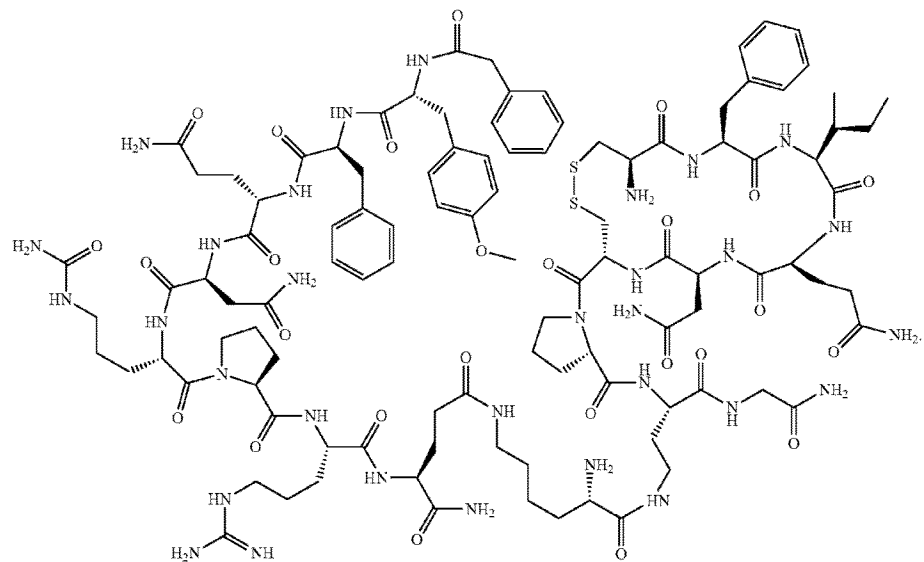"
And insert:
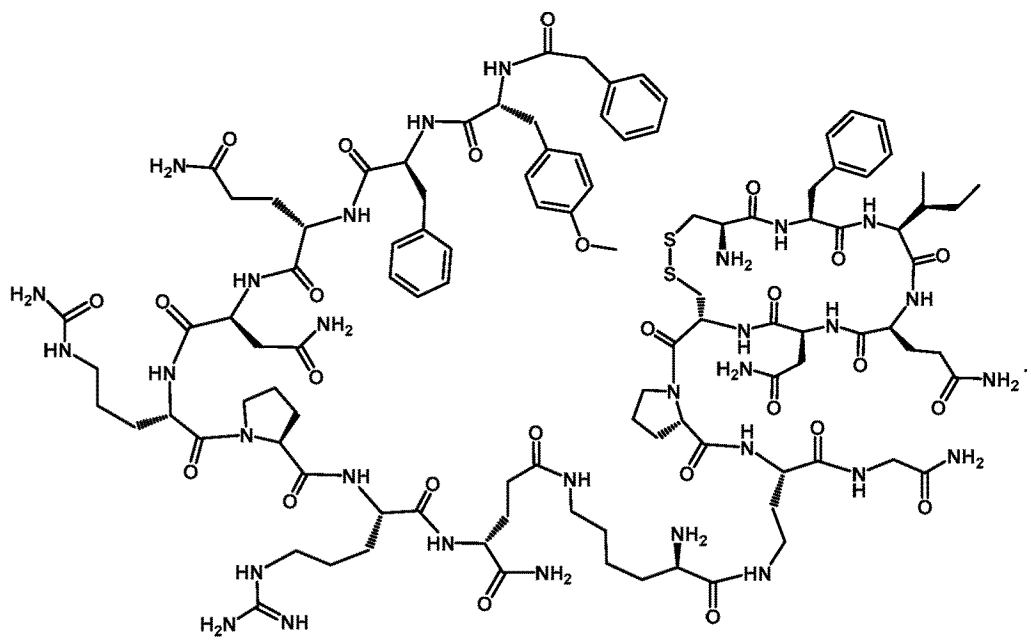
--                                                                          --.